United States Patent
Phan et al.

(10) Patent No.: US 9,901,392 B2
(45) Date of Patent: Feb. 27, 2018

(54) SYSTEM FOR USE IN TREATMENT OF VERTEBRAL FRACTURES

(71) Applicant: Dfine, Inc., South Jordan, UT (US)

(72) Inventors: Chris Phan, Dublin, CA (US); Craig Purdy, Sunnyvale, CA (US); Daniel Balbierz, Redwood City, CA (US)

(73) Assignee: Dfine, Inc., South Jordan, UT (US)

( * ) Notice: Subject to any disclaimer, the term of this patent is extended or adjusted under 35 U.S.C. 154(b) by 0 days.

(21) Appl. No.: 14/815,812

(22) Filed: Jul. 31, 2015

(65) Prior Publication Data

US 2016/0331443 A1    Nov. 17, 2016

Related U.S. Application Data

(60) Provisional application No. 62/159,806, filed on May 11, 2015.

(51) Int. Cl.
| | |
|---|---|
| A61B 17/58 | (2006.01) |
| A61B 17/60 | (2006.01) |
| A61F 2/00 | (2006.01) |
| A61B 18/14 | (2006.01) |
| A61B 17/16 | (2006.01) |
| A61B 17/00 | (2006.01) |
| A61B 18/00 | (2006.01) |

(52) U.S. Cl.
CPC ...... *A61B 18/1477* (2013.01); *A61B 17/1671* (2013.01); *A61B 18/148* (2013.01); *A61B 18/1442* (2013.01); *A61B 2017/00309* (2013.01); *A61B 2017/00323* (2013.01); *A61B 2017/00986* (2013.01); *A61B 2018/00202* (2013.01); *A61B 2018/00565* (2013.01); *A61B 2018/00577* (2013.01); *A61B 2018/00589* (2013.01)

(58) Field of Classification Search
None
See application file for complete search history.

(56) References Cited

U.S. PATENT DOCUMENTS

| | | |
|---|---|---|
| 3,140,623 A | 7/1964 | Hoose |
| 4,411,266 A | 10/1983 | Cosman |
| 4,456,017 A | 6/1984 | Miles |
| 4,476,861 A | 10/1984 | Dimakos et al. |
| 4,595,006 A | 6/1986 | Burke et al. |
| 5,282,821 A | 2/1994 | Donahue |
| 5,284,128 A | 2/1994 | Hart |
| 5,322,505 A | 6/1994 | Krause et al. |

(Continued)

FOREIGN PATENT DOCUMENTS

| | | |
|---|---|---|
| CN | 2841051 | 11/2006 |
| JP | 2004-242936 | 9/2004 |

(Continued)

*Primary Examiner* — Sameh Boles
(74) *Attorney, Agent, or Firm* — Stoel Rives LLP

(57) ABSTRACT

Devices having a shaft for creating cavities within tissue and articulating without twisting of the articulated shaft and methods for using such devices. Where such devices and methods include using of a device with keyed portions and key receiving portions that nest together upon articulation and optionally a torque limiter to allow for rotation of the shaft upon exceeding a torque limit. Method and devices also including such devices with energy application portions.

13 Claims, 55 Drawing Sheets

(56) References Cited

U.S. PATENT DOCUMENTS

| | | |
|---|---|---|
| 5,449,351 A | 9/1995 | Zohmann |
| 5,458,597 A | 10/1995 | Edwards et al. |
| 5,599,346 A | 2/1997 | Edwards et al. |
| 5,620,447 A | 4/1997 | Smith et al. |
| 5,628,771 A | 5/1997 | Mizukawa et al. |
| 5,662,680 A | 9/1997 | Desai |
| 5,695,513 A | 12/1997 | Johnson et al. |
| 5,697,536 A | 12/1997 | Eggers |
| 5,810,804 A | 9/1998 | Gough et al. |
| 5,833,632 A | 11/1998 | Jacobsen et al. |
| 5,849,028 A | 12/1998 | Chen |
| 5,851,212 A | 12/1998 | Zirps et al. |
| 5,902,251 A | 5/1999 | vanHooydonk |
| 5,921,956 A | 7/1999 | Grinberg et al. |
| 5,928,239 A | 7/1999 | Mirza |
| 5,944,715 A | 8/1999 | Goble et al. |
| 6,073,051 A | 6/2000 | Sharkey et al. |
| 6,106,524 A | 8/2000 | Eggers et al. |
| 6,123,702 A | 9/2000 | Swanson et al. |
| 6,135,999 A | 10/2000 | Fanton et al. |
| 6,231,615 B1 | 5/2001 | Preissman |
| 6,280,441 B1 | 8/2001 | Ryan |
| 6,409,722 B1 | 6/2002 | Hoey et al. |
| 6,440,138 B1 | 8/2002 | Reiley et al. |
| 6,447,506 B1 | 9/2002 | Swanson et al. |
| 6,464,683 B1 | 10/2002 | Samuelson et al. |
| 6,478,793 B1 | 11/2002 | Cosman et al. |
| 6,602,248 B1 | 8/2003 | Sharps et al. |
| 6,622,731 B2 | 9/2003 | Daniel et al. |
| 6,863,672 B2 | 3/2005 | Reiley et al. |
| 6,881,214 B2 | 4/2005 | Cosman et al. |
| 7,022,133 B2 | 4/2006 | Yee et al. |
| 7,108,696 B2 | 9/2006 | Daniel et al. |
| 7,156,843 B2 | 1/2007 | Skarda |
| 7,186,234 B2 | 3/2007 | Dahla et al. |
| 7,267,683 B2 | 9/2007 | Sharkey et al. |
| 7,270,661 B2 | 9/2007 | Dahla et al. |
| 7,480,533 B2 | 1/2009 | Cosman et al. |
| 7,503,920 B2 | 3/2009 | Siegal |
| 7,569,054 B2 | 8/2009 | Michelson |
| 7,595,634 B2 | 9/2009 | Flandre et al. |
| 7,625,364 B2 | 12/2009 | Corcoran et al. |
| 7,905,884 B2 | 3/2011 | Simonton et al. |
| 8,246,627 B2 | 8/2012 | Vanleeuwen et al. |
| 8,591,507 B2 | 11/2013 | Kramer et al. |
| 8,663,226 B2 | 3/2014 | Germain |
| 8,758,349 B2 | 6/2014 | Germain et al. |
| 8,864,760 B2 | 10/2014 | Kramer et al. |
| 9,113,974 B2 | 8/2015 | Germain |
| 9,125,671 B2 | 9/2015 | Germain et al. |
| 9,161,809 B2 | 10/2015 | Germain et al. |
| 2002/0026197 A1 | 2/2002 | Foley et al. |
| 2002/0133148 A1 | 9/2002 | Daniel et al. |
| 2003/0014094 A1 | 1/2003 | Hammack et al. |
| 2003/0130664 A1 | 7/2003 | Boucher et al. |
| 2003/0212394 A1 | 11/2003 | Pearson et al. |
| 2003/0212395 A1 | 11/2003 | Woloszko et al. |
| 2004/0087936 A1 | 5/2004 | Stern et al. |
| 2005/0055030 A1 | 3/2005 | Falahee |
| 2005/0090852 A1 | 4/2005 | Layne et al. |
| 2005/0177210 A1 | 8/2005 | Leung et al. |
| 2005/0216018 A1 | 9/2005 | Sennett |
| 2006/0025763 A1 | 2/2006 | Nelson et al. |
| 2006/0085009 A1 | 4/2006 | Truckai et al. |
| 2006/0264819 A1 | 11/2006 | Fischer et al. |
| 2007/0055281 A1 | 3/2007 | Osorio et al. |
| 2007/0156130 A1 | 7/2007 | Thistle |
| 2008/0004615 A1 | 1/2008 | Woloszko et al. |
| 2008/0033422 A1 | 2/2008 | Turner et al. |
| 2008/0058821 A1 | 3/2008 | Maurer et al. |
| 2008/0183165 A1 | 7/2008 | Buysse et al. |
| 2008/0208255 A1 | 8/2008 | Siegal |
| 2008/0228192 A1 | 9/2008 | Beyar et al. |
| 2008/0249525 A1 | 10/2008 | Lee et al. |
| 2008/0287741 A1 | 11/2008 | Ostrovsky et al. |
| 2009/0131948 A1 | 5/2009 | Liu et al. |
| 2009/0264892 A1 | 10/2009 | Beyar et al. |
| 2009/0299282 A1 | 12/2009 | Lau et al. |
| 2010/0082033 A1 | 4/2010 | Germain |
| 2010/0152724 A1 | 6/2010 | Marion et al. |
| 2010/0211076 A1 | 8/2010 | Germain et al. |
| 2011/0034884 A9 | 2/2011 | Pellegrino et al. |
| 2011/0160737 A1 | 6/2011 | Steffen et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0130381 A1* | 5/2012 | Germain ............ A61B 17/1642 606/84 |
| 2012/0330180 A1 | 12/2012 | Pellegrino et al. |
| 2012/0330301 A1 | 12/2012 | Pellegrino et al. |
| 2013/0041377 A1 | 2/2013 | Kuntz |
| 2013/0231654 A1 | 9/2013 | Germain |
| 2013/0261615 A1 | 10/2013 | Kramer et al. |
| 2013/0261621 A1 | 10/2013 | Kramer et al. |
| 2013/0345709 A1* | 12/2013 | Burger ............... A61B 17/8811 606/94 |
| 2014/0135779 A1 | 5/2014 | Germain |
| 2014/0163566 A1 | 6/2014 | Phan et al. |
| 2014/0350542 A1 | 11/2014 | Kramer et al. |
| 2014/0371740 A1 | 12/2014 | Germain et al. |
| 2015/0313614 A1 | 11/2015 | Germain |

FOREIGN PATENT DOCUMENTS

| | | |
|---|---|---|
| WO | WO 1993/004634 | 3/1993 |
| WO | WO 1997/003611 | 2/1997 |
| WO | WO 2003/101308 | 12/2003 |
| WO | WO 2008/076330 | 6/2008 |
| WO | WO 2008/084479 | 7/2008 |
| WO | WO 2010/039894 | 4/2010 |
| WO | WO 2010/081187 | 7/2010 |
| WO | WO 2011/137357 | 11/2011 |
| WO | WO 2011/137377 | 11/2011 |
| WO | WO 2012/071464 | 5/2012 |
| WO | WO 2013/147990 | 10/2013 |
| WO | WO 2014/093673 | 6/2014 |

* cited by examiner

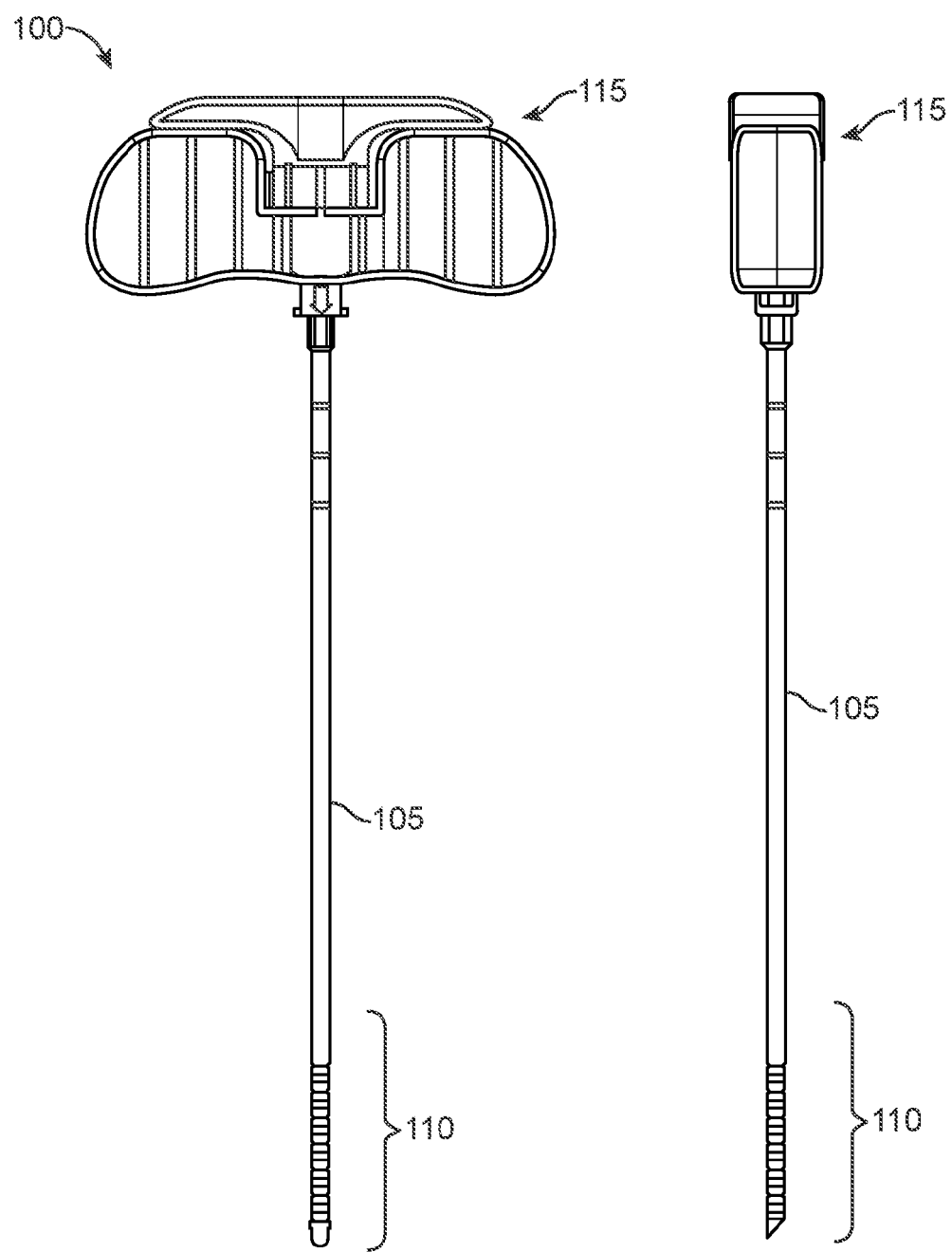

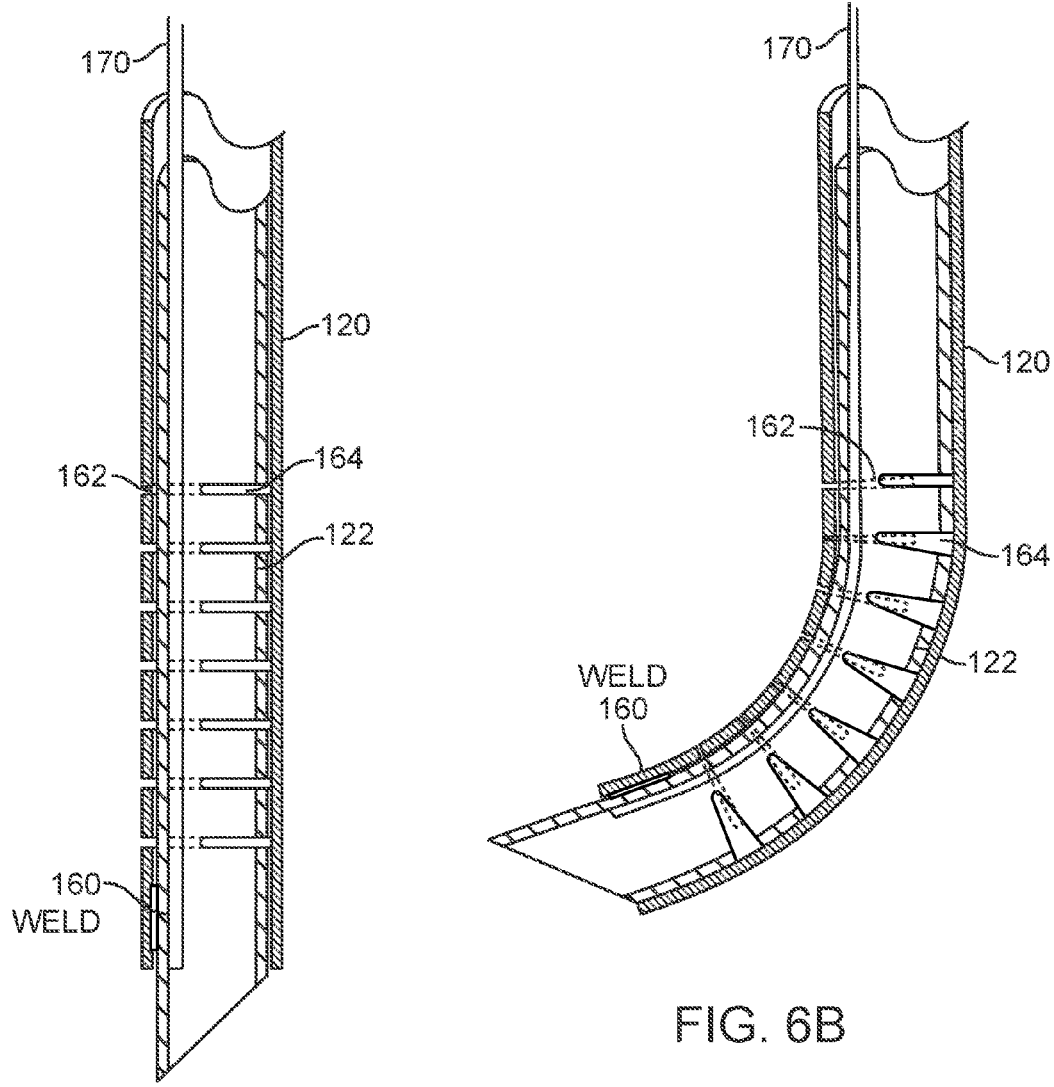

SYSTEM FOR USE IN TREATMENT OF VERTEBRAL FRACTURES

CROSS-REFERENCE TO RELATED APPLICATIONS

This application claims the benefit of priority to U.S. Provisional Patent Application No. 62/159,806, filed on May 11, 2015, the content of which is incorporated herein by reference in its entirety.

FIELD OF THE INVENTION

This invention relates to medical instruments and systems for creating a path or cavity in tissue to create a cavity, apply energy or deliver substances. The features relating to the methods and devices described herein can be applied in any region of tissue where tissue is displaced to define a bore or cavity. The devices and methods disclosed herein are provided to reduce twisting of an articulated section of the shaft as well as provide repeatable torque thresholds to limit unintentional excessive application of force to the treated region of the body. In addition, the present invention also discloses methods and devices for ablating or coagulating tissues, including but not limited to ablating tumor tissue in vertebral and/or cortical bone.

SUMMARY OF THE INVENTION

Methods and devices described herein relate to improved creation of a cavity, path, or opening within tissue, bone or other hard tissue where the cavity is created by displacement of the tissue. In a first example, a method according to the present disclosure includes treating a vertebral body or other bone structure.

One variation of the device includes a handle including an actuator member; a shaft extending from the handle and having a deflectable section that is moveable between a linear configuration and an articulated configuration upon application of an axial compression to the shaft upon movement of the actuator member; and where the shaft comprises at least a first sleeve having a plurality of first keyed slots, where the first keyed slot comprises a first edge that forms a first keyed portion and second edge that forms a first key receiving portion, where the where in the linear configuration the first keyed portion is separated from the first key receiving portion by a gap and upon assuming the articulated configuration the first keyed portion engages the first key receiving portion to nest together and increase a resistance to twisting deformation of the shaft, and where the first keyed portion and the first key receiving portion each comprises a first taper angle allowing the first keyed portion to nest together with the first key receiving portion forming a contiguous surface.

The variation of the device can include a plurality of proximal keyed slots each having a depth that varies from an adjacent proximal keyed slots where such a configuration can provide extra support at regions of high stress created during articulation and use of the device.

In an additional variation, the device can include a shaft that further comprises a second tube having a plurality of second slots and a plurality of second tabs slidably received in each of the second slots and located on a second side of the second tube opposite to the first side of the first tube; wherein movement of the actuation member causes compression of the first and the second tubes such that the first slots engage the first tabs and the second slots engage the second tabs to cause the deflectable section to assume the articulated configuration and to increase torsional resistance of the deflectable section.

The variations of the devices can include a second taper angle on the plurality of second slots and the plurality of second tabs each includes a second taper angle allowing the second keyed portion to nest together with the second key receiving portion forming a second contiguous surface.

Variations of the devices can further include a torque limiter having a torque threshold and rotatably coupling the first sleeve to the handle, where application of a torque exceeding the torque threshold causes rotation of the torque limiter relative to the handle to rotate the first sleeve.

In some variations, the torque limiter comprises a plurality of resistance surfaces that are deflected upon application of a rotational force to the shaft.

The devices described herein can also include a first conductive portion on the shaft electrically coupleable to a first pole of a power supply and a second conductive element coupled to the shaft being coupled to a second pole of the power supply.

In another variation, the invention includes a medical device for treating a region of tissue by mechanically displacing the tissue. In one example such a device comprises a handle including an actuator member; a shaft extending from the handle and having a deflectable section that is moveable between a linear configuration and an articulated configuration that can compress tissue as the shaft is moved in a linear direction, the shaft comprising a plurality of layers including at least a first layer and a second layer, the second layer being slidable relative to the first layer; the first layer located adjacent to a first side of the shaft and having a plurality of first recesses each forming a first slot with a first tab located therein, the first slot and first tab have a first taper causing an opening of the first slot to be wider than an end the first tab; the second layer located adjacent to a second side of the shaft, the second side of the shaft being radially opposite to the first side of the shaft, the second layer having a plurality of second recess each forming a second slot with a second tab located therein; and where in the linear configuration the first slot and first tab have a first clearance gap and the second slot and second tab have a second clearance gap, wherein movement of the actuation member causes compression of the shaft such that the first slot engages the first tab and the second slots engages the second tab to reduce the first clearance gap and second clearance gap causing movement of the deflectable section towards the articulated configuration and whereby reducing of the first clearance gap and second clearance gap increase torsional resistance of the deflectable section.

The present disclosure also includes methods of displacing tissue in a body. For example such a method can include providing a device with an axially-extending shaft having an articulating working end, wherein the working end comprises at least a first sleeve having a plurality of slots, where a first edge of each of the plurality of slots forms a keyed portion, and where a second edge of each of the plurality of slots forms a key receiving portion, where the keyed portion and key receiving portion comprise a tapered angle and where a surface circumferentially opposite to the plurality of slots is continuous each formed into is formed into arcuate shape; inserting the working end into tissue; and progressively articulating the working end through toward an increased curvature such that the tapered angle allows the key receiving portion and the keyed portion to form a contiguous surface and causing articulation of the articulating working end; rotating the articulating working when articulated to displace adjacent cancellous bone.

In an additional variation, the present devices include medical osteotome devices that can treat a hard tissue (e.g., in a vertebral body) by mechanically displacing the hard tissue and/or applying therapeutic energy to ablate or coagulate tissue. Another variations of the method disclosed herein can include the application of energy between electrodes on the device to ablate tissues (e.g., tumor) or to perform other electrosurgical or mapping procedures within the tissue.

In one such example for treating a vertebral body, the method can include providing an elongate tool having a sharp tip configured for penetration into vertebral bone, the tool having an axis extending from a proximal end to a working end thereof, where the working end comprises at least a first sleeve concentrically located within a second sleeve, where each sleeve comprises a series of slots or notches to limit deflection of the working end to a first curved configuration in a single plane and where the respective series of slots or notches are radially offset in adjacent sleeves, where a first conductive portion of the first sleeve is electrically coupled to a first pole of a power supply; advancing the working end through vertebral bone; causing the working end to move from a linear configuration to a curved configuration by translating the first sleeve relative to the second sleeve in an axial direction; and applying energy between the first conductive portion and a return electrode electrically coupled to a second pole of the energy supply to ablate or coagulate a region within the vertebral body.

The method can further include the use of one or more cannulae to introduce the tool into the target region. Such a cannula can maintain the tool in a straight or linear configuration until the tool advances out of the cannula or until the cannula is withdrawn from over the tool.

As described herein, upon creation of the cavity, the method can further include the insertion of a filler material or other substance into the cavity. The filler material can be delivered through the tool or through a separate cannula or catheter.

Variations of the device can include one or more lumens that extend through the shaft and working end. These lumens can exit at a distal tip of the device or through a side opening in a wall of the device. The lumen can include a surface comprising a lubricious polymeric material. For example, the material can comprise any bio-compatible material having low frictional properties (e.g., TEFLON®, a polytetrafluroethylene (PTFE), FEP (Fluorinated ethylenepropylene), polyethylene, polyamide, ECTFE (Ethylenechlorotrifluoroethylene), ETFE, PVDF, polyvinyl chloride and silicone).

As described herein, the devices can include any number of configurations to prevent rotation between adjacent sleeves but allow axial movement between the sleeves. For example, the sleeves can be mechanically coupled via a pin/slot or key/keyway configuration. In an additional variation, the sleeves can be non-circular to prevent rotation.

In an additional variation, the disclosure includes various kits comprising the device described herein as well as a filler material (e.g., a bone cement or other bone filler material).

Variations of the access device and procedures described above include combinations of features of the various embodiments or combination of the embodiments themselves wherever possible.

The disclosure of this application is related to, and can be combined with the following commonly assigned patents U.S. Pat. No. 8,591,507 filed Jan. 31, 2013 issued on Nov. 26, 2013; U.S. Pat. No. 8,663,226 filed Sep. 30, 2009 issued on Mar. 04, 2014; U.S. Pat. No. 8,758,349 filed Oct. 13, 2009 issued on Jun. 24, 2014; and U.S. Pat. No. 8,864,760 filed Mar. 11, 2013 issued on Oct. 21, 2014; as well as the following commonly assigned U.S. patent applications: US-2014-0135779-A1 filed Jan. 16, 2014; US-2014-0371740-A1 filed Jun. 23, 2014; US-2011-0251615-A1 filed Apr. 08, 2011; US-2011-0295261-A1 filed Apr. 29, 2011; US-2013-0231654-A1 filed Mar. 29, 2013; US-2011-0295262-A1 filed Apr. 29, 2011; US-2012-0130381-A1 filed Nov. 22, 2011; US-2014-0350542-A1 filed Aug. 06, 2014; and US-2014-0163566-A1 filed Mar. 15, 2013. The entirety of each of the above patents and/or applications is incorporated by reference herein.

BRIEF DESCRIPTION OF DRAWINGS

FIG. 1 is a plan view of an osteotome of the invention.

FIG. 2 is a side view of the osteotome of FIG. 1.

FIG. 6A is a sectional view of the working end of FIG. 5 in a linear configuration.

FIG. 6B is a sectional view of the working end of FIG. 5 in a curved configuration.

FIG. 19A showing the working end in a linear shape for insertion into bone; FIG. 19B showing the working end in an articulated shape for creating a space in bone having a certain area.

DETAILED DESCRIPTION

Figure 3:
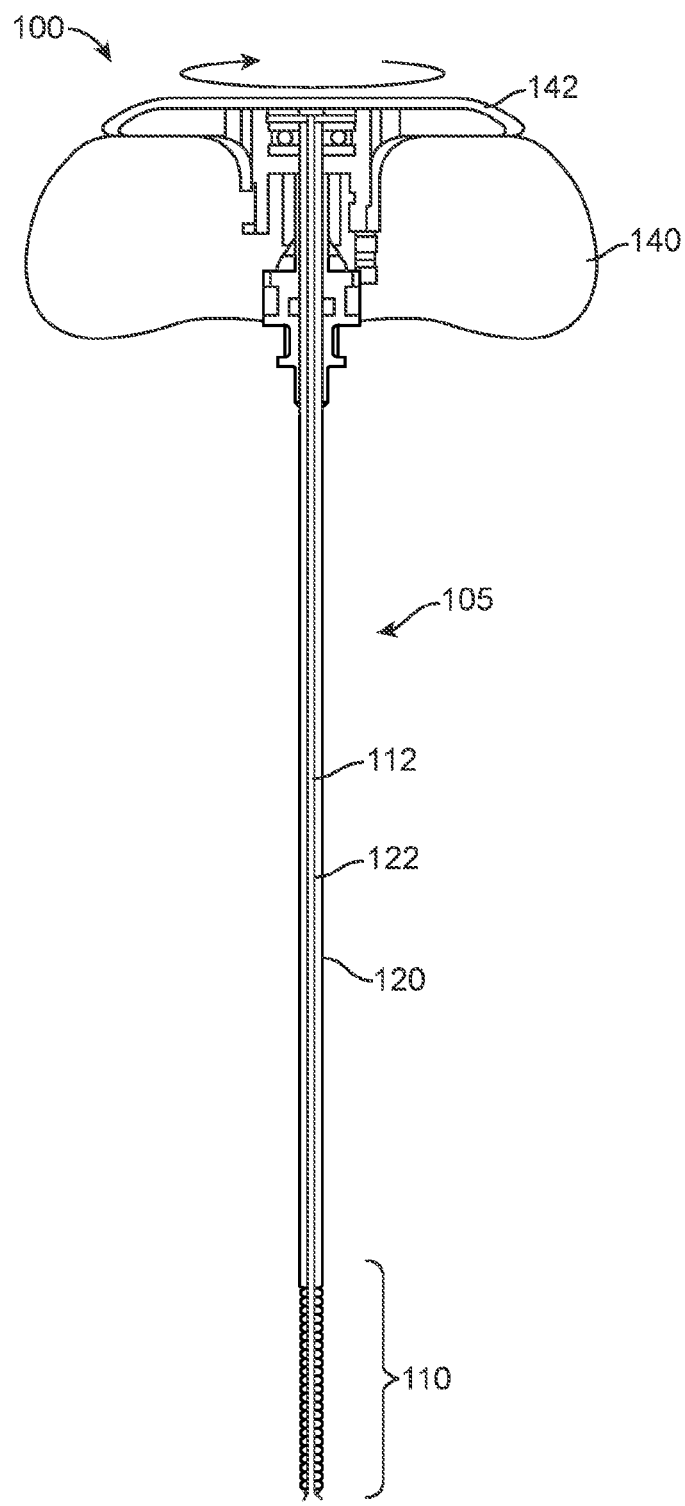
FIG. 3 is a cross sectional view of the osteotome of FIG. 1.

Referring to FIGS. 1-5, an apparatus or osteotome 100 is shown that is configured for accessing the interior of a vertebral body and for creating a pathway in vertebral cancellous bone to receive bone cement. In one embodiment, the apparatus is configured with an extension portion or member 105 for introducing through a pedicle and wherein a working end 110 of the extension member can be progressively actuated to curve a selected degree and/or rotated to create a curved pathway and cavity in the direction of the midline of the vertebral body. The apparatus can be withdrawn and bone fill material can be introduced through a bone cement injection cannula. Alternatively, the apparatus 100 itself can be used as a cement injector with the subsequent injection of cement through a lumen 112 of the apparatus.

In one embodiment, the apparatus 100 comprises a handle 115 that is coupled to a proximal end of the extension member 105. The extension member 105 comprises an assembly of first (outer) sleeve 120 and a second (inner) sleeve 122, with the first sleeve 120 having a proximal end 124 and distal end 126. The second sleeve 122 has a proximal end 134 and distal end 136. The extension member 105 is coupled to the handle 115, as will be described below, to allow a physician to drive the extension member 105 into bone while contemporaneously actuating the working end 110 into an actuated or curved configuration (see FIG. 6). The handle 115 can be fabricated of a polymer, metal or any other material suitable to withstand hammering or impact forces used to drive the assembly into bone (e.g., via use of a hammer or similar device on the handle 115). The inner and outer sleeves are fabricated of a suitable metal alloy, such as stainless steel or NiTi. The wall thicknesses of the inner and outer sleeves can range from about 0.005" to 0.010" with the outer diameter the outer sleeve ranging from about 2.5 mm to 5.0 mm.

Figure 4:
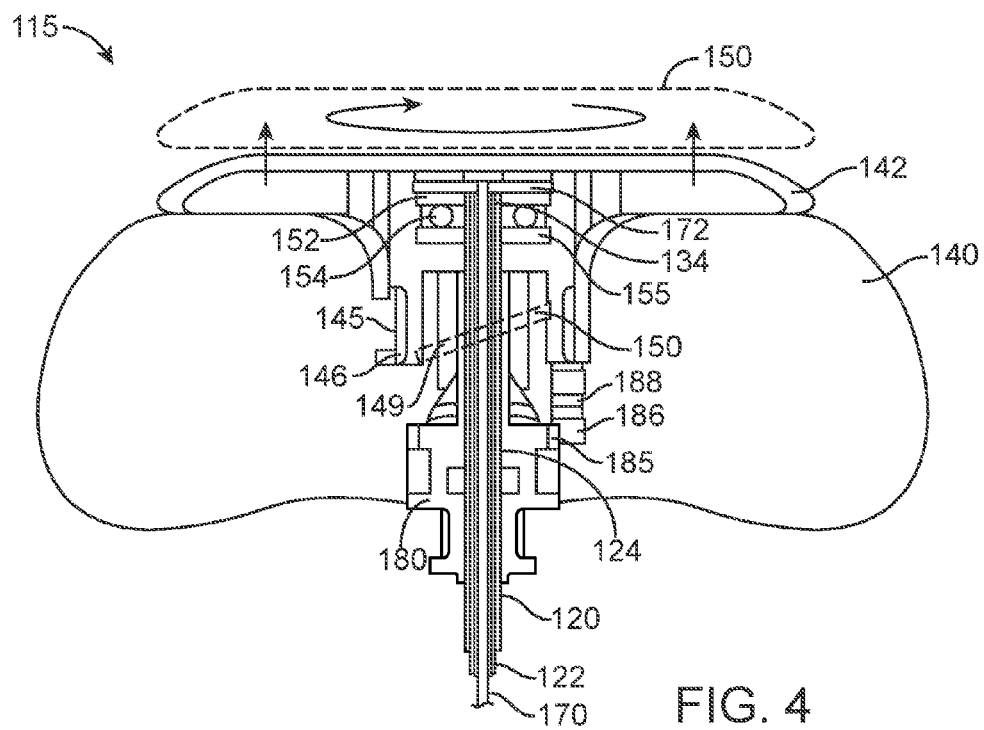
FIG. 4 is an enlarged sectional view of the handle of the osteotome of FIG. 1.

Referring to FIGS. 1, 3 and 4, the handle 115 comprises both a first grip portion 140 and a second actuator portion indicated at 142. The grip portion 140 is coupled to the first sleeve 120 as will be described below. The actuator portion 142 is operatively coupled to the second sleeve 122 as will be described below. The actuator portion 142 is rotatable relative to the grip portion 140 and one or more plastic flex tabs 145 of the grip portion 140 are configured to engage notches 146 in the rotatable actuator portion 142 to provide tactile indication and temporary locking of the handle portions 140 and 142 in a certain degree of rotation. The flex tabs 145 thus engage and disengage with the notches 146 to permit ratcheting (rotation and locking) of the handle portions and the respective sleeve coupled thereto.

The notches or slots in any of the sleeves can comprise a uniform width along the length of the working end or can comprise a varying width. Alternatively, the width can be selected in certain areas to effectuate a particular curved profile. In other variation, the width can increase or decrease along the working end to create a curve having a varying radius. Clearly, it is understood that any number of variations are within the scope of this disclosure.

FIG. 4 is a sectional view of the handle showing a mechanism for actuating the second inner sleeve 122 relative to the first outer sleeve 120. The actuator portion 142 of the handle 115 is configured with a fast-lead helical groove indicated at 150 that cooperates with a protruding thread 149 of the grip portion 140 of the handle. Thus, it can be understood that rotation of the actuation portion 142 will move this portion to the position indicated at 150 (phantom view). In one embodiment, when the actuator portion 142 is rotated a selected amount from about 45° to 720°, or from about 90° to 360°, the inner sleeve 122 is lifted proximally relative to the grip portion 140 and outer sleeve 120 to actuate the working end 110. As can be seen in FIG. 4 the actuator portion 142 engages flange 152 that is welded to the proximal end 132 of inner sleeve 122. The flange 152 is lifted by means of a ball bearing assembly 154 disposed between the flange 152 and metal bearing surface 155 inserted into the grip portion 140 of the handle. Thus, the rotation of actuator 142 can lift the inner sleeve 122 without creating torque on the inner sleeve.

Figure 5:
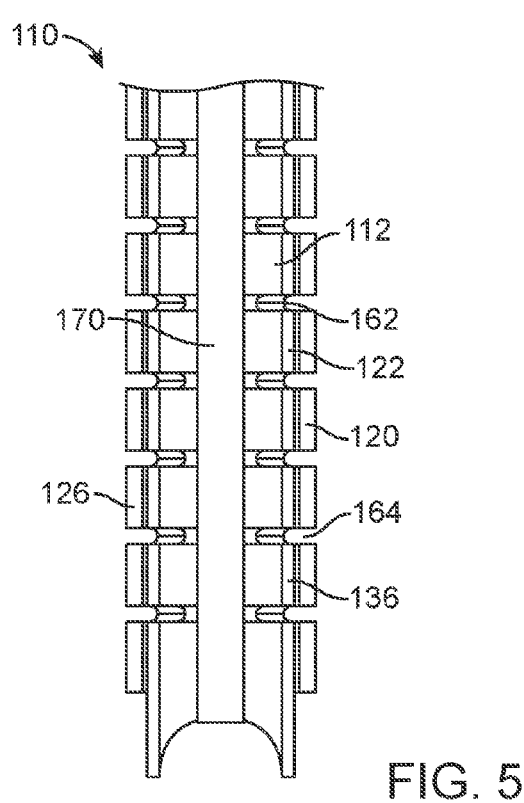
FIG. 5 is an enlarged sectional view of the working end of the osteotome of FIG. 1.

Now turning to FIGS. 5, 6A and 6B, it can be seen that the working end 110 of the extension member 105 is articulated by cooperating slotted portions of the distal portions of outer sleeve 120 and inner sleeve 122 that are both thus capable of bending in a substantially tight radius. The outer sleeve 120 has a plurality of slots or notches 162 therein that can be any slots that are perpendicular or angled relative to the axis of the sleeve. The inner sleeve 122 has a plurality of slots or notches indicated at 164 that can be on an opposite side of the assembly relative to the slots 162 in the outer sleeve 120. The outer and inner sleeves are welded together at the distal region indicated at weld 160. It thus can be understood that when inner sleeve 122 is translated in the proximal direction, the outer sleeve will be flexed as depicted in FIG. 6B. It can be understood that by rotating the actuator handle portion 142 a selected amount, the working end can be articulated to a selected degree.

FIG. 4, 5, 6A and 6B further illustrate another element of the apparatus that comprises a flexible flat wire member 170 with a proximal end 171 and flange 172 that is engages the proximal side of flange 152 of the inner sleeve 122. At least the distal portion 174 of the flat wire member 170 is welded to the inner sleeve at weld 175. This flat wire member thus provides a safety feature to retain the working end in the event that the inner sleeve fails at one of the slots 164.

Another safety feature of the apparatus comprises a torque limiter and release system that allows the entire handle assembly 115 to freely rotate—for example if the working end 110 is articulated, as in FIG. 6B, when the physician rotates the handle and when the working end is engaged in strong cancellous bone. Referring to FIG. 4, the grip portion 142 of the handle 115 engages a collar 180 that is fixed to a proximal end 124 of the outer sleeve 120. The collar 180 further comprises notches 185 that are radially spaced about the collar and are engaged by a ball member 186 that is pushed by a spring 188 into notches 185. At a selected force, for example a torque ranging from greater than about 0.5 inch*lbs but less that about 7.5 inch*lbs, 5.0 inch*lbs or 2.5 inch*lbs, the rotation of the handle 115 overcomes the predetermined limit. When the torque limiter assembly is in its locked position, the ball bearing 186 is forced into one of the notches 185 in the collar 180. When too much torque is provided to the handle and outer sleeve, the ball bearing 186 disengages the notch 185 allowing the collar 180 to turn, and then reengages at the next notch, releasing anywhere from 0.5 inch*lbs to 7.5 inch*lbs of torque.

Referring to FIGS. 6A and 6B, it can be understood that the inner sleeve 122 is weakened on one side at its distal portion so as to permit the inner sleeve 122 to bend in either direction but is limited by the location of the notches in the outer sleeve 120. The curvature of any articulated configuration is controlled by the spacing of the notches as well as the distance between each notch peak. The inner sleeve 122 also has a beveled tip for entry through the cortical bone of a vertebral body. Either the inner sleeve or outer sleeve can form the distal tip.

Figure 7A:
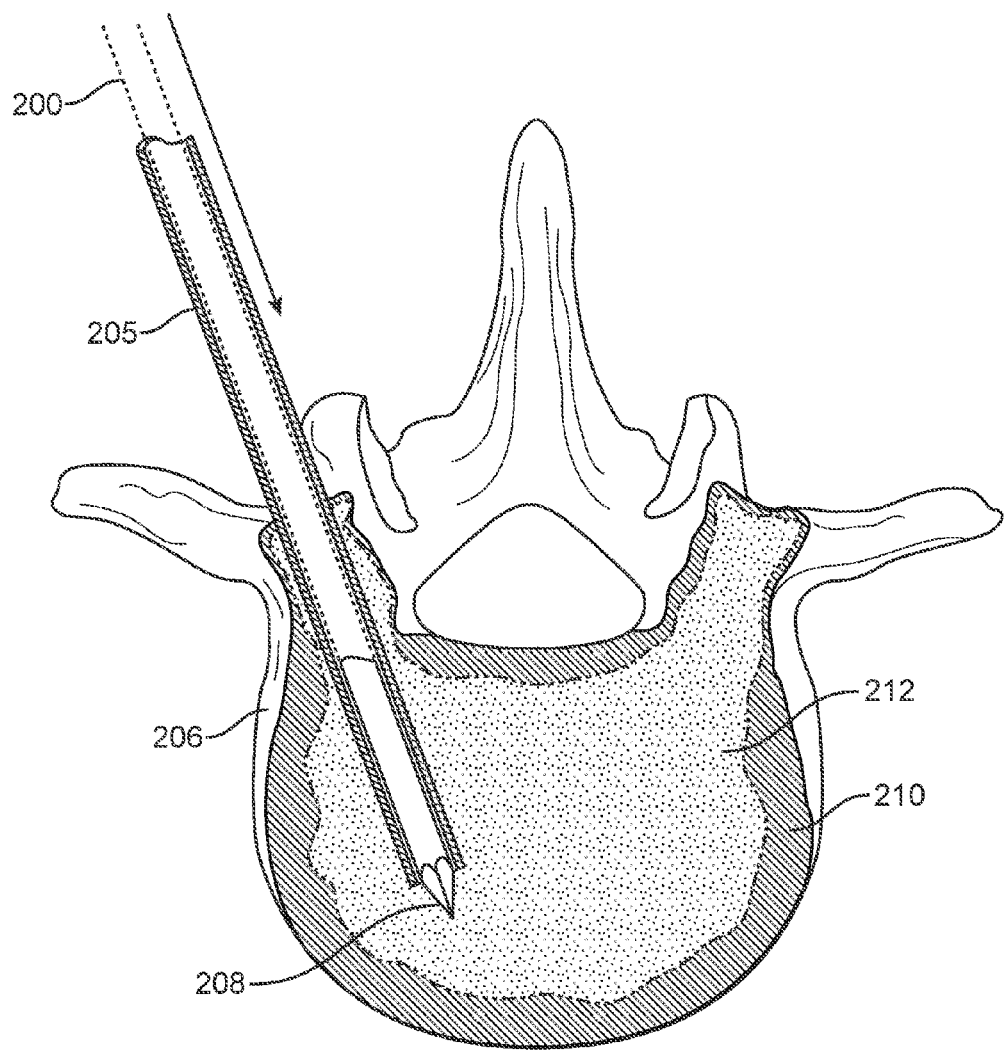
FIGS. 7A-7C are schematic sectional views of a method of use of the osteotome of FIG. 1.
Figure 7B:
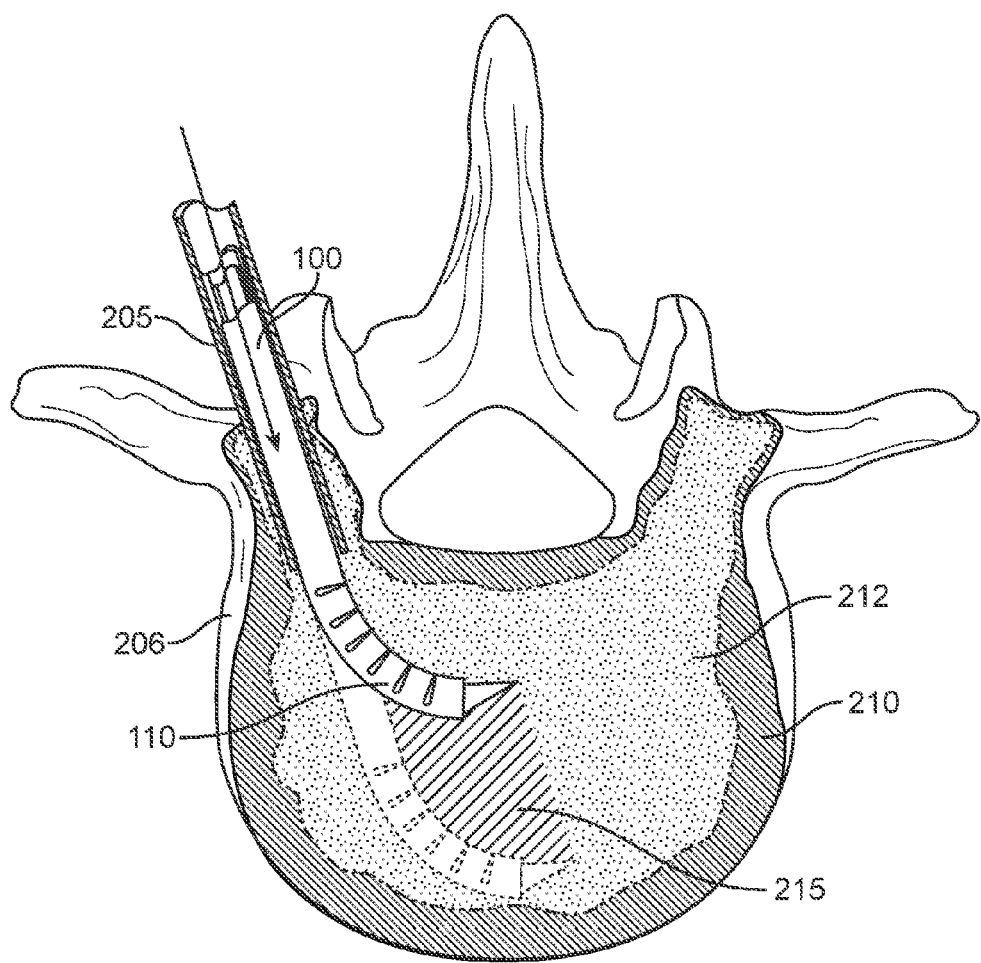
Figure 7C:
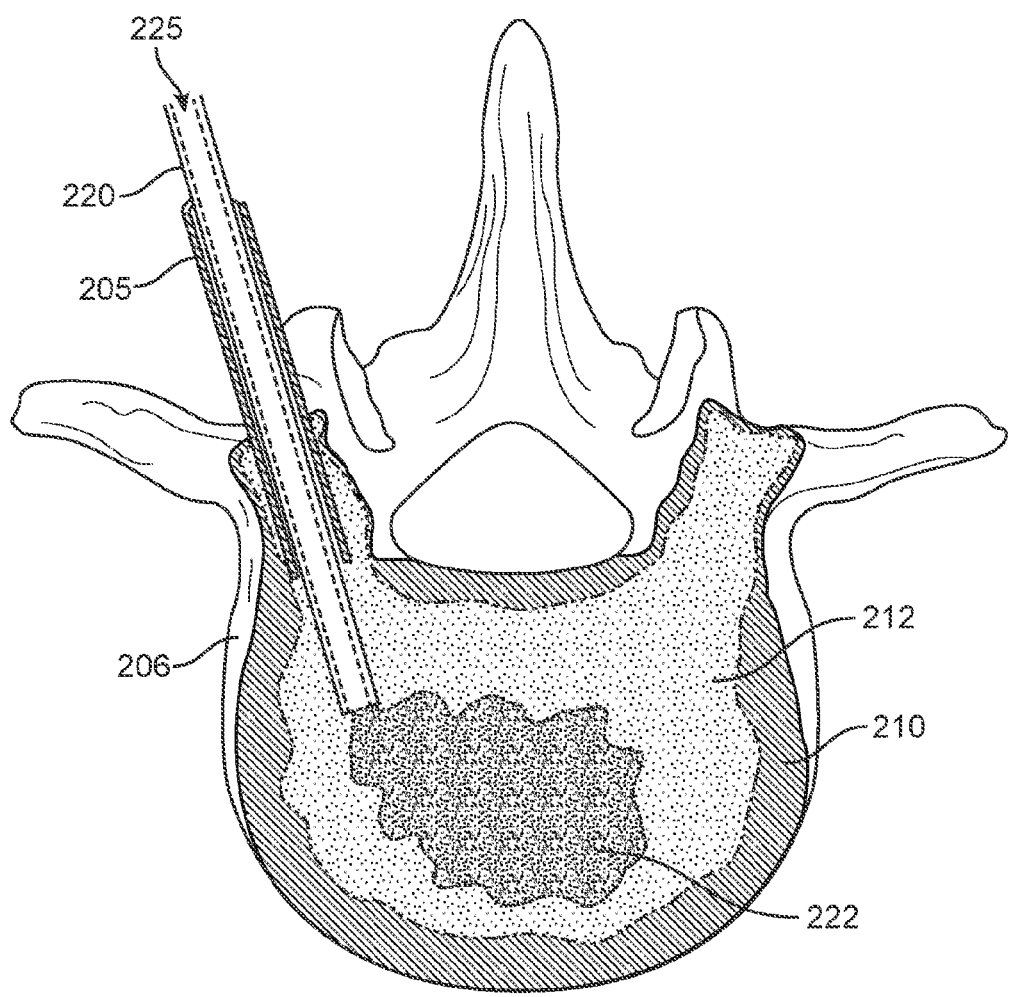

Referring to FIGS. 7A-7C, in one variation of use of the device, a physician taps or otherwise drives a stylet 200 and introducer sleeve 205 into a vertebral body 206 typically until the stylet tip 208 is within the anterior ⅓ of the vertebral body toward cortical bone 210 (FIG. 7A). Thereafter, the stylet 200 is removed and the sleeve 205 is moved proximally (FIG. 7B). As can be seen in FIG. 7B, the tool or osteotome 100 is inserted through the introducer sleeve 205 and articulated in a series of steps as described above. The working end 110 can be articulated intermittently while applying driving forces and optionally rotational forces to the handle 115 to advance the working, end through the cancellous bone 212 to create path or cavity 215. The tool is then tapped to further drive the working end 110 to, toward or past the midline of the vertebra. The physician can alternatively articulate the working end 110, and drive and rotate the working end further until imaging shows that the working end 110110 has created a cavity 215 of an optimal configuration. Thereafter, as depicted in FIG. 7C, the physician reverses the sequence and progressively straightens the working end 110 as the extension member is withdrawn from the vertebral body 206. Thereafter, the physician can insert a bone cement injector 220 into the path or cavity 215 created by osteotome 100. FIG. 7C illustrates a bone cement 222, for example a PMMA cement, being injected from a bone cement source 225.

In another embodiment (not shown), the apparatus 100 can have a handle 115 with a Luer fitting for coupling a bone cement syringe and the bone cement can be injected through the lumen 112 of the apparatus. In such an embodiment FIG. 9, the lumen can have a lubricious surface layer or polymeric lining 250 to insure least resistance to bone cement as it flows through the lumen. In one embodiment, the surface or lining 250 can be a fluorinated polymer such as TEFLON® or polytetrafluroethylene (PTFE). Other suitable fluoropolymer resins can be used such as FEP and PFA. Other materials also can be used such as FEP (Fluorinated ethylenepropylene), ECTFE (Ethylenechlorotrifluoro-ethylene), ETFE, Polyethylene, Polyamide, PVDF, Polyvinyl chloride and silicone. The scope of the invention can include providing a polymeric material having a static coefficient of friction of less than 0.5, less than 0.2 or less than 0.1.

Figure 9:
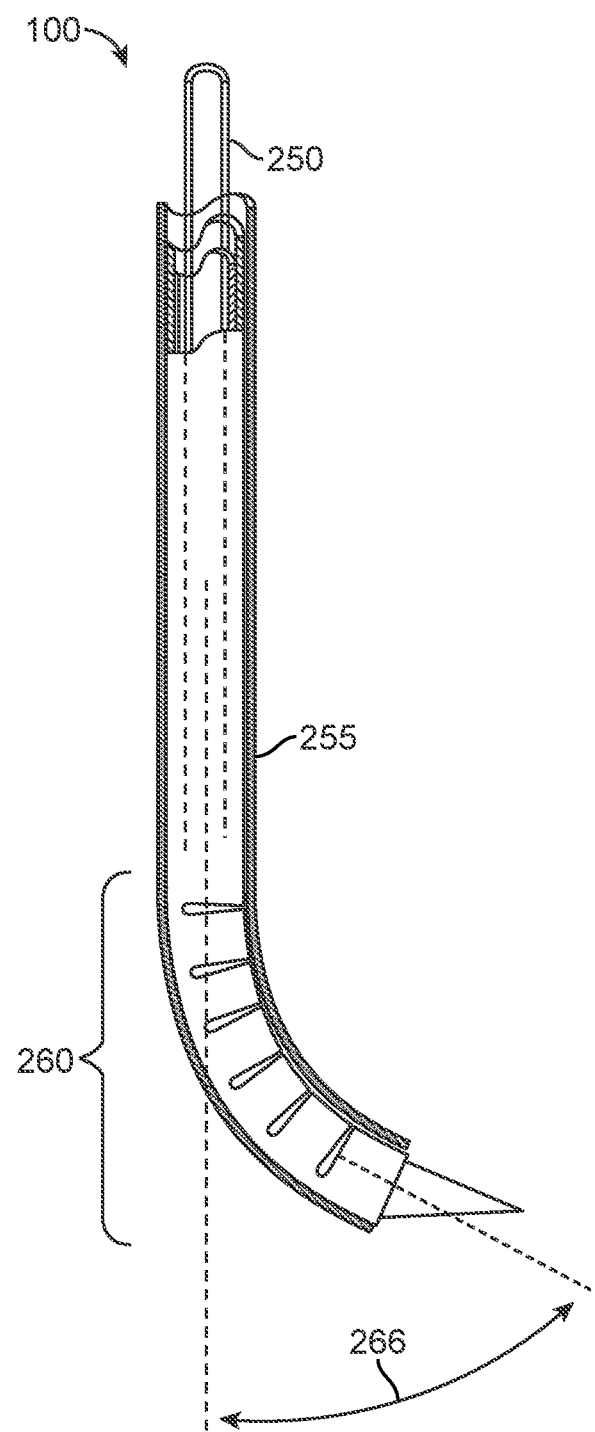
FIG. 9 is another embodiment of an osteotome working end.

FIG. 9 also shows the extension member or shaft 105 can be configured with an exterior flexible sleeve indicated at 255. The flexible sleeve can be any commonly known biocompatible material, for example, the sleeve can comprise any of the materials described in the preceding paragraph.

As also can be seen in FIG. 9, in one variation of the device 100, the working end 110 can be configured to deflect over a length indicated at 260 in a substantially smooth curve. The degree of articulation of the working end 110 can be at least 45°, 90°, 135° or at least 180° as indicated at 265 (FIG. 9). In additional variations, the slots of the outer 120 and inner sleeves 120 can be varied to produce a device having a radius of curvature that varies among the length 260 of the device 100.

In another embodiment of the invention, the inner sleeve can be spring loaded relative the outer sleeve, in such a way as to allow the working end to straighten under a selected level of force when pulled in a linear direction. This feature allows the physician to withdraw the assembly from the vertebral body partly or completely without further rotation the actuating portion 142 of handle 115. In some variations, the force-limiter can be provided to allow less than about 10 inch*lbs of force to be applied to bone.

Figure 8:
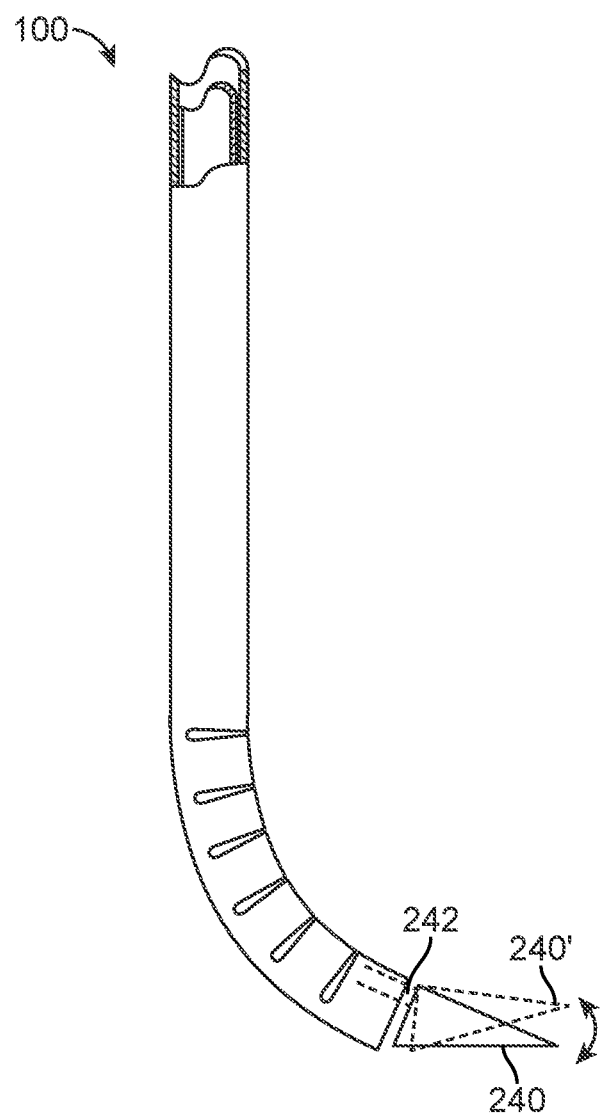
FIG. 8 is another embodiment of an osteotome working end.

In another embodiment shown in FIG. 8, the working end 110 is configured with a tip 240 that deflects to the position indicated at 240' when driven into bone. The tip 240 is coupled to the sleeve assembly by resilient member 242, for example a flexible metal such as stainless steel or NiTi. It has been found that the flexing of the tip 240 causes its distal surface area to engage cancellous bone which can assist in deflecting the working end 110 as it is hammered into bone.

In another embodiment of the invention (not shown), the actuator handle can include a secondary (or optional) mechanism for actuating the working end. The mechanism would include a hammer-able member with a ratchet such that each tap of the hammer would advance assembly and progressively actuate the working end into a curved configuration. A ratchet mechanism as known in the art would maintain the assembly in each of a plurality of articulated configurations. A release would be provided to allow for release of the ratchet to provide for straightening the extension member 105 for withdrawal from the vertebral body.

Figure 10:
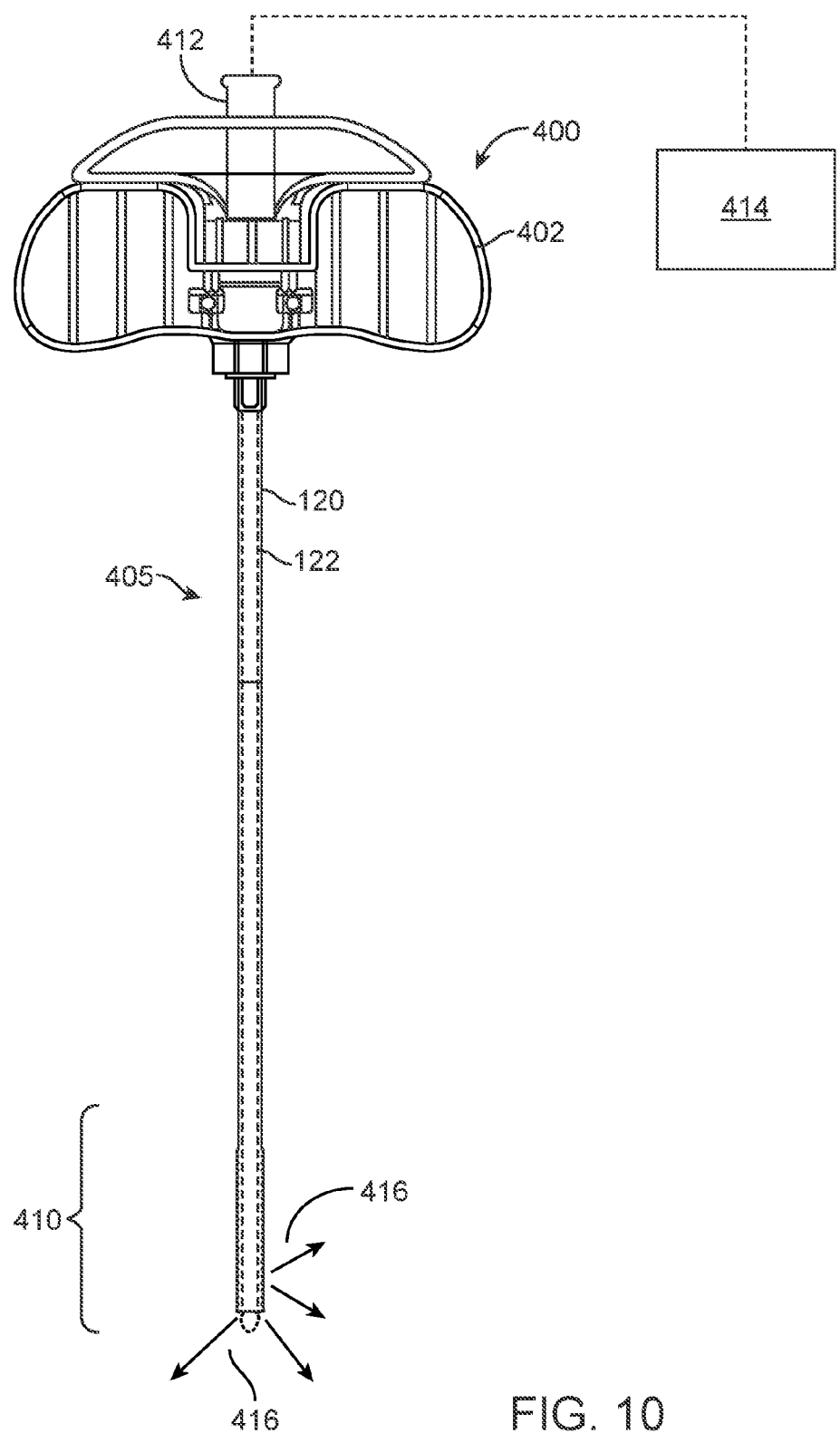
FIG. 10 is another variation of an osteotome with an outer sleeve.
Figure 11:
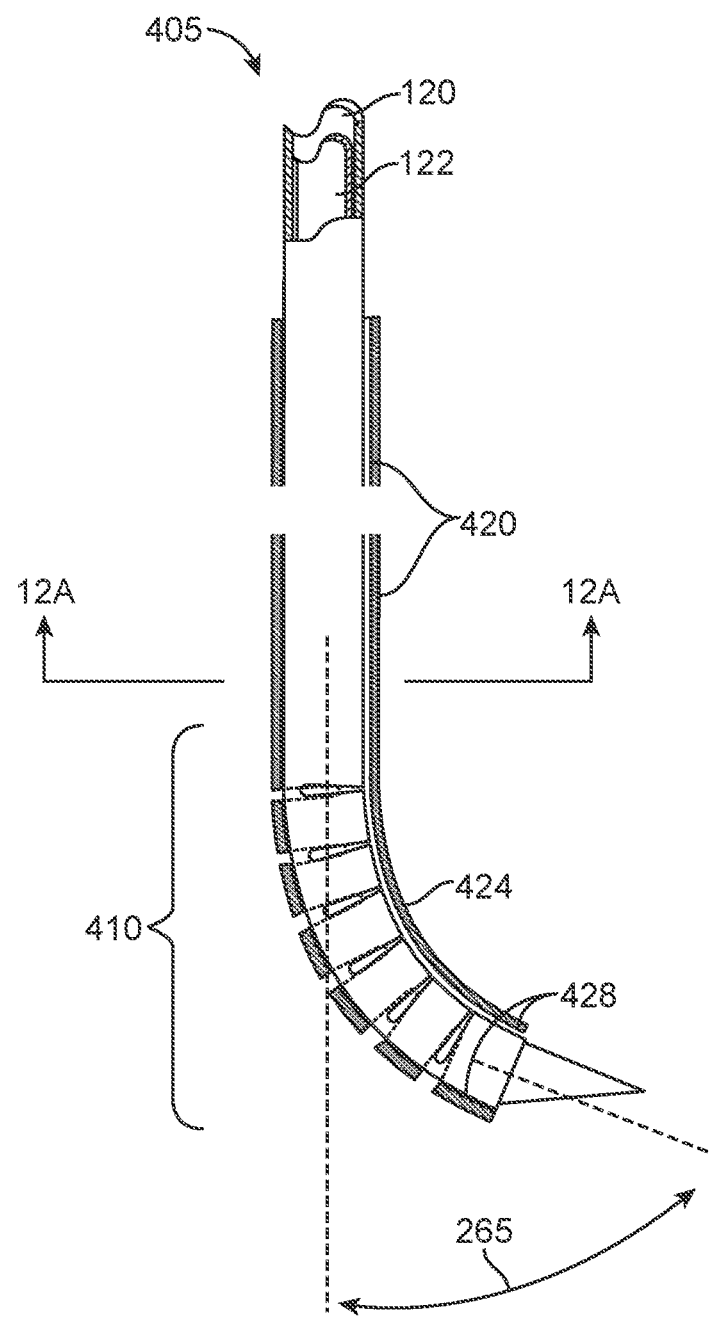
FIG. 11 is a cut-away view of the working end of the osteotome of FIG. 10.

FIGS. 10 and 11 illustrate another variation of a bone treatment device 400 with a handle 402 and extension member 405 extending to working end 410 having a similar construction to that FIGS. 1 to 6B. The device 400 operates as described previously with notched first (outer) sleeve 120 and cooperating notched second (inner) sleeve 122. However, the variation shown in FIGS. 10 and 11 also includes a third concentric notched sleeve 420, exterior to the first 120 and second 122 sleeves. The notches or slots in sleeve 420 at the working end 410 permit deflection of the sleeve as indicated at 265 in FIG. 11.

FIG. 10 also illustrates the treatment device 400 as including a luer fitting 412 that allows the device 402 to be coupled to a source of a filler material (e.g., a bone filler or bone cement material). The luer can be removable from the handle 402 to allow application of an impact force on the handle as described above. Moreover, the luer fitting 402 can be located on the actuating portion of the handle, the stationary part of the handle or even along the sleeve. In any case, variations of the device 400 permit coupling the filler material with a lumen extending through the sleeves (or between adjacent sleeves) to deposit filler material at the working end 410. As shown by arrows 416, filler material can be deposited through a distal end of the sleeves (where the sharp tip is solid) or can be deposited through openings in a side-wall of the sleeves. Clearly, variations of this configuration are within the scope of those familiar in the field.

In some variations, the third notched sleeve 420 is configured with its smooth (non-notched) surface 424 disposed to face inwardly on the articulated working end (FIG. 11) such that a solid surface forms the interior of the curved portion of the working end 410. The smooth surface 424 allows withdrawal of the device 100 into a cannula or introducer 205 without creating a risk that the slots or notches become caught on a cannula 205 (see e.g., FIG. 7B).

As shown in FIGS. 10-11, the third (outermost) sleeve 420 can extend from an intermediate location on the extension member 405 to a distal end of the working end 410. However, variations of the device include the third sleeve 420 extending to the handle 402. However, the third sleeve 420 is typically not coupled to the handle 402 so that any rotational force or torque generated by the handle 402 is not directly transmitted to the third sleeve 420.

In one variation, the third sleeve 420 is coupled to the second sleeve 120 at only one axial location. In the illustrated example shown in FIG. 11, the third sleeve 420 is affixed to second sleeve 420 by welds 428 at the distal end of the working end 410. However, the welds or other attachment means (e.g., a pin, key/keyway, protrusion, etc.) can be located on a medial part of the sleeve 420. The sleeve 420 can be fabricated of any bio-compatible material. For example, in one variation, the third sleeve is fabricated form a 3.00 mm diameter stainless steel material with a wall thickness of 0.007". The first, second and third sleeves are sized to have dimensions to allow a sliding fit between the sleeves.

Figure 12A:
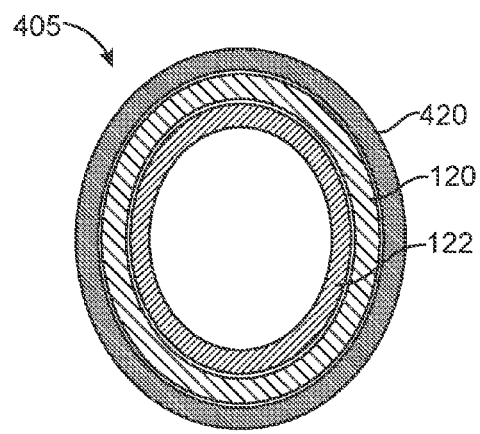
FIG. 12A is sectional view of another embodiment of working end, taken along line 12A-12A of FIG. 11.
Figure 12B:
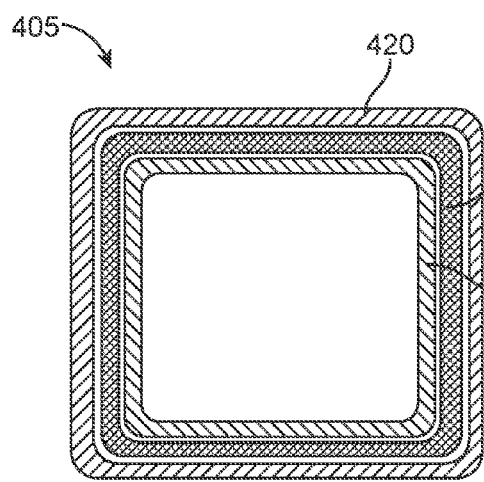
FIGS. 12B and 12C illustrate additional variations of preventing rotation between adjacent sleeves.
Figure 12C:
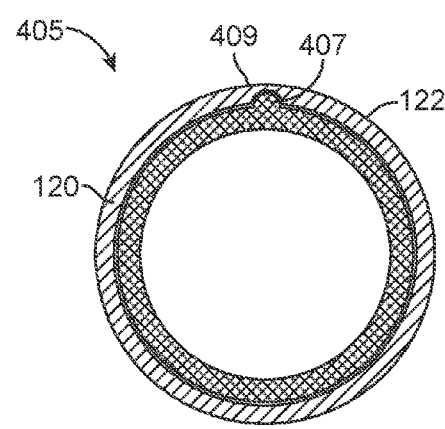

FIG. 12A is a sectional view of extension member 405 of another variation, similar to that shown in FIGS. 10-11. However, the variation depicted by FIG. 12A comprises non-round configurations of concentric slidable sleeves (double or triple sleeve devices). This configuration limits or prevents rotation between the sleeves and allows the physician to apply greater forces to the bone to create a cavity. While FIG. 12A illustrates an oval configuration, any non-round shape is within the scope of this disclosure. For example, the cross-sectional shape can comprise a square, polygonal, or other radially keyed configuration as shown in FIGS. 12B and 12C. As shown in FIG. 12C the sleeves can include a key 407 and a receiving keyway 409 to prevent rotation but allow relative or axial sliding of the sleeves. The key can comprise any protrusion or member that slides within a receiving keyway. Furthermore, the key can comprise a pin or any raised protrusion on an exterior or interior of a respective sleeve. In this illustration, only the first 122 and second 120 sleeves are illustrated. However, any of the sleeves can be configured with the key/keyway. Preventing rotation between sleeves improves the ability to apply force to bone at the articulated working end.

Figure 13:
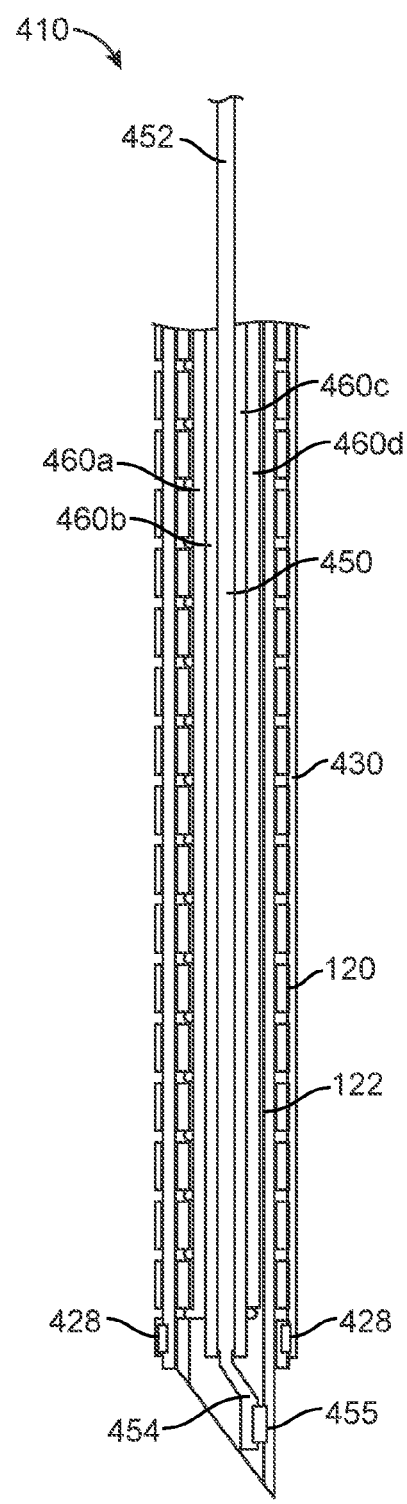
FIG. 13 is sectional view of another working end embodiment similar to that of FIG. 11.
Figure 14:
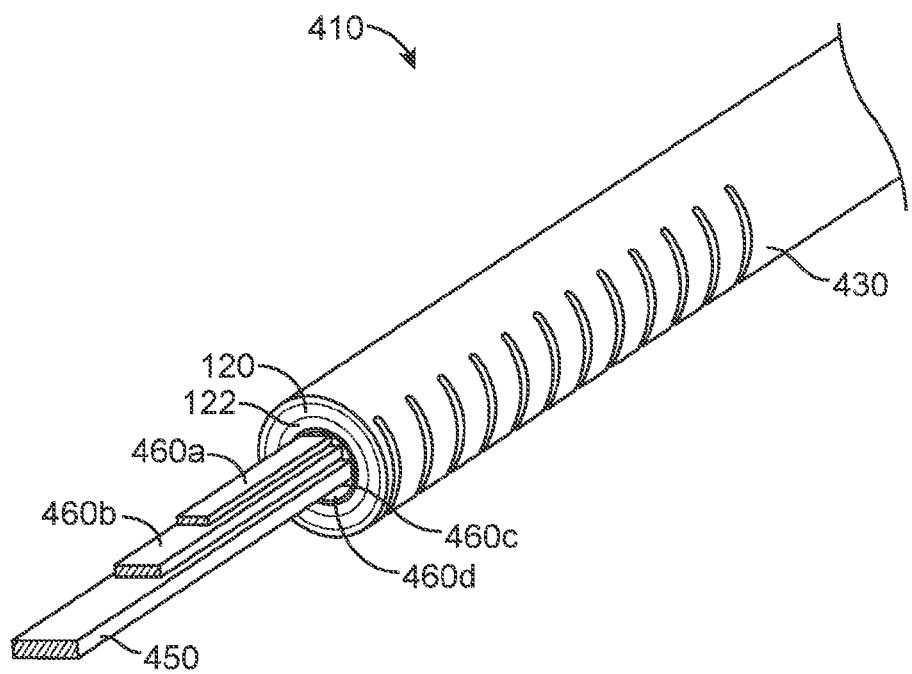
FIG. 14 is a cut-away perspective view of the working end of FIG. 13.

FIGS. 13-14 illustrate another variation of a working end 410 of an osteotome device. In this variation, the working end 410 includes one or more flat spring elements 450, 460a, 460b, 460c, 460d, that prevent relative rotation of the sleeves of the assembly thus allowing greater rotational forces to be applied to cancellous bone from an articulated working end. The spring elements further urge the working end assembly into a linear configuration. To articulate the sleeves, a rotational force is applied to the handle as described above, once this rotational force is removed, the spring elements ume the working end into a linear configuration. As shown in FIG. 13, one or more of the spring elements can extend through the sleeves for affixing to a handle to prevent rotation. Furthermore, the distal end 454 of flat spring element 450 is fixed to sleeve assembly by weld 455. Thus, the spring element is fixed at each end to prevent its rotation. Alternate variations include one or more spring elements being affixed to the inner sleeve assembly at a medial section of the sleeve.

As shown in FIGS. 13-14, variations of the osteotome can include any number of spring elements 460a-460d. These additional spring, elements 460a-460d can be welded at either a proximal or distal end thereof to an adjacent element or a sleeve to allow the element to function as a leaf spring.

Figure 15:
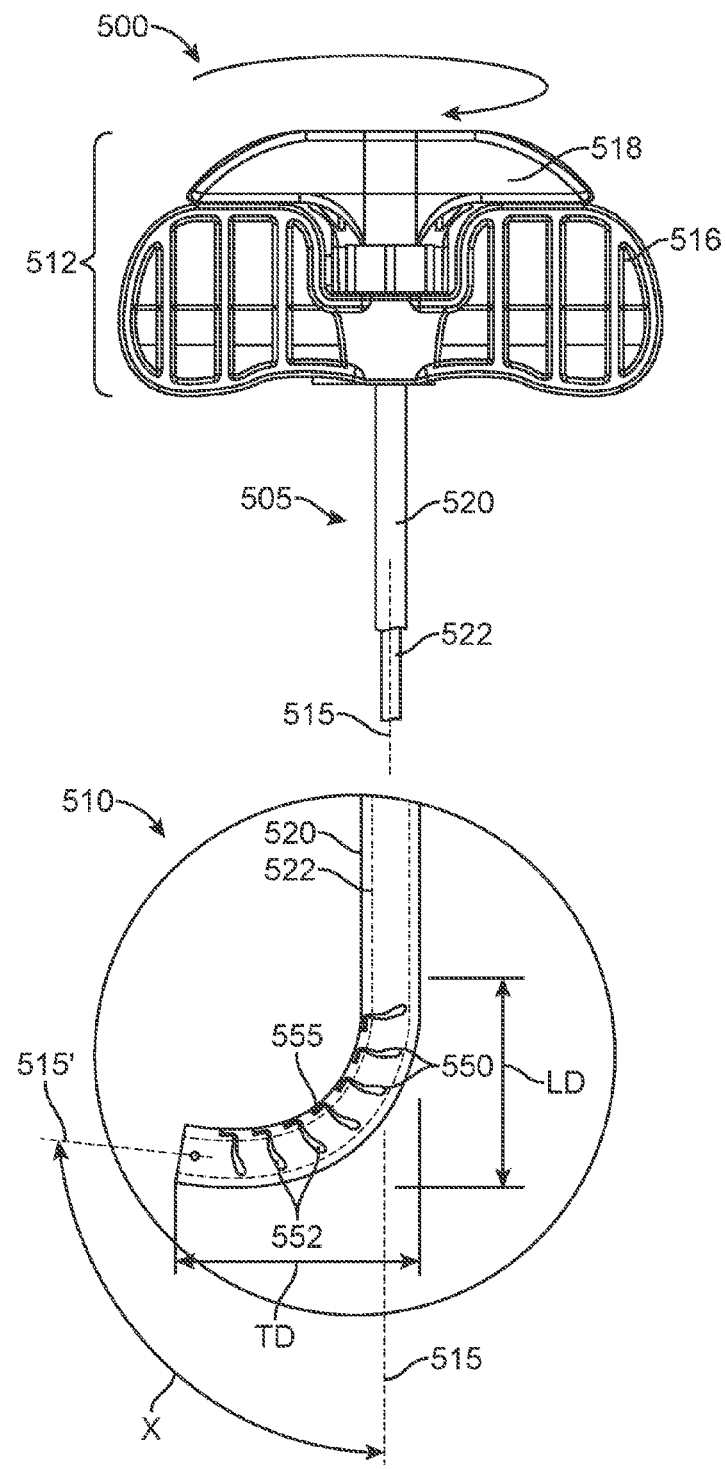
FIG. 15 illustrates another embodiment of an osteotome as described herein that has a distal working end that is configured for deformation resistance when used in very hard cancellous bone.
Figure 16:
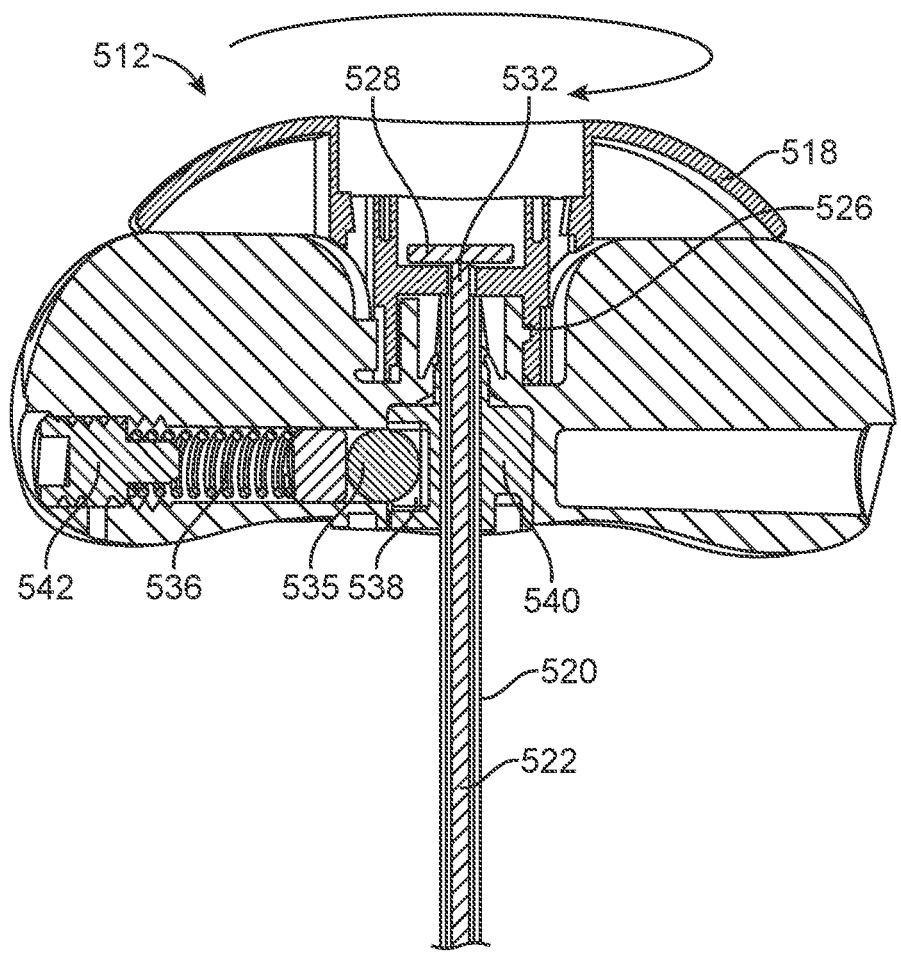
FIG. 16 illustrates an osteotome device as shown in FIG. 15 with a torque-limiting mechanism built into a handle portion.

FIGS. 15-16 illustrate another embodiment of an osteotome 500 with shaft assembly 505 having an articulating working end 510 that is designed to provide especially high strength and thus is adapted for use in dense, hard cancellous bone. In one aspect, the working end 510 exhibits high strength in applying high forces capable of displacing dense cancellous bone as the working end is moved from a linear insertion shape towards an articulated, non-linear shape. In a second aspect, the working end 510 exhibits high strength in resisting radial deformation when the articulated working end articulates to displace dense cancellous bone.

In FIG. 15, it can be seen that handle 512 is coupled to the shaft assembly 505 that extends about an indicated at 515. The first handle portion or body 516 and the rotatable actuator or second handle body 518 function as described in previous embodiments to articulate the working end 510 and axis 515 from a linear configuration to a curved configuration. FIGS. 15 and 16 show that the first handle body 516 is coupled to outer sleeve 520 of the shaft assembly 505 and the second handle body 518 is coupled to inner sleeve 522.

FIG. 16 is a sectional view of handle 512 again showing the mechanism for actuating the second inner sleeve 522 relative to the first outer sleeve 520, wherein the first and second handle bodies 516 and 518 are mated along a fast-lead helical thread 526. Thus, rotation of handle body 518 from about 45° to 90° will lift or translate the inner sleeve 522 axially relative to the outer sleeve 520 to articulate the working end 510. As can be seen in FIG. 16 the second handle body 518 engages flange 528 that is welded or otherwise joined to the proximal end 532 of inner sleeve 522. In this embodiment, a torque limiting, mechanism is provided in handle 512 which comprises a ball 535 that is urged by spring 536 into a detent 538 in metal collar 540 that is fixedly coupled to handle body 516. A set screw 542 is provided to adjust the force at which the torque-release mechanism will release under rotation of the handle. The re-settable torque release mechanism is set to release at a minimum of 8 inch*lbs of torque. In one embodiment, the release is set at 8 inch*lbs of torque, 10 inch*lbs of torque or 12 inch*lbs of torque.

In FIG. 15, it can be seen that the working end 510 is configured with a series of slots 550 in the first and second sleeves 520 and 522 that allow for articulation of the assembly. The slots 550 are provided in both sleeves and can range in number from about 5 to 20. However, additional variations of the device can include any number of slots in either sleeve. This variation also illustrates slots that have an arcuate configuration rather than being a simple radial slot is shown in previous embodiments. In one variation, the slots 550 each have a first radial slot portion 552 that extends substantially radially about a sleeve 520 or 522 and a second axial slot portion 555 that extends substantially axially in a sleeve 520 or 522.

Figure 17:
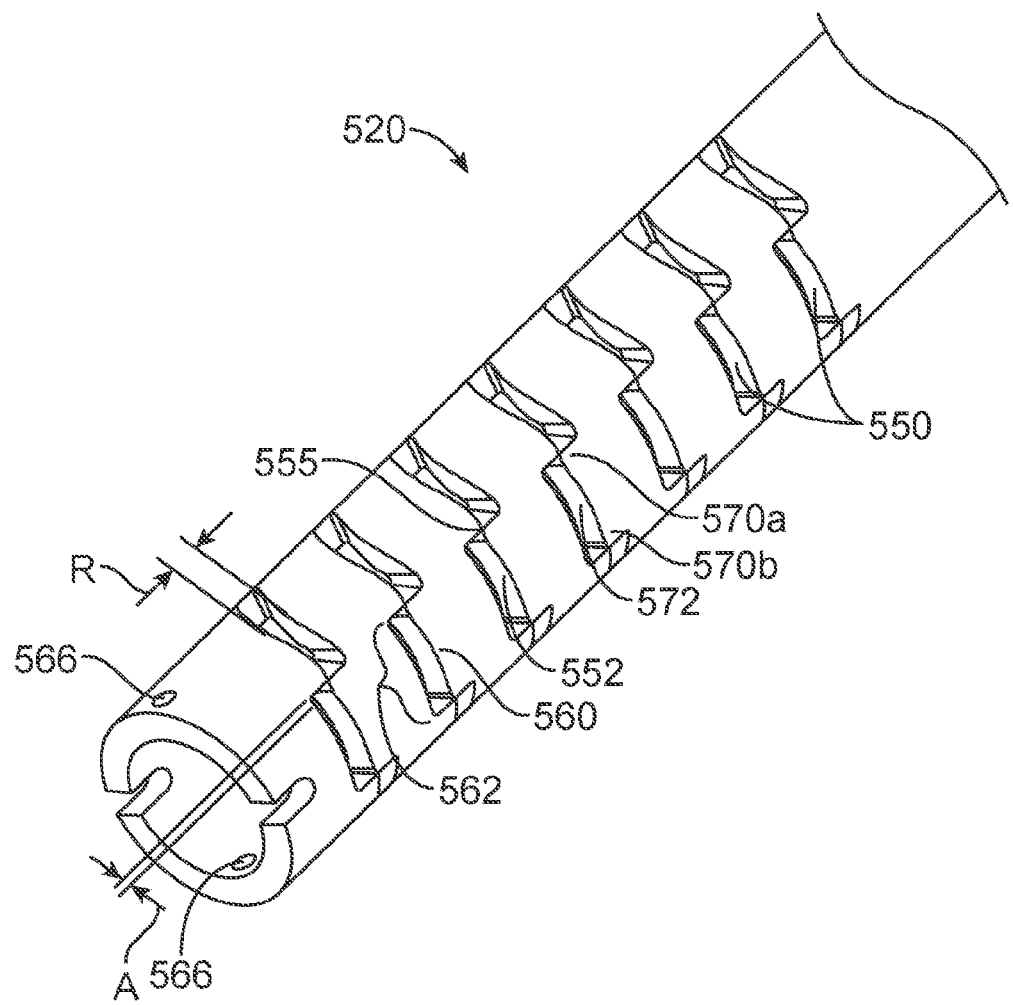
FIG. 17 illustrates a de-mated slotted sleeve of the device of FIG. 15 wherein the slots are configured to resist radial deformation of the working end when articulated.
Figure 18A:
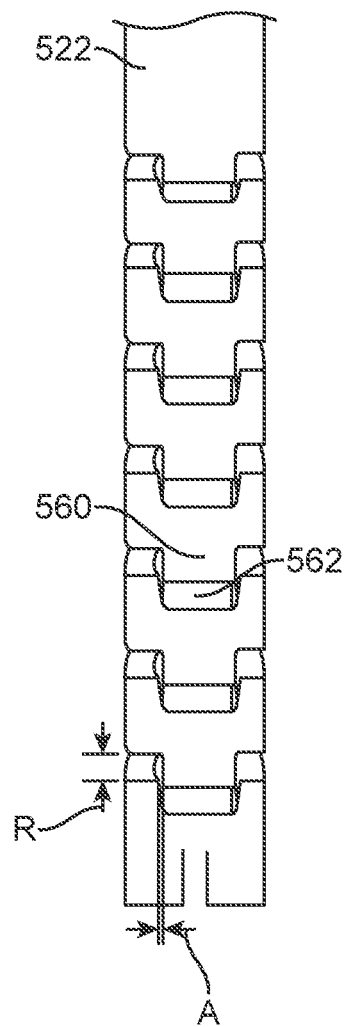
FIGS. 18A and 18B illustrate first and second concentric slotted sleeves of the device of FIG. 15 from different sides to illustrate the configuration of the slots.
Figure 18B:
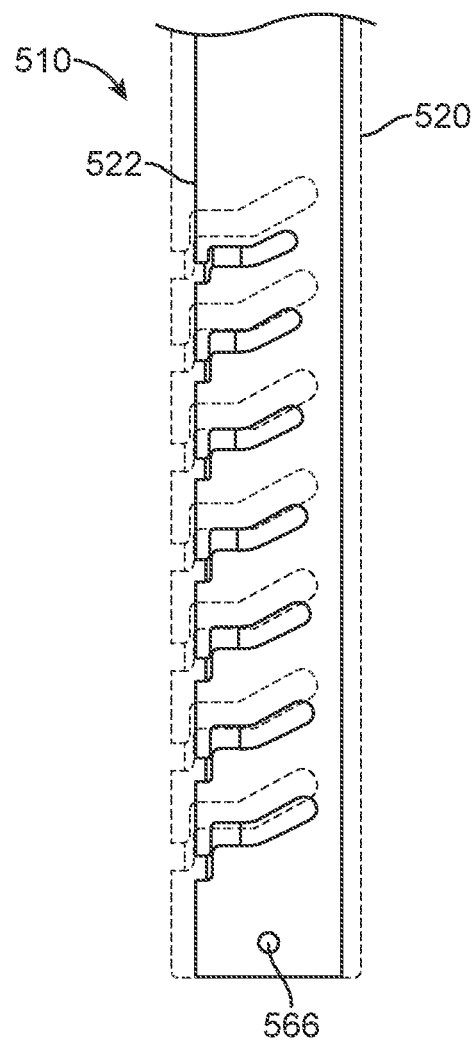
Figure 18C:
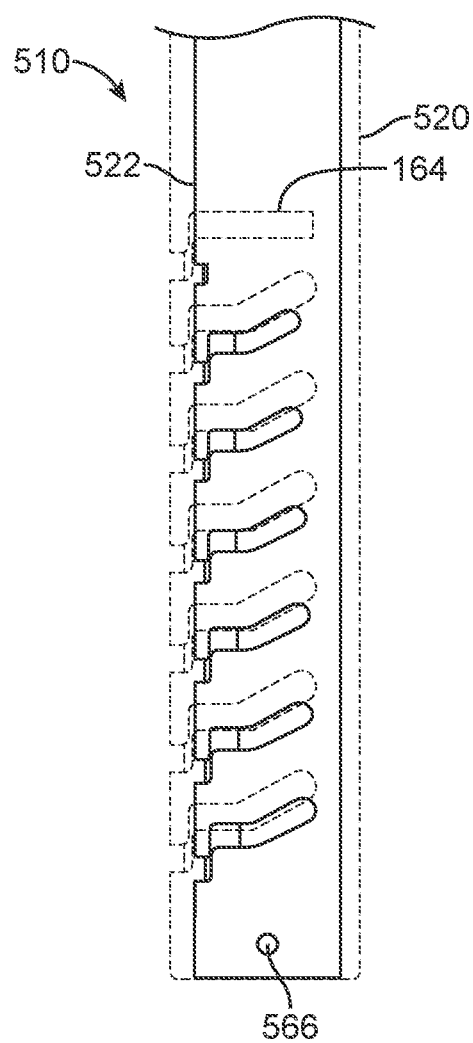
FIG. 18C illustrates a sleeve configuration with arcuate slots and a radial slot.

FIG. 17 shows an outer sleeve 520 de-mated from the shaft assembly 505 to more particularly depict the dimensions and features of arcuate slots 550. In this variation, the arcuate slots 550 are also configured as a 'keyed' or interlocking features wherein one slot edge comprises a projecting 'key' element 560 that slides into and engages a key-receiving shape 562 of the opposing slot edge when the sleeve is articulated. Thus, the interlocking projecting and receiving features 560 and 562 provide the shaft assembly 505 with significantly increased strength in resisting deformation when the working end is rotated in dense cancellous bone. The arcuate slots 550 as depicted in FIG. 17 can be provided in either the outer sleeve 520, the inner sleeve 522 or both sleeves, Also, either or both sleeves can include any combination of arcuate and radial slots in the same sleeve. Alternatively, a cooperating sleeve without the arcuate slots 550 of HG. 17 can have radially-oriented slots as described in earlier embodiments. The radial oriented slots, as shown previously, comprise slots that extend about a portion of the circumference, of the sleeve. Where each radial oriented slot is typically within a plane is perpendicular to an axis of the sleeve (when straight). An arcuate slot, also is located about a portion of the circumference of the sleeve but is not limited to within a plane that is perpendicular to an axis of the sleeve. As shown in FIG. 18B, the arcuate slots are angled when viewed from a side of the device, In certain additional variations, a sleeve can include both arcuate slots and radial slots as shown in FIG. 18C. The arcuate shaped slots can also be referred to as axial oriented slots as the direction of the slot is parallel or angled from an axis of the sleeve while a radial oriented slot is perpendicular to an axis of the sleeve. Such a combination of slots can be provided on any sleeve (an inner sleeve, an outer sleeve, or both sleeves). In alternate variations, the device can be configured to deflect in a torsional, slightly helical, or non-planar articulated configuration. In such a case, each adjacent slot will be radially offset along a length of the device.

FIG. 18B is a plan view of inner sleeve 522 de-mated from shaft assembly 505 and again shows the arcuate slots 550 with interlocking projecting and receiving features 560 and 562, In FIG. 18B, it can be seen that on shaft assembly 505 includes arcuate slots 550 in both sleeves. The slot can be aligned or non-aligned when the working end is in a linear position. The distal ends of the shafts can be coupled together by a press-fit pins inserted into holes 566 in the sleeves (FIG. 17) or by any other suitable fastening. means such as welding.

Figure 21:
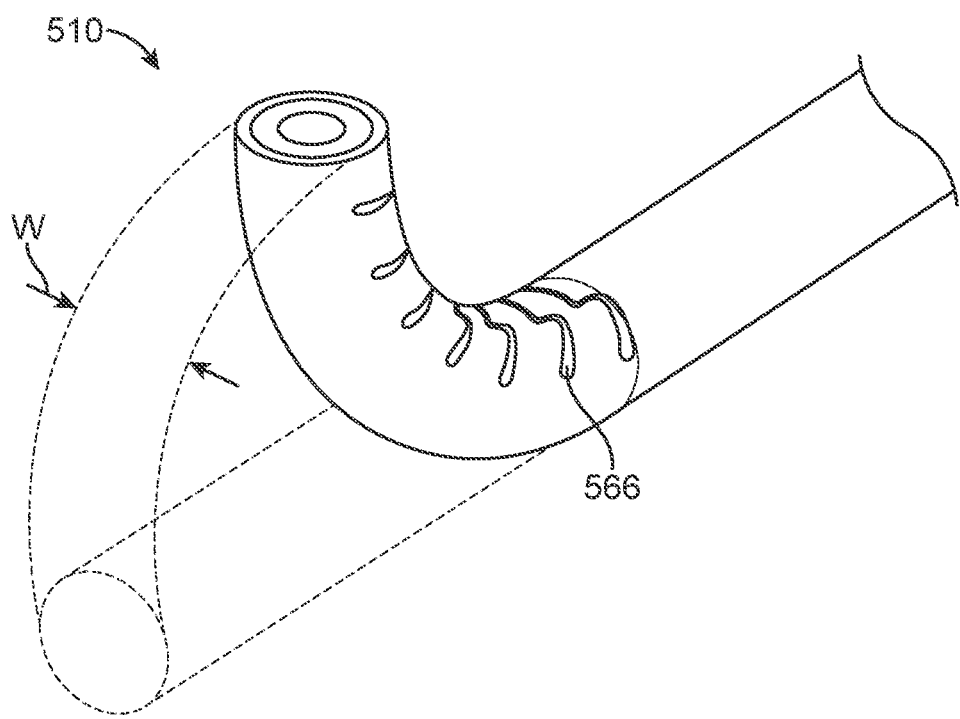
FIG. 21 is a view of the working end of FIGS. 15 and 19A-19C illustrating the width and volume of displaced cancellous bone caused by articulation of the working end.

In another aspect of the invention best seen in FIGS. 17 and 18B, the arcuate slots 550 have a varied width, again for providing greater resistance to torsional, twisting or radial deformation when in use. in one embodiment, the slot width A on the axially-extending slot portions 555 along the sides 570 a and 570 b of the projecting feature 560 is less than the slot width R on the radial-extending slot portion 552 adjacent the end surface 572 of projecting feature 560. Referring to FIGS. 18A, 18B and 21, it can be understood how the keyed featured 560 and 562 will mesh and interlock when the working end is articulated and thus resist deformation under twisting loads, In one embodiment, the axial slot portions 555 have a width A of less than 0.010", 008" or 0.006". In such an embodiment, the said radial slot portions 552 have a width R that greater than 0.006", 008" or 0.010". Such slot can be cut by a laser cutter as is known in the art.

Referring back to FIG. 15, the working end 510 is adapted for providing a sharp, tight radius curvature which is desirable in an osteotome 500 used in a vertebral body. In one embodiment, the transverse dimension TD of the working end 510 in the fully articulated position is at least 10 mm. Further, the working end 510 is capable of articulation such that the linear axis 515 is deflected at least 90° to axis 515' as depicted in FIG. 15. In one embodiment, the deflectable shaft portion has a length dimension LD of 12 mm or less in its linear shape (FIG. 15) and is capable of articulation to provide a maximum transverse dimension TD of at least 10 mm and further articulate the axis 515 at least 90°. In general, the working end has a deflectable shaft portion that provides a ratio of at least 0.8:1 of the maximum transverse dimension TD relative to the length dimension LD of the deflecting shaft portion.

Figure 19A:
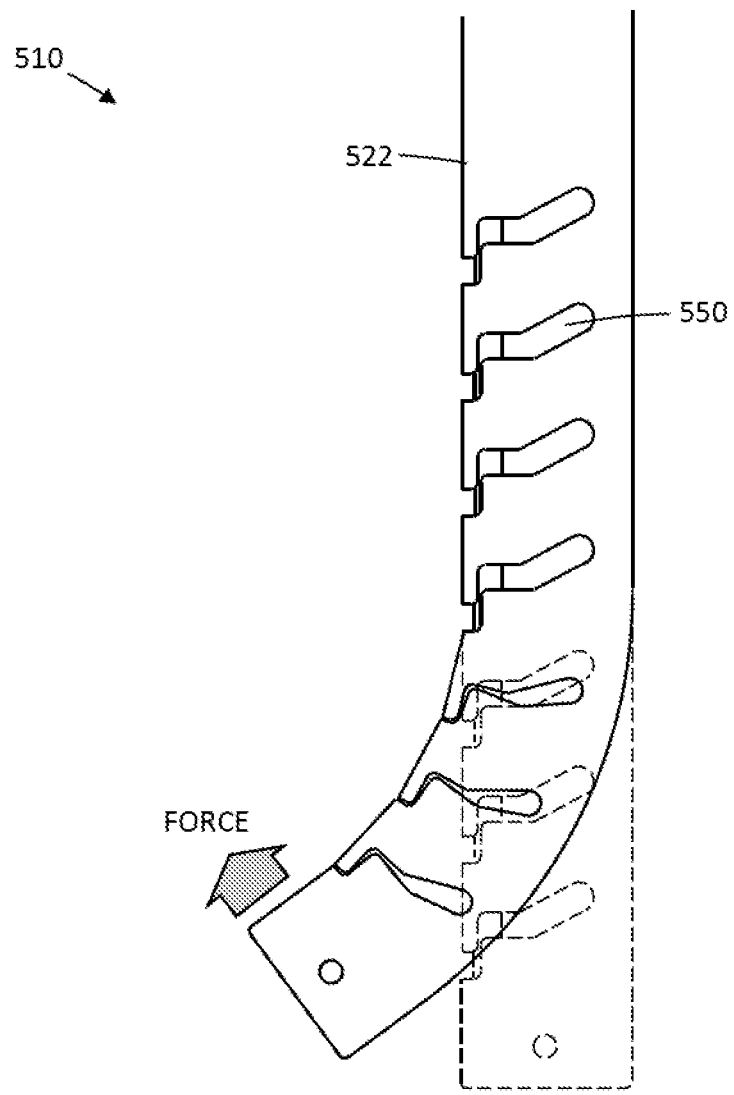
FIGS. 19A-19C are enlarged schematic views the working end of the osteotome of FIG. 15 illustrating the progressive application of force would be applied by the working end to cancellous bone, wherein the force application progresses over different axial portions of the working end as it articulates.
Figure 19B:
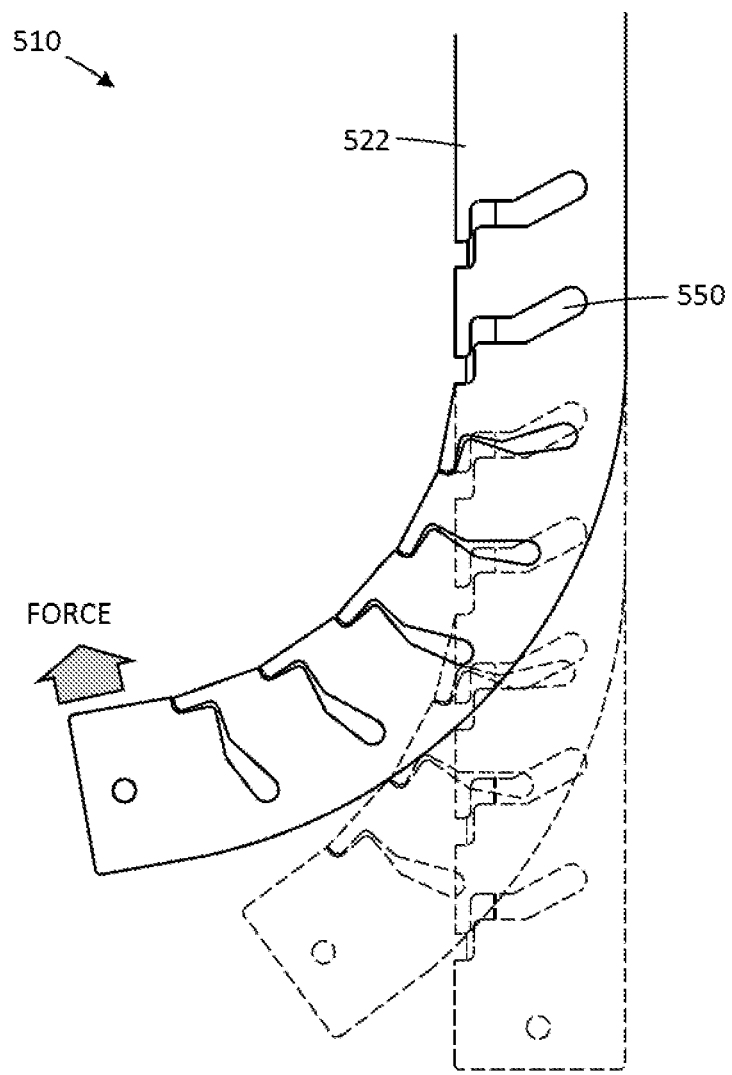
Figure 19C:
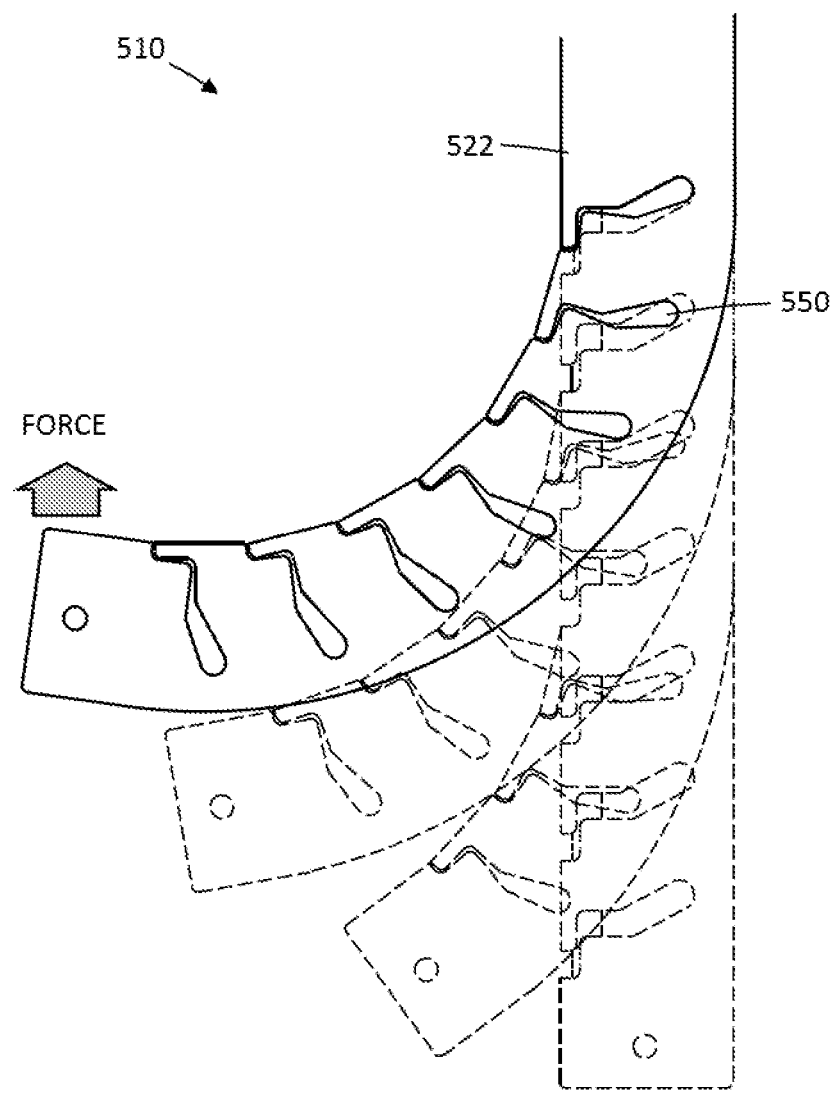

Now referring to FIGS. 19A-19C, another aspect of the invention relates to the level of forces that can be applied to bone when articulating the working end 510, without regard to rotation of the articulated working end. In one embodiment as depicted in FIGS. 15-19C, movement of the working end toward the articulated configuration can apply at least 30 lbs. force to cancellous bone, or at least 50 lbs. force to bone or at least 70 lbs. force to bone. Still referring to FIGS. 19A-19C, another aspect of the invention relates to the manner is which forces are applied to bone when the working end is progressively articulated and in which there is not single hinge point around which the working end pivots. As the plurality of slots close together, they do so in a sequential manner to progressively articulate the working end. FIGS. 19A-19C illustrate that maximum forces are applied at the distal tip of the device in a progressive manner as first the most distal portion of the shaft articulates, then an adjacent proximal portion of the shaft articulated an so forth. This aspect of the working end differs greatly from the prior art stylet device and working end 580 of FIGS. 20A-20B, wherein the stylet tip 582 is actuated by pull rod 584 which caused the tip 582 to swing around a single pivot point 585 which thus loads the entire elongated surface 588 of the stylet tip 582. It can be understood that device of FIGS. 19A-19C which provide a progressive, sequential application of force over discrete articulating portions can displace cancellous bone far more effectively with a small diameter tool than hinge-type device as in FIG. 20B which cannot apply forces progressively and sequentially over the articulating surface.

FIG. 21 depicts another aspect of the invention wherein it can be seen that working end 510 can be progressively articulated to displace a path in cancellous bone having a width W. In other words, the width W is equal to the diameter of the working end 510. In contrast, the prior art device of FIG. 20B can typically only displace a path in cancellous bone having a width X, which is less that the diameter of the tool.

Figure 20A:
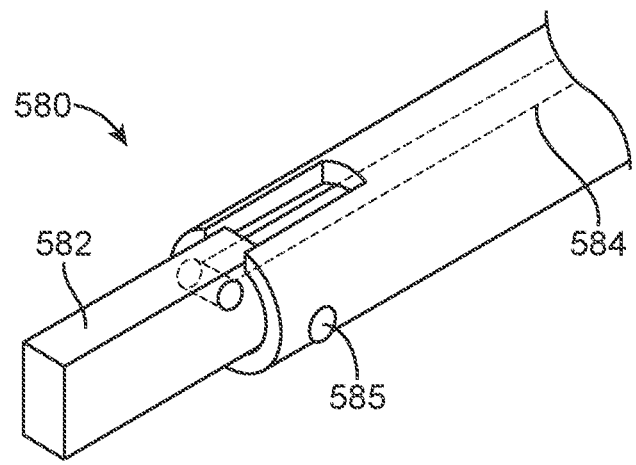
FIGS. 20A-20B show the distal end of a prior art stylet with a hinged distal tip that is used to treat cancellous bone.
Figure 20B:
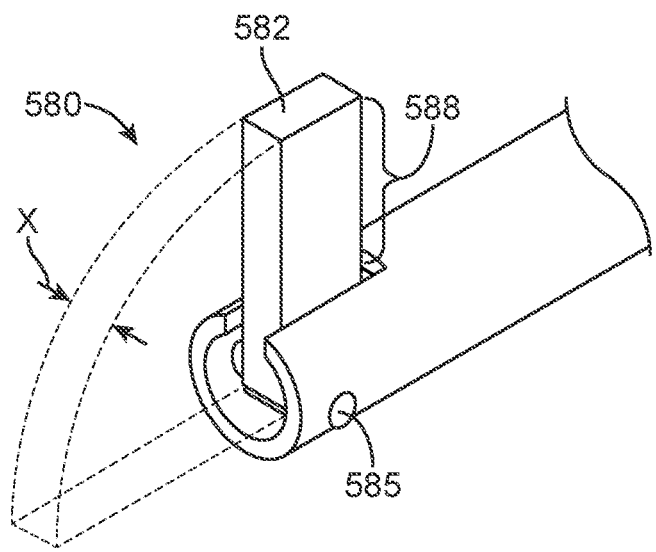
Figures 22, 23:
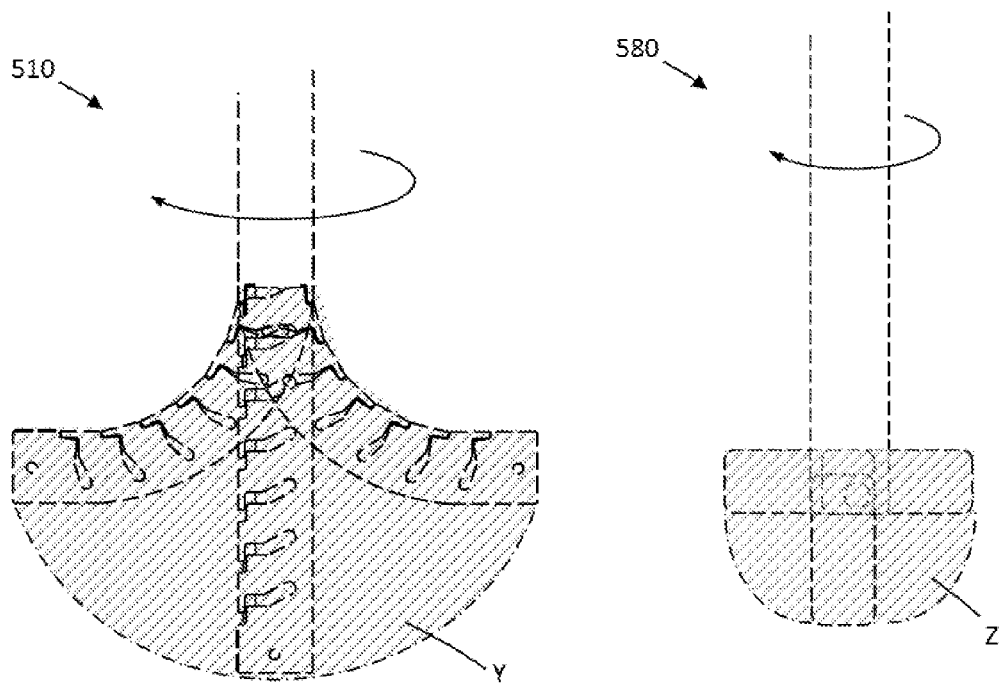
FIG. 22 is a view of the working end of FIGS. 15 and 19A-19C illustrating the volume of displaced cancellous bone caused by articulation and rotation of the working end.
FIG. 23 is a view of the prior art stylet working end of FIGS. 20A-20B depicting the limited volume of cancellous bone that ca be displaced by articulation and rotation of the prior art device.

FIGS. 22 and 23 illustrate another aspect of the invention wherein the working end when rotated can displace a much greater volume of cancellous bone that the prior art device of FIGS. 20A-20B. In FIG. 22, it can be seen that rotation of working 510 as it is articulated can great a very large displaced volume Y of cancellous bone compared to the volume Z that could potentially be displaced by the working end 580 of FIGS. 20A-20B.

Figure 24A:
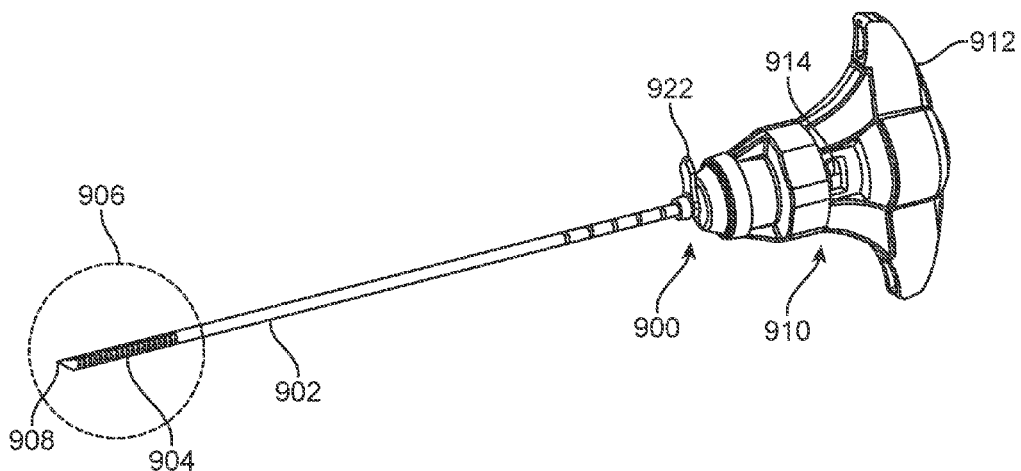
FIG. 24A illustrates another variation of an articulating device.

FIG. 24A illustrates another variation of a device 900 having a shaft 902 with a working end 906 with a sharp tip 908. As illustrated the device 900 includes an articulating portion 904 at the working end 906. The device can also include a handle 910 with an actuating portion or member 912 that causes articulation of the working end 906. The handle can include a window 914 to permit a physician to indirectly observe the degree of articulation of the working end. The features of the handle 910 are described further below.

As discussed herein the device 900 is designed to provide especially high strength and thus is adapted for use in dense, hard cancellous bone as well as other tissue including soft tissue, compacted tissue, tumors, or other regions the body with varying density. In one aspect, the working end 906 exhibits high strength in applying high forces capable of displacing dense tissue as the working. end is moved from a linear insertion shape towards an articulated, non-linear shape. The variation of the device 900 shown in FIG. 24A includes additional features to produce high strength in resisting radial deformation when the articulated working end articulates to displace dense tissue as well as increased strength when articulated. The features can also increase a fatigue strength of the device.

Figure 24B:
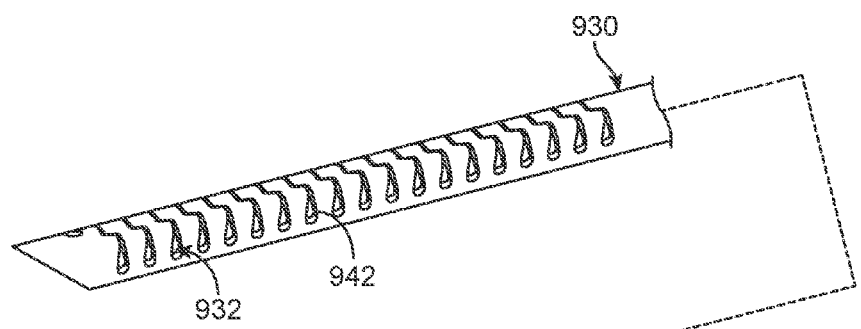
FIGS. 24B-24C respectively illustrate an outer sleeve and an inner sleeve that form the shaft of the device of FIG. 24A.
Figure 24C:
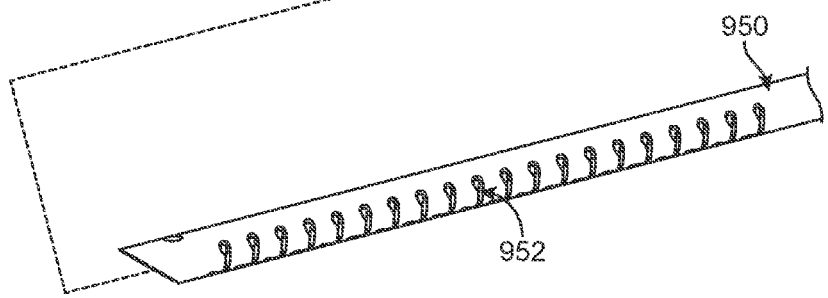

FIGS. 24B and 24C respectively illustrate an outer sleeve 930 and an inner sleeve 950 that form the shaft 902. In certain variations the shaft can comprise a single sleeve (e.g. an outer sleeve 930) alone. Alternatively, the shaft 902 can comprise three or more nested sleeves. As shown, outer sleeve 930 includes a first plurality of keyed slots 932 to permit articulation of the sleeve. The inner sleeve 950 includes a second plurality of keyed slots 952 where the second plurality of keyed slots 952 can be rotationally offset from the first plurality of keyed slots 952. In addition, in the variations shown, the sleeves can comprise solid or continuous tubes where the keyed slots are opposite to a continuous section of material. Such a configuration increases the strength of the device when used to displace tissue in an articulated configuration. However, additional variations of the device can include sleeves formed from assembled components that form the keyed slot configuration.

Figure 25A:
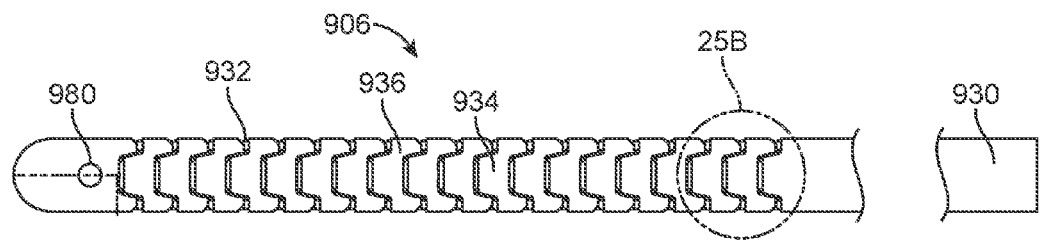
FIG. 25A illustrates a top view of the working end of the device shown in FIG. 24A.
Figure 25B:
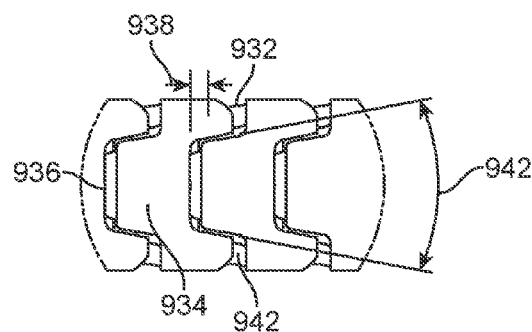
FIG. 25B, which comprises a magnified section of the area 25B in FIG. 25A.

FIG. 25A illustrates a top view of the working end 906 of the device 900 shown in FIG. 24A. Specifically, the outer sleeve 930 is shown having a plurality of keyed slots 932 extending along a portion of the sleeve 930. Rather than being parallel, the edges of the keyed slots are formed into keyed portions 934 and key receiving portions 936. As noted above, the keyed slots 932 extend in a depth-wise manner as shown below. In this variation, as shown in FIG. 25B, which comprises a magnified section of the area 25B in FIG. 25A, the keyed slots 932 are separated by a gap 938 when the shaft is in the linear configuration and also include a taper angle 942 where the keyed portions 934 and key receiving portions 936 are each tapered. This taper allows for a fit between the keyed portion 934 and the key receiving portion 936 that minimizes clearance between the two edges when nested together. Such a taper also permits increased surface area contact between the face of the keyed portion 934 as well as the lateral tapered sides. The sides of the keyed slots 932 are cut to provide a clearance gap 942 (see FIG. 24B) which provide clearance to permit bending of the sleeve 930. The keyed slots 932 can be configured such that the clearance gap 942 remains separated or closes upon articulation of the sleeve 930.

Figure 25C:
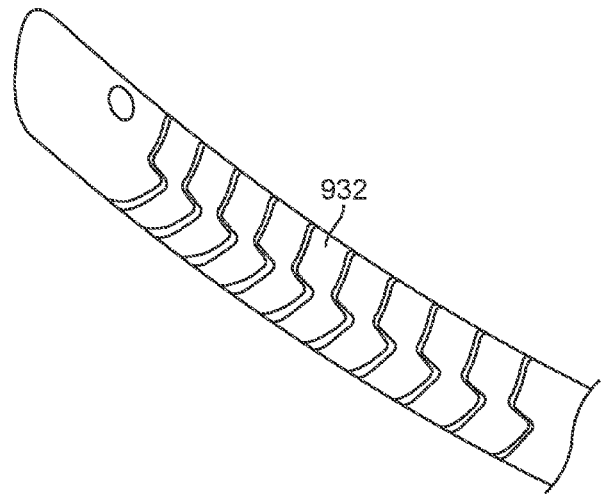
FIG. 25C shows the shaft of FIG. 25A in a partially articulated configuration.

To articulate the shaft, as disclosed herein, the actuating member of the handle of the device can apply a compressive force to the sleeve 930. This compressive force causes the keyed portion 934 and key receiving portion 936 to join or nest together and form a contiguous or near contiguous surface. Where such a contiguous surface is not possible without the taper angle. The contiguous surface increases the contact area between the keyed portion 934 and key receiving portion 936 when nested together and improves the torsional resistance of the shaft when articulated. FIG. 25C illustrates a working end of a shaft in a partially articulated configuration where the keyed portions begin to nest within the key receiving portions 936 where full articulation would cause formation of the contiguous surface. In the illustrated variation, the taper angle 942 is the same for each of the keyed slots 932. However, variations of the device can include a shaft or sleeve with a plurality of series of keyed slots 932 with series of keyed slots having different taper angles as well as a combination of keyed slots and un-keyed slots as disclosed above.

Figure 25D:
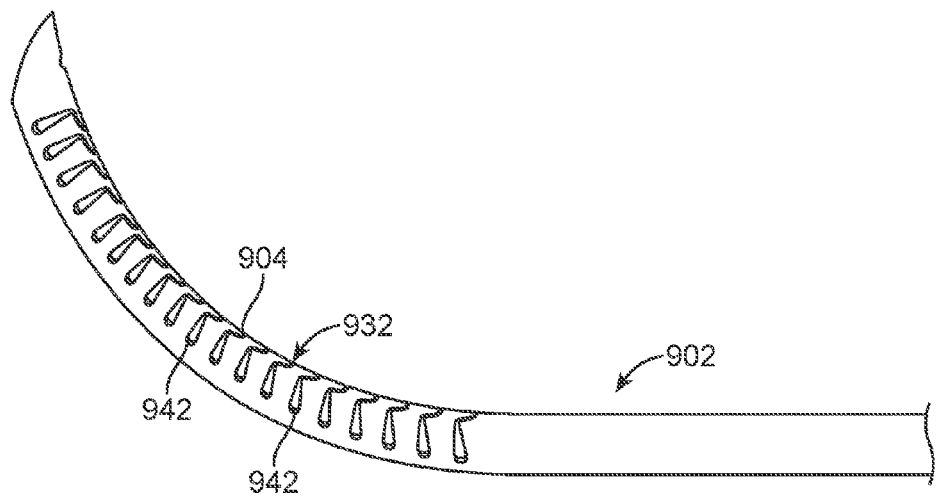
FIGS. 25D-25E illustrate a shaft in a fully articulated configuration and a reverse articulated configuration.
Figure 25E:
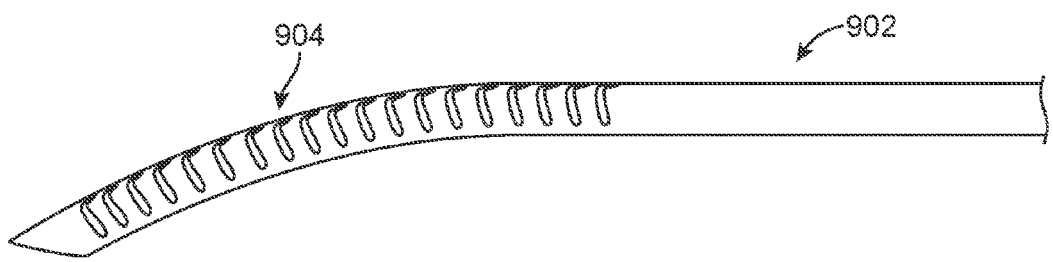

FIG. 25D illustrates a side view of a working end of a shaft 902 in a fully articulated position (where the shaft includes the inner 930 and outer 950 sleeves). Variations of the device can be configured to have more or less of an articulation angle. As shown, keyed portion and the key receiving portion the keyed slots 932 join together while clearance gap 942 at the side of the slots 932 remains separated. FIG. 25E illustrates a variation of the device where the articulating section 904 of the shaft can straighten from the articulated configuration shown in FIG. 25D and continue to reverse and articulate, at least partially, in an opposite direction. Partial reversal of the articulating section 904 can assist the physician in removing the device from hard tissue by allowing the device to fully return to the linear configuration shown in FIG. 24A. As noted above, in certain variations of the device, the surface of each sleeve opposite to the slots is continuous and articulation of the sleeve occurs with plastic deformation of the continuous portion. The ability to partially articulate the articulating section in a reverse direction counter the plastic deformation effect of the continuous section of the sleeves (the side of the sleeve opposite to the slots) which allows for the shaft to ultimately return to a linear configuration and removed from the target site. In addition, the amount of articulation or reverse articulation can be configured based on the slot design.

Figure 26A:
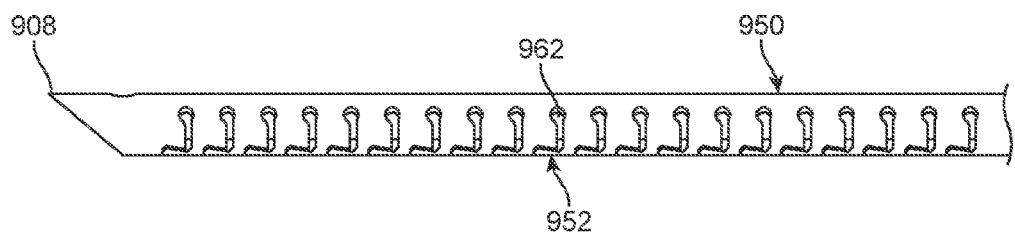
FIGS. 26A-26C illustrate a variation of an inner sleeve.
Figure 26B:
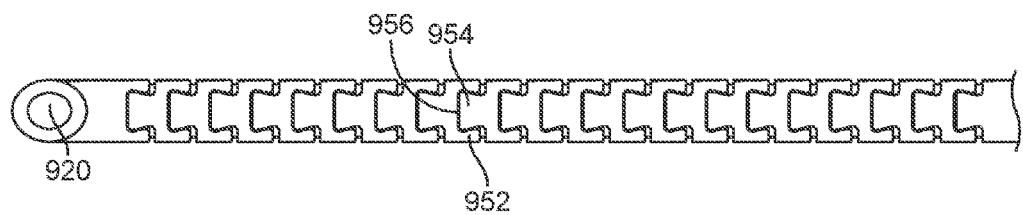
Figure 26C:
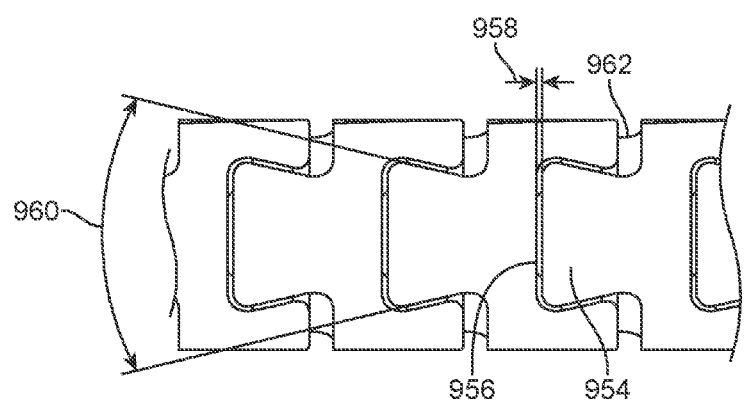

FIG. 26A illustrates a variation of an inner sleeve 950 similar to that shown in FIG. 24C where the inner sleeve 950 includes a plurality of keyed slots 952 located in such a manner that they are rotationally offset by 180 degrees relative to the plurality off keyed slots 932 on the outer sleeve 930. FIG. 26B shows the keyed slots 52 as having adjacent edges that form a keyed portion 954 and a respective key receiving portion 956. The keyed portion 954 and respective key receiving portion 956 are separated by a gap 958 and include a taper angle 960 where the span of the taper angle 960 is also reversed to the taper angle 940 of the outer sleeve 930. In other words, on the outer sleeve 930, the taper increases (or the edges of the keyed portion 934) diverge in a direction towards the handle of the device, while on the inner sleeve 950, the taper increases (or the edges of the keyed portion 954) diverge in a direction towards the tip 908 of the device. In the illustrated variation shown in FIG. 26A, the inner sleeve includes an opening or lumen 920 that can be used to deliver materials and/or fluid through the shaft. In alternate variations, the tip 908 is a solid member as shown above.

In addition, as the inner sleeve 950 articulates, the gap 958 between the parallel edges of the keyed portion 954 and the key receiving portion 956 increases while the gap between the tapered sides of the keyed portion 954 and the key receiving portion 956 decreases such that the tapered sides ultimately contact each other.

In alternate variations, the direction of the taper can be altered as desired for example, the outer sleeve can have the taper orientation shown in FIG. 26B and the inner sleeve can have the orientation shown in FIG. 25B. Alternatively, in yet additional variations, the taper orientation can be the same in both sleeves.

Figure 27A:
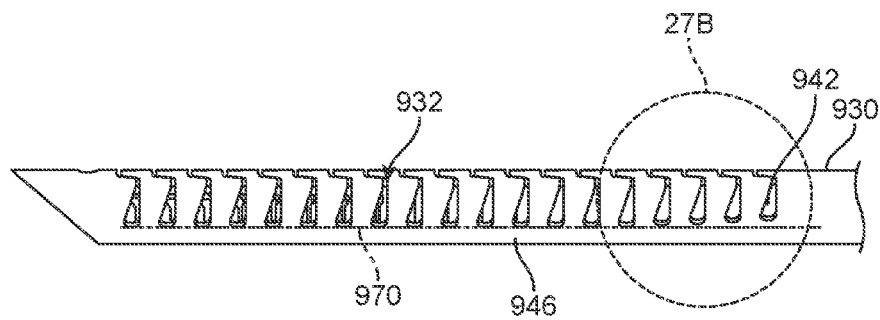
FIGS. 27A-27C show another aspect of a sleeve design with varying levels of depth.
Figure 27B:
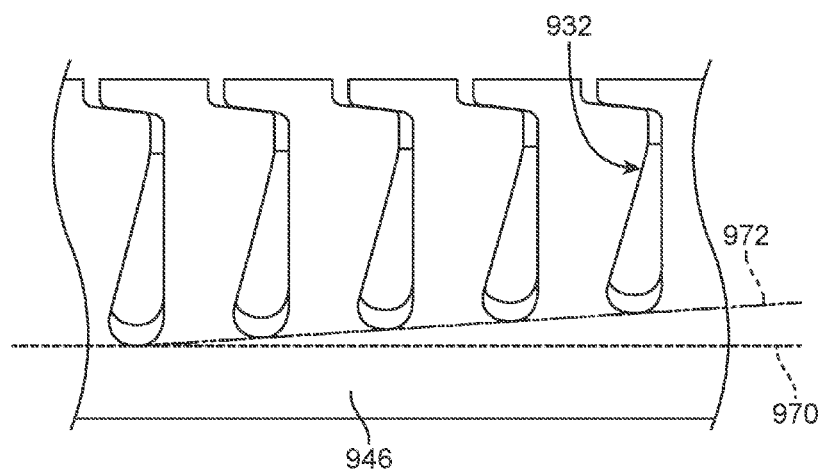
Figure 27C:
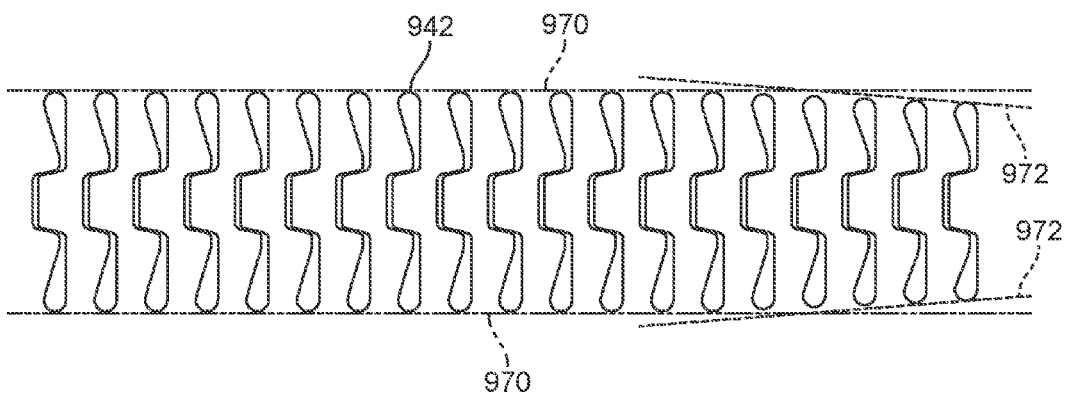

FIGS. 27A to 27C show another aspect of a feature of a sleeve design for use with variations of the devices described herein. In this variation, the slots 932 are designed with varying levels of depth. While the illustrations show the varying slot depth with respect to the outer sleeve 930, the inner sleeve can also optionally include a plurality of slots having a depth that vary.

FIG. 27A illustrates a plurality of keyed slots 932 having a clearance gap 942 that extends to a uniform distance or depth in the sleeve 930 as shown by axis 970. However, the depth of the keyed slots located within region 27B begins to decrease. Reducing the depth of the rightmost keyed slots increases the amount of material on the continuous side 946 of the sleeve 930. FIG. 27B illustrates a magnified view of the region 27B of FIG. 27A. As illustrated, the right four (4) keyed slots have depth that increases, as shown by axis 972, leaving more material on the continuous side 946 of the sleeve. It was found the highest stress concentrations occur that the proximal keyed slots so by increasing the material on the continuous side 946 of the sleeve 930 at these regions, the failure rate of the device can be reduced. Typically, prior to this configuration, the device failed by developing cracks in continuous region, where the crack propagated from the edge of the clearance gap.

FIG. 27C illustrates a planar representation of the keyed slot pattern where the edges of the clearance gap 942 are along axis 970 for full depth slots and the edges of the clearance gaps 942 for slots of decreasing depth are along axis 972. In certain variations, the depth of the slots can vary continuously along all of the keyed slots or, alternatively, along only a portion of the keyed slots. Reducing the depth of some or all of the keyed slots can be useful for the outer sleeve, inner sleeve, or both as well as any number of additional sleeves that form the shaft.

Figure 28A:
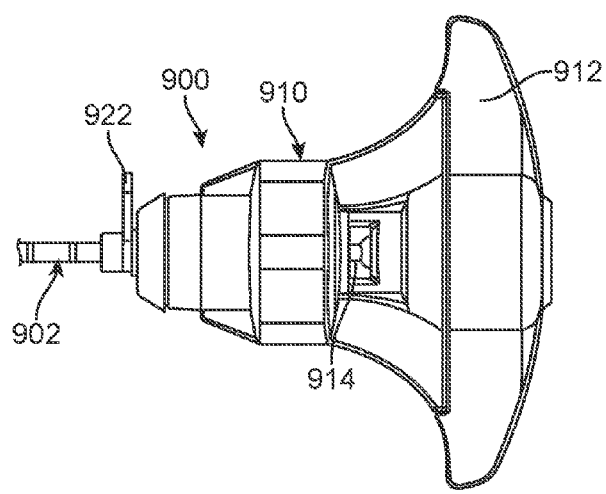
FIGS. 28A-28D illustrate a variation of an actuation mechanism of a device as described herein.

FIGS. 28A to 28D illustrate a variation of an actuation mechanism of a device 900 as described herein. FIG. 28A illustrates a handle portion 910 having an actuator member 912, where rotation of the actuator member 912 causes the shaft (not shown) to move between the linear and articulated position as noted above. The actuator member 912 can also be rotated in a reverse direction when the shaft is in a linear configuration to produce the reverse articulated configuration shown in FIG. 25E above. FIG. 28A also shows the handle 910 with a window 914 that allows the physician to indirectly observe the degree of articulation of the working end of the shaft when the working end of the shaft is inserted into a body portion or tissue. FIG. 28A also shows the shaft 902 as having a directional indicator 922 to permit the physician to identify the plane or direction in which the workings end articulates and/or a direction of the tip 908 of the shaft 902.

Figure 28B:
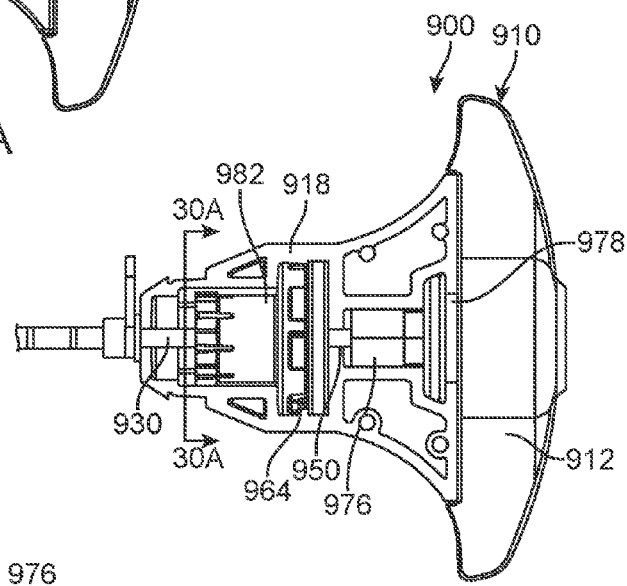
Figure 28C:
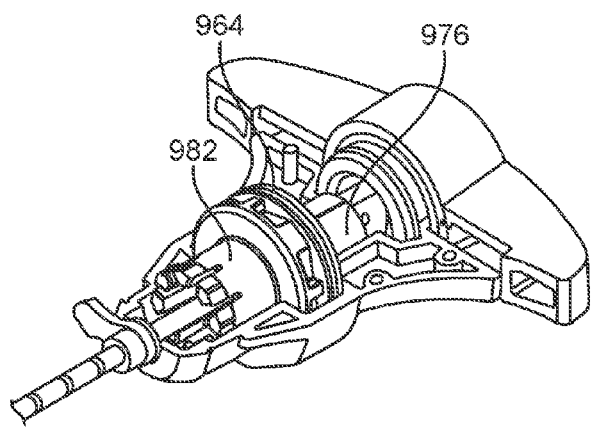
Figure 28D:
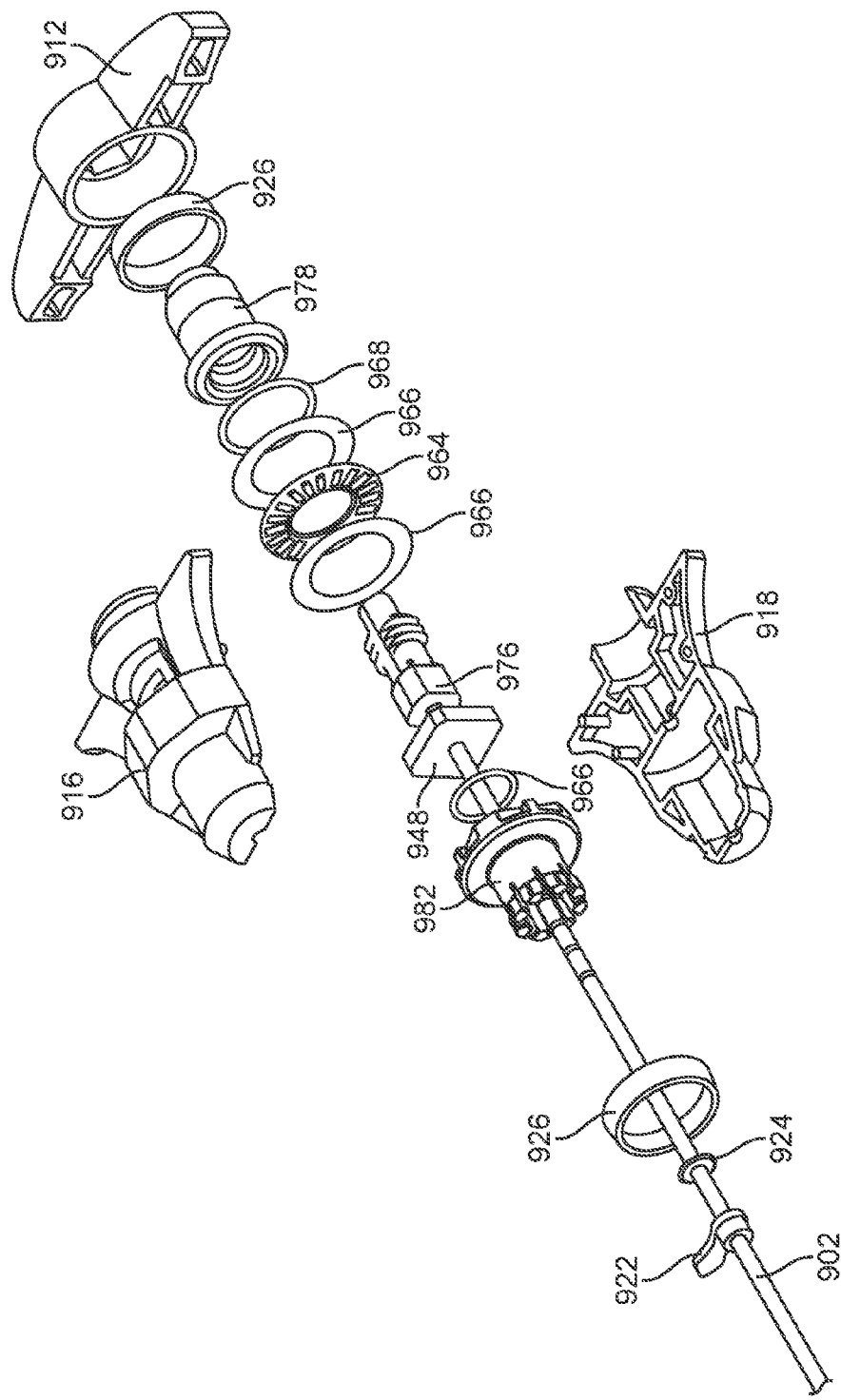

FIGS. 28B and 28C illustrates the handle 910 of the device 900 of FIG. 28A with an upper shell of the handle removed to better illustrate the articulating mechanism of the device 900 when positioned within a lower shell 916 of the handle 910.

In the example shown, the outer sleeve 930 is coupled to a torque limiter 982 as described below. In operation, rotation of the actuator 910 causes relative movement of the inner sleeve 950 relative to the outer sleeve 930. As shown, and described in detail below, the inner sleeve is coupled to a male thread actuator component 976 that translates the rotational motion of the actuator 910 into linear movement. The linear movement of the male thread actuator component 976 moves the inner sleeve relative to the outer sleeve.

The outer sleeve 930 is coupled to a torque limiter 982, which works together with the shells of the handle 910 as a release system. This release system limits the amount of rotational force that can be applied to the entire handle assembly before it freely rotates. For example when the working end of the shaft is in an articulated configuration within tissue and a physician attempts to rotate the handle, the articulated section of the shaft will apply a force against the adjacent tissue. However, if the working end of the shaft engages hard or strong tissue and the physician applies a rotational force that exceeds the torque limit set by the release assembly, the release system causes the handle 910 to rotate relative to the shaft 902 thereby preventing failure of the device or unintended trauma to the patient. As discussed below, the release system illustrated in FIGS. 28A-28D was found to produce devices with minimal deviation of the torque required to trigger the release system. FIGS. 28A to 28D also show a thrust bearing 964 with adjacent washers 966, which allows for rotation of the torque limiter 982 and proximal end of the outer sleeve 930 while supporting any axial load cause by the movement of the inner sleeve 950 relative to the outer sleeve 930.

The torque limiter can be designed for any range of torque thresholds/limits, including but not limited 0.5 inch*lbs to about 7.5 inch*lbs, 5.0 inch*lbs or 2.5 inch*lbs, the rotation of the handle 115 overcomes the predetermined limit. When the torque limiter assembly rotates relative to the handle, the interference between the torque limiter and the handle provides the torque threshold/limit. When an amount of torque is provided to the handle and outer sleeve that is greater than the designed torque threshold/limit, resistance surfaces on the torque limiter deflect allowing the shaft.

In the variation of the device shown in FIGS. 28A to 28D, the articulating mechanism comprises a male thread actuator 976, a female thread actuator 978, and the actuator member 912. The male thread actuator 976 secures the proximal end of the inner sleeve 950 at one end and engages a female thread actuator 978 at its other end. The female thread actuator 978 couples to the actuator member 912 such that rotation of the actuator member 912 causes rotation of the female thread actuator 978, which moves the male thread actuator 976 within the female thread actuator 978. Movement of the male thread actuator 976 moves the inner sleeve 950 relative to the outer sleeve 930 causing articulation of the shaft. As noted above, the male thread actuator 976 can be visible within a window 914 of the handle 910. Accordingly, the male thread actuator 976 can be constructed from a clear material so that the proximal end of the inner sleeve 950 is visible within the window 914 and provides guidance to the physician on the degree of articulation of the shaft. Alternatively, or in combination, the male thread actuator 976 can have markings that are visible within the window 914.

The male thread actuator 976 can be configured as a "clam shell" design where each half of the male thread actuator 976 shell encloses the proximal end of the inner sleeve 950. In the illustrated variation, the seam formed by each shell of the male thread actuator 976 shell is rotated 90 degrees relative to the seam formed by the adjacent shells of the handle 910. Such a configuration increases the amount of force that the male thread actuator 976 can apply to the proximal end of the inner sleeve 950 without causing the inner sleeve 950 from disengaging from the male thread actuator 976.

FIG. 28C shows an exploded assembly view of the device shown in FIGS. 28A-C. In addition to those components already discussed above, the device can optionally include any number of spacers 924 and collars 926 for normal assembly purposes. Furthermore, variations of the device can use deflectable members to accommodate the natural dimensional tolerances between components in the handle. Such deflectable members include, but are not limited to spring washers, o-rings, or other structure that provides flexibility.

Figure 29A:
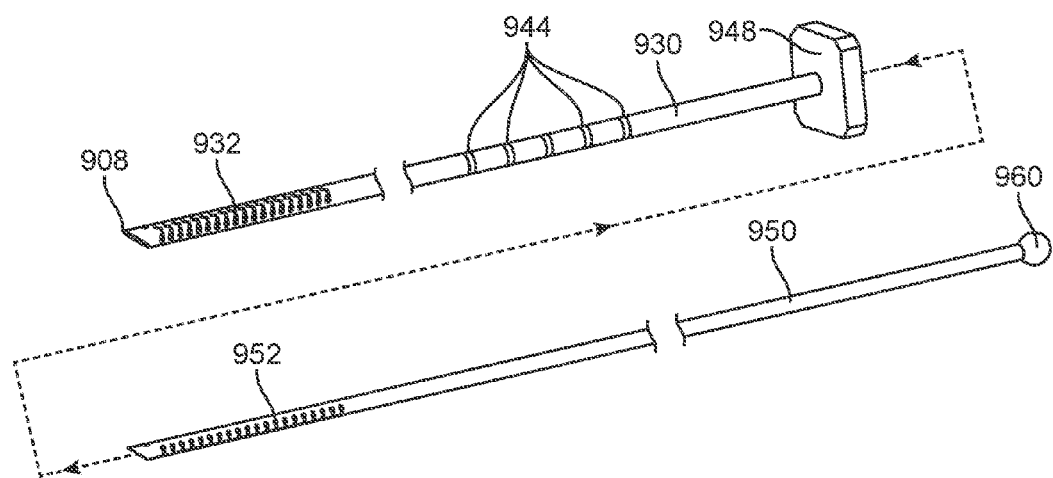
FIGS. 29A-29C show an example of an inner and outer sleeve operatively coupled to an actuation mechanism.
Figure 29B:
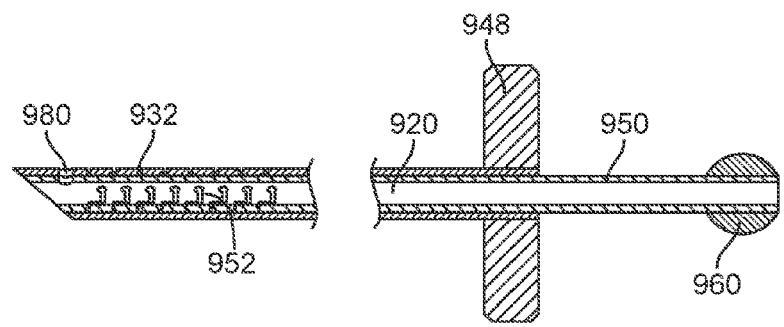

FIGS. 29A and 29B illustrate an example of an outer sleeve 930 and inner sleeve 950. FIG. 29A shows the sleeves 930 and 950 in an exploded view. As shown, the inner and/or outer sleeve distal ends form the sharp tip 902. In additional variations, one sleeve forms the sharp tip or an insert is positioned in the sleeves where the insert forms the sharp tip. The outer sleeve can include any number of depth markings 944 as well as other features to aid the physician in positioning the device.

Also the illustrated sleeves include the keyed slots 932 and 952 to form the articulating section of the shaft. However, in alternate variations of the device, one or both of the sleeves can include non-keyed slots as described herein.

FIG. 29A also illustrates the outer sleeve 930 having a plate 948 affixed to a proximal end. As described above, the plate 948 can be coupled to the handle, or to the torque limiter as shown above. The inner sleeve 950 is positioned within the outer sleeve 930 such that the slots in each sleeve are located on opposite sides of the sleeves. For example, the slots 932 in the outer sleeve are adjacent to the continuous section of the inner sleeve 950, while the slots of the inner sleeve 950 are adjacent to the continuous section of the outer sleeve 930. The distal ends of the sleeves 930 and 950, beyond the slots are affixed such that relative movement of the inner sleeve 950 relative to the outer sleeve 930 causes articulation. Optionally, the outer sleeve and/or inner sleeve can include an opening 980 that aids in alignment of the sleeves and/or fixation of the sleeve.

FIG. 29A and 29B also illustrate the inner sleeve with an area of increased diameter 960 (e.g., a ball) located at the proximal end. As discussed herein, the ball or increased diameter region allows rotation of the male thread actuator 976 about the increased diameter region 960. In addition, the inner sleeve 950 can include a lumen 920 (in which case the lumen opening will extend through the handle to a port, luer, or other fitting.)

Figure 29C:
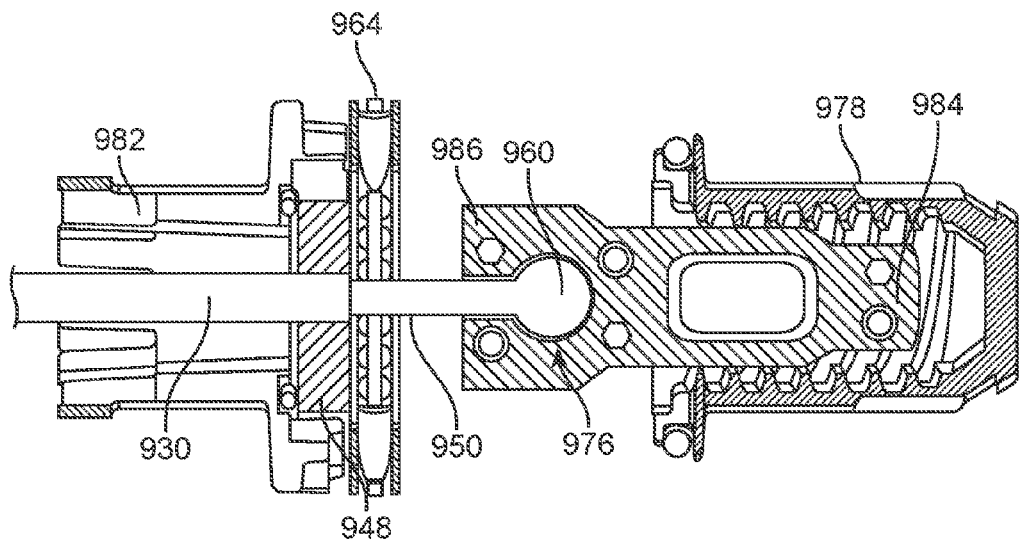

FIG. 29C illustrates the actuator mechanism coupled to the increased diameter 960 of the inner sleeve 930. As shown, the female thread actuator 978 includes a threaded inner portion that engages threads on the outer portion of the male thread actuator 984. Rotation of the female thread actuator 978 (via the actuator member of the handle) causes axial movement of the male thread actuator 976 since the female thread actuator 978 is constrained from axial movement in the handle housing. The male thread actuator 976 includes proximal 984 and distal stops 986, which limit articulation of the shaft when the stops engage the female thread actuator (proximal stop 984) or the housing assembly (distal stop 986). The outer sleeve plate 948 is prevented from axial movement by the handle body so that axial movement of the inner sleeve 950 causes relative movement between the sleeves to articulate the sleeves. The inner sleeve 950 can rotate relative to the male thread actuator 976 but is prevented from rotation due to the coupling of the outer sleeve 948 to the torque limiter 982.

Figure 30A:
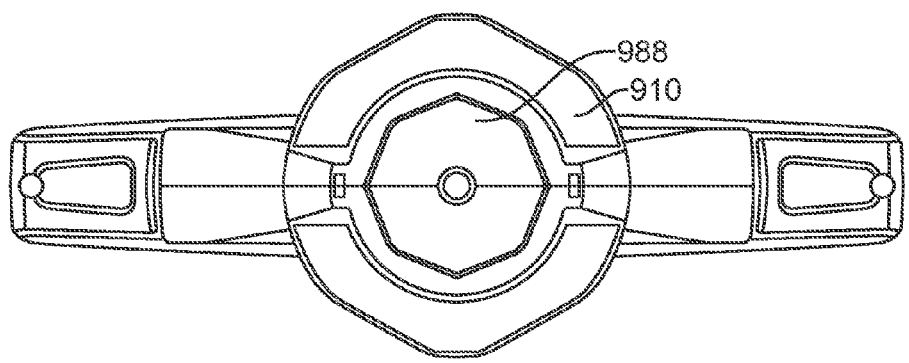
FIGS. 30A-30D illustrate an example of a torque limiter designed to minimize surface area contact when providing resistance to torqueing of the device.

As discussed above, the torque limiter 982 limits the rotational force that can be applied to the articulated working end of the shaft. In one variation of the device, the torque limiter 982 is designed to minimize surface contact with resistance points within the torque chamber 988 of the handle 910. FIG. 30A, illustrates a cross sectional view taken along line 30A-30A in FIG. 28B (where the torque limiter and shaft are hidden to illustrate the chamber 982). In this variation, the chamber 988 comprises a cross sectional shape that nests the torque limiter and only provides resistance upon relative rotation between the chamber 982 and torque limiter 982. This configuration minimizes surface contact between the surface of the chamber 982 and the surface of the torque limiter. Minimizing surface contact between components was found to provide for consistency in torque thresholds across devices since the surface of the components can become altered during processing, sterilization or storage of the devices. Accordingly, a torque limiter configuration that is engaged upon relative rotation of the components can result in a lower standard deviation of measured torque thresholds.

Figure 30B:
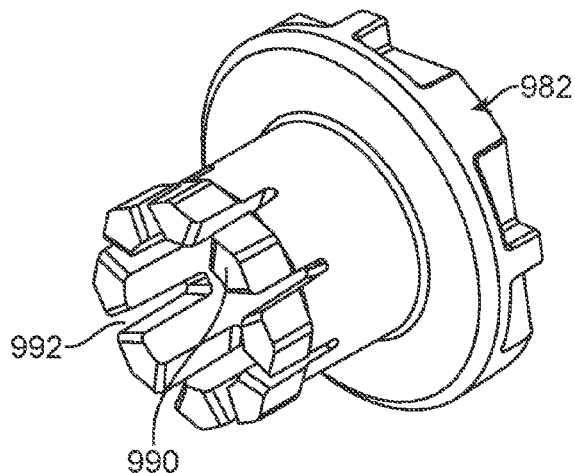
Figure 30C:
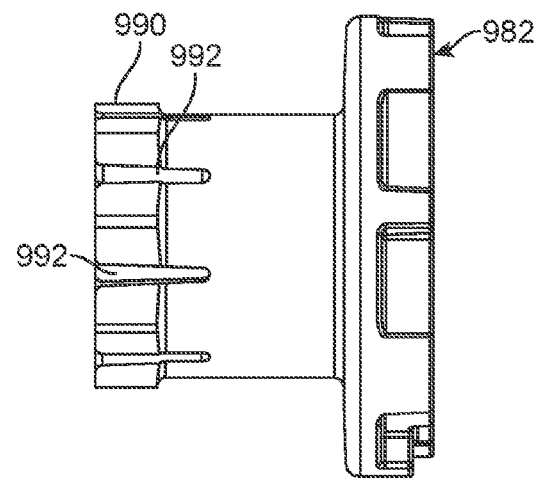
Figure 30D:
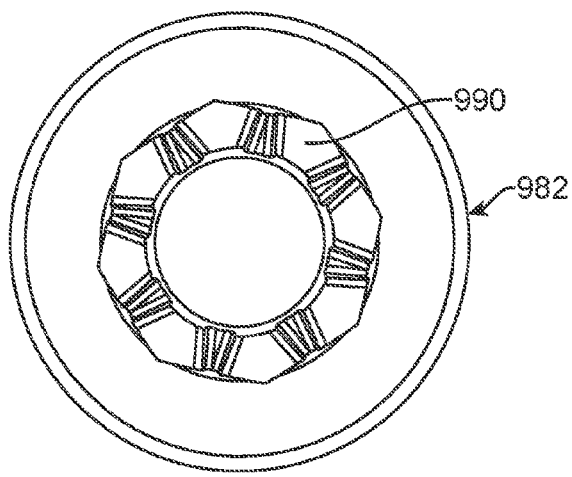

FIG. 30B illustrates a perspective view of a torque limiter 982, where the torque limiter includes a plurality of resistance surfaces 990 that are formed/cut into the torque limiter 982 to form a series of arm or cantilever construction, where the resistance surfaces 990 are configured to have a greater diameter than an adjacent section of the torque limiter (as seen in FIG. 30C) so that upon rotation, the resistance surfaces deflect the slotted portion of the torque limiter 982. The torque chamber 988 and cross sectional profile of the resistance surfaces (as shown by FIG. 30D) are designed so that after the torque limiter rotates (or the chamber rotates relative to the torque limiter), the resistance surfaces return to an un-deflected state. Once in the un-deflected state the outer diameter of the resistance surfaces 990 (as viewed in FIG. 30D) is slightly less than the inner diameter of the torque chamber 988 (as viewed by FIG. 30A). The torque threshold of the torque limiter can be adjusted by selection of materials, depth and/or width of the grooves 992 forming the arm or cantilever construction.

In the example shown in FIG. 30A, the torque chamber comprises a non-circular cross section. The illustrated variation shows an octagon shape, but variations can include any polygon shape, any non-symmetrical shape (e.g., oval, elliptical, etc.), or any uniform shape (e.g., circular) with resistance points to provide interference with the resistance surface 990 of the torque limiter 982.

Figure 31:
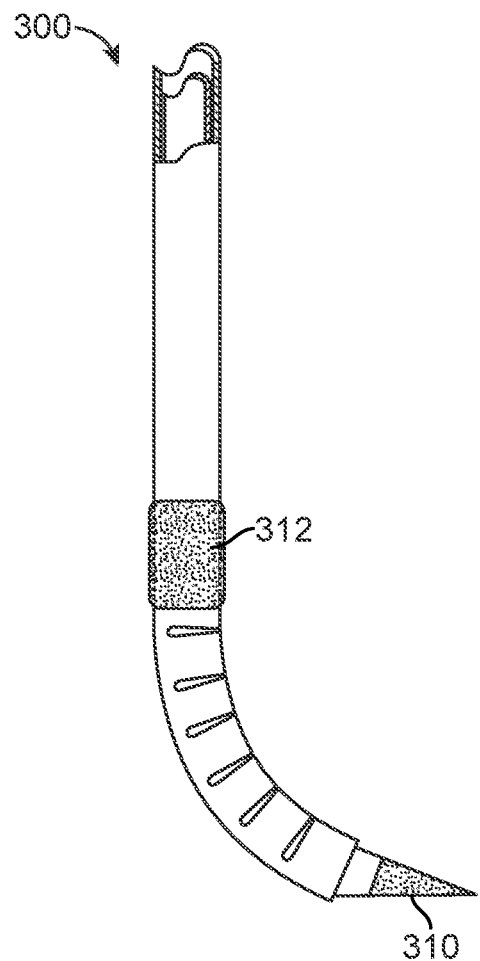
FIG. 31 illustrates a variation of an osteotome as described herein having electrodes on a tip of the device and another electrode on the shaft.

In an additional variation, the devices described above can include one or more electrodes 310, 312 as shown in FIG. 31. In this particular example, the device 300 includes spaced apart electrodes having opposite polarity to function in a bi-polar manner. However, the device can include a monopolar configuration. Furthermore, one or more electrodes can be coupled to individual channels of a power supply so that the electrodes can be energized as needed. Any variation of the device described above can be configured with one or more electrodes as described herein.

Figure 32:
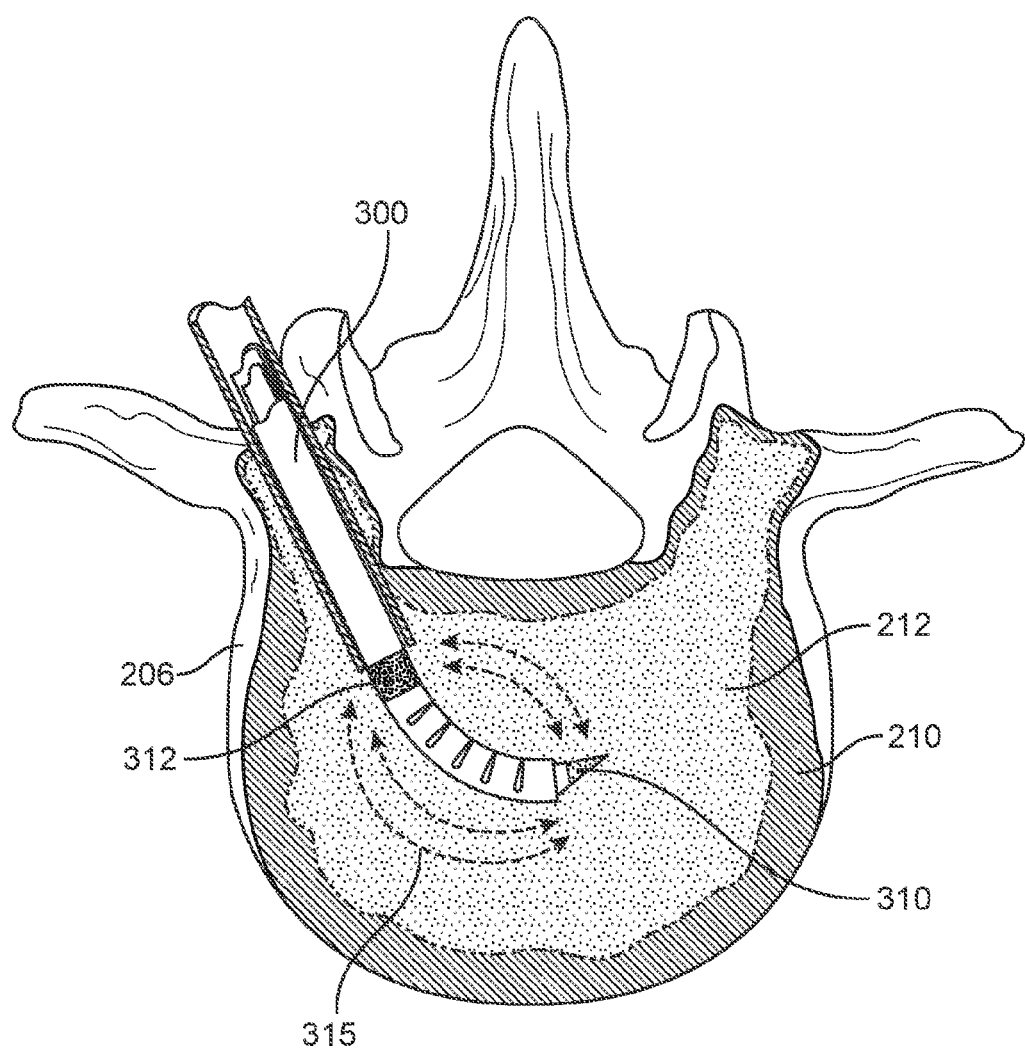
FIG. 32 illustrates an osteotome device as shown in FIG. 31 after being advanced into the body and where current passes between electrodes.

FIG. 32 illustrates an osteotome device 300 after being advanced into the body as discussed above. As shown by lines 315 representing current flow between electrodes, when required, the physician can conduct RF current between electrodes 310 and 312 to apply coagulative or ablative energy within the bone structure of the vertebral body (or other hard tissue). While FIG. 32 illustrates RF current 315 flow between electrodes 310 and 312, variations of the device can include a number of electrodes along the device to apply the proper therapeutic energy. Furthermore, an electrode can be spaced from the end of the osteotome rather than being placed on the sharp tip as shown by electrode 310. In some variations, the power supply is coupled to the inner sharp tip or other working end of the first sleeve. In those variations with only two sleeves, the second pole of the power supply is coupled with the second sleeve (that is the exterior of the device) to form a return electrode. However, in those variations having three sleeves, the power supply can alternatively be coupled with the third outer sleeve. In yet additional variations, the second and third sleeves can both function as return electrodes. However, in those devices that are monopolar, the return electrode will be placed outside of the body on a large area of skin.

FIGS. 33 to 37 illustrate another variation of an articulating probe or osteotome device 500. In this variation, the device 500 includes a working end 505 that carries one or more RF electrodes that can be used to conduct current therethrough. Accordingly, the device can be used to sense impedance of tissue, locate nerves, or simply apply electrosurgical energy to tissue to coagulate or ablate tissue. In one potential use, the device 500 can apply ablative energy to a tumor or other tissue within the vertebra as well as create a cavity.

Figure 33:
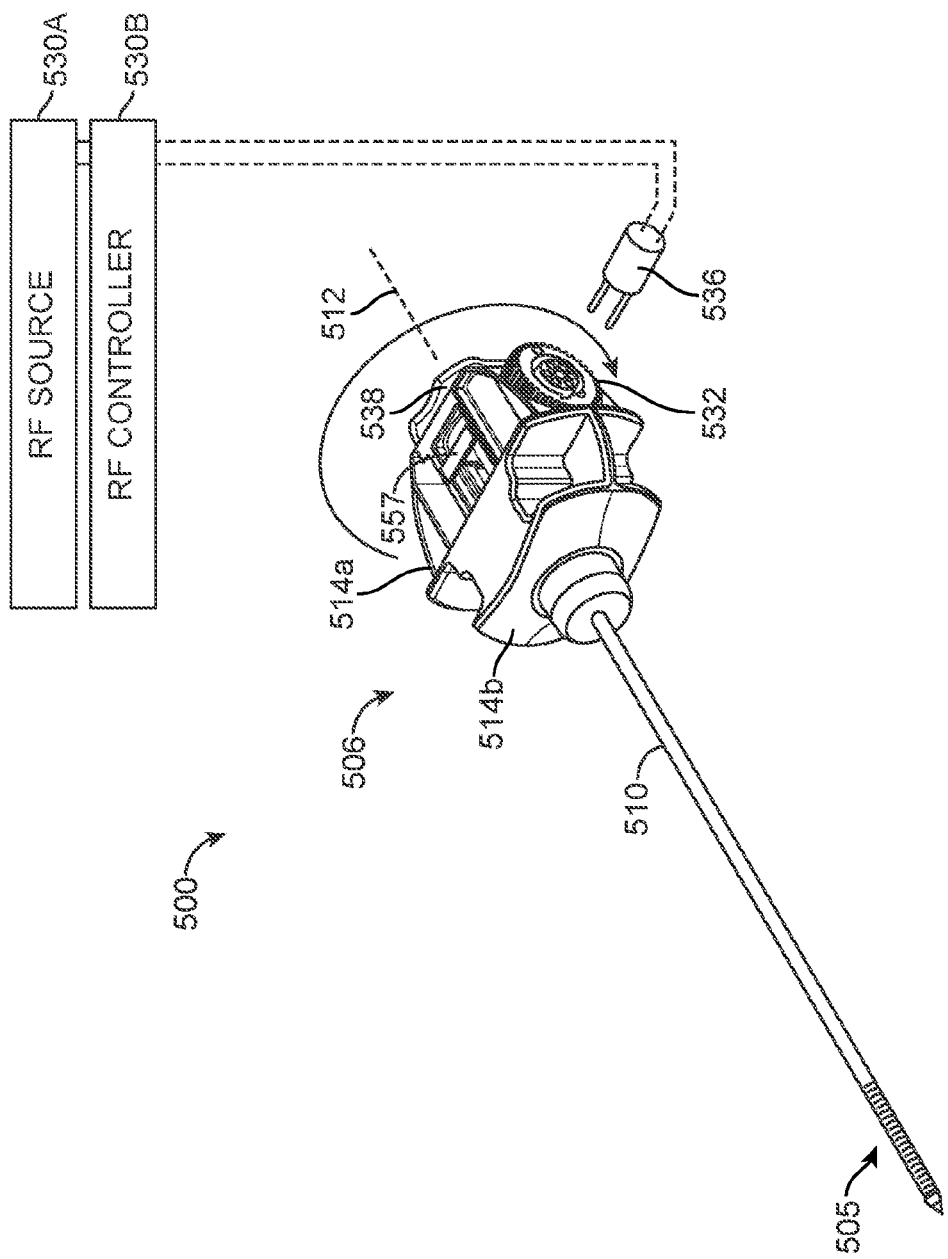
FIG. 33 illustrates a variation of a device as described herein further including a connector for providing energy at the working end of the device.
Figure 34A:
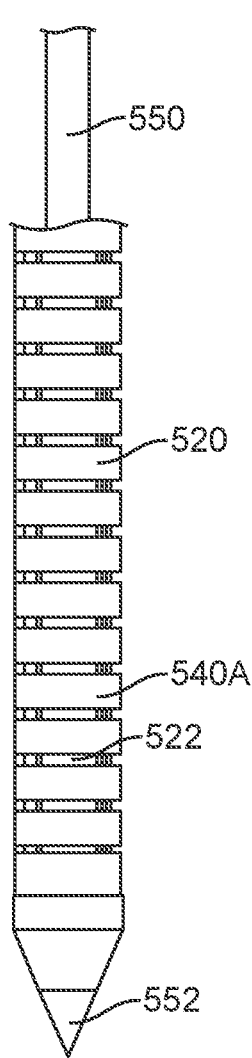
FIGS. 34A and 34B illustrate a device having a sharp tip as disclosed herein where the sharp tip is advanceable from the distal end of the shaft.
Figure 34B:
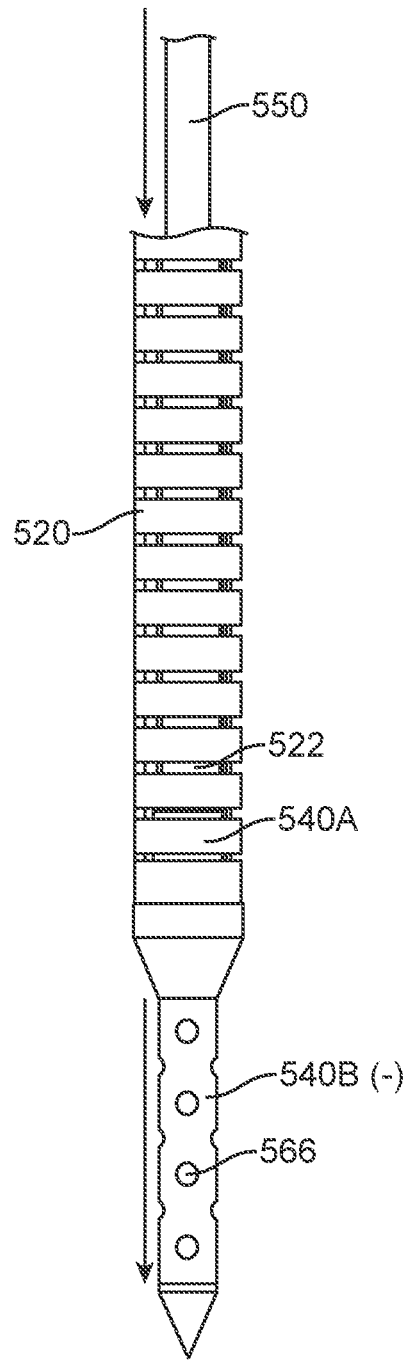
Figure 35:
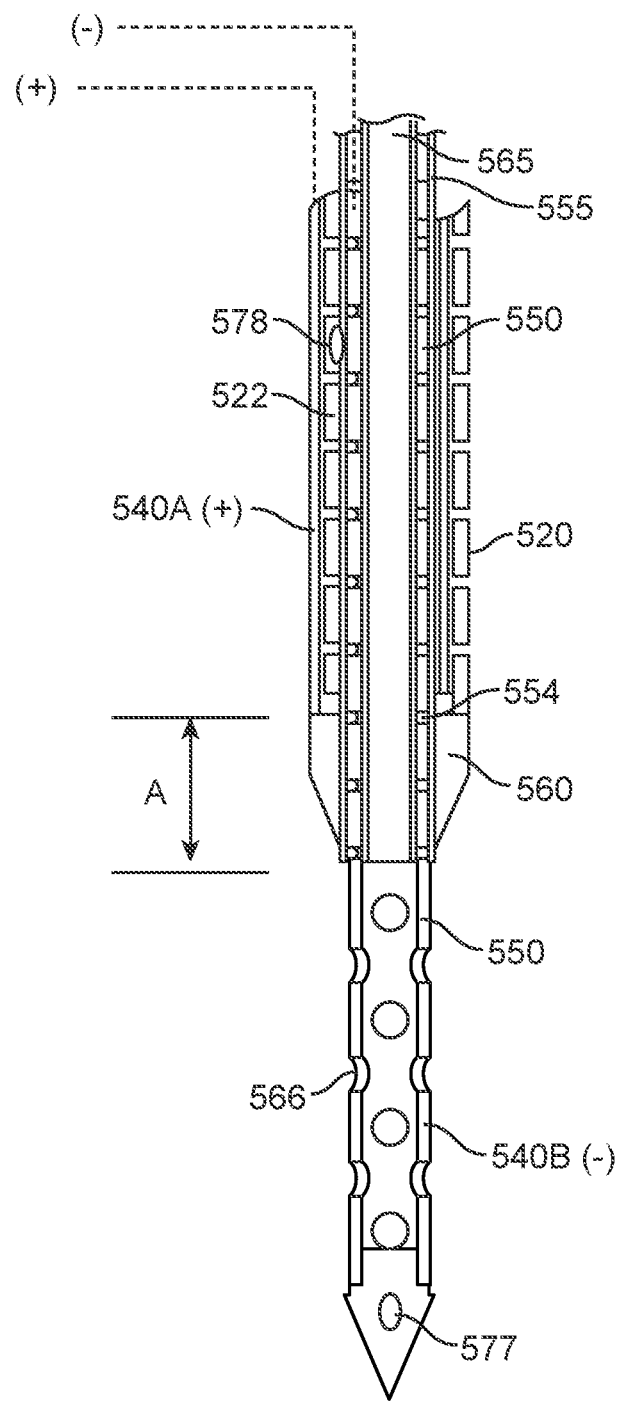
FIG. 35 shows a cross sectional view of the device illustrated in FIG. 34B and also illustrates temperature sensing elements located on device.

FIGS. 33, 34A, 34B and 35, illustrate a variation of the device 500 as having a handle portion 506 coupled to a shaft assembly 510 that extends along axis 512 to the articulating working end 505. The articulating working end 505 can be actuatable as described above. In addition, FIG. 33 shows that handle component 514a can be rotated relative to handle component 514b to cause relative axial movement between a first outer sleeve 520 and second inner sleeve 522 (FIG. 35) to cause the slotted working ends of the sleeve assembly to articulate as described above. The working end 505 of FIG. 35 shows two sleeves 520 and 522 that are actuatable to articulate the working end, but it should be appreciated that a third outer articulating sleeve can be added as depicted above. In one variation, the articulating working end can articulate 90° by rotating handle component 514a between ¼ turn and ¾ turn. The rotating handle component 514a can include detents at various rotational positions to allow for controlled hammering of the working end into bone.

For example, the detents can be located at every 45° rotation or can be located at any other rotational increment.

FIG. 33 depict an RF generator 530A and RF controller 530B connectable to an electrical connector 532 in the handle component 514a with a plug connector indicated at 536. The RF generator is of the type known in the art for electrosurgical ablation. The outer sleeve 520 comprises a first polarity electrode indicated at 540A (+). However, any energy modality can be employed with the device.

Figure 36:
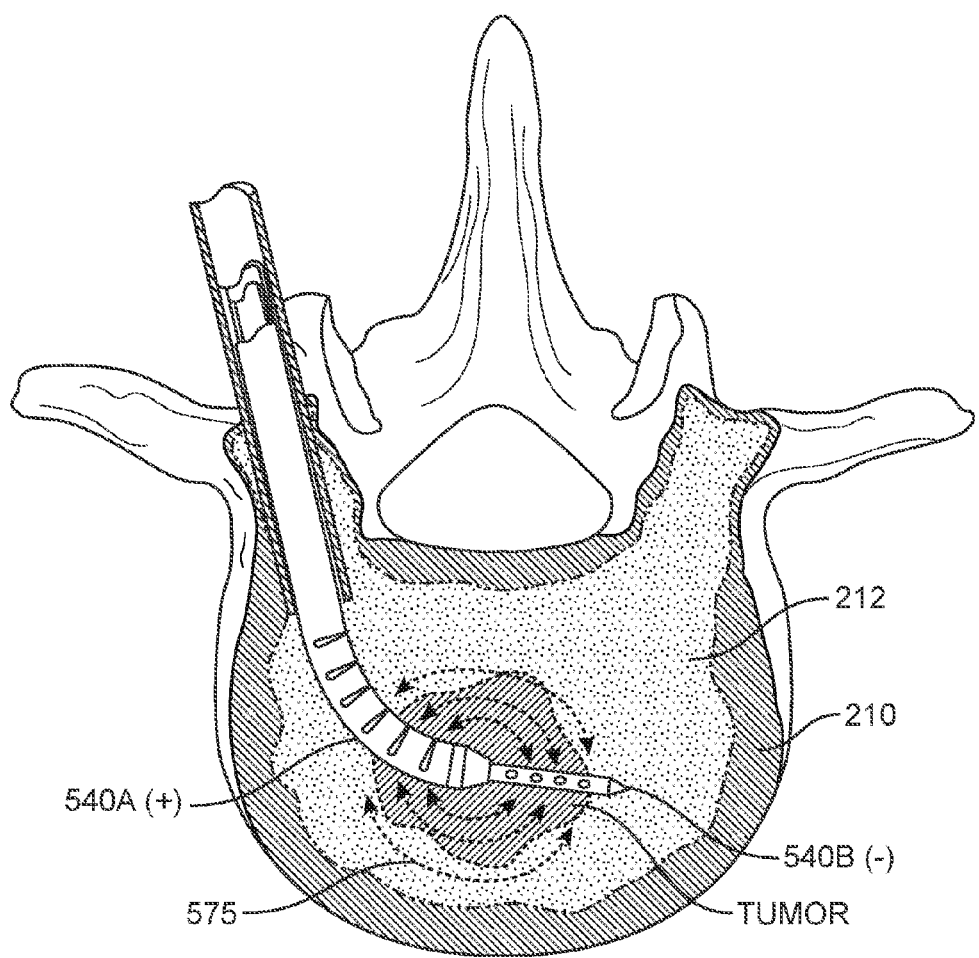
FIG. 36 shows a variation of a device where the inner sleeve is extended from the device and where current is applied between the extended portion of the inner sleeve and the shaft to treat tissue.

FIGS. 34A and 34A illustrate yet another variation of a working end of a device for creating cavities in hard tissue. As shown, the device 500 can include a central extendable sleeve 550 with a sharp tip 552 that is axially extendable from passageway 554 of the assembly of first and second sleeves 520 and 522 (FIG. 36). The sleeve 550 can also include a second polarity electrode indicated at 540B (−). Clearly, the first and second electrodes will be electrically insulated from one another. In one variation, and as shown in FIG. 36, the sleeve assembly can carry a thin sleeve 555 or coating of an insulative polymer such as PEEK or Ceramic to electrically isolate the first polarity electrode 540A (+) from the second polarity electrode 540B (−). The electrode can be deployed by rotating knob 558 on the striking surface of handle component 514a (FIG. 33). The degree of extension of central sleeve 550 can optionally be indicated by a slider tab 557 on the handle. In the illustrated variation, the slider tab is located on either side of handle component 514a (FIG. 33). Sleeve 550 can be configured to extend distally beyond the assembly of sleeves 520 and 522 a distance of about 5 to 15 mm.

Referring. to FIG. 35, the central extendable sleeve 550 can have a series of slots in at least a distal portion thereof to allow it to bend in cooperation with the assembly of first and second sleeves 520 and 522. In the embodiment shown in FIG. 34B, the central sleeve 550 can optionally include a distal portion that does not contain any slots. However, additional variations include slots on the distal portion of the sleeve.

FIG. 35 further depicts an electrically insulative collar 560 that extends length A to axially space apart the first polarity electrode 540A (+) from the second polarity electrode 540B (−). The axial length A can be from about 0.5 to 10 mm, and usually is from 1 to 5 mm. The collar can be a ceramic or temperature resistant polymer.

FIG. 35 also depicts a polymer sleeve 565 that extends through the lumen in the center of electrode sleeve 550. The polymer sleeve 565 can provide saline infusion or other fluids to the working end and/or be used to aspirate from the working end when in use. The distal portion of sleeve 550 can include one or more ports 566 therein for delivering fluid or aspirating from the site.

In all other respects, the osteotome system 500 can be driven into bone and articulated as described above. The electrodes 540A and 540B are operatively coupled to a radiofrequency generator as is known in the art for applying coagulative or ablative electrosurgical energy to tissue. In FIG. 36, it can be seen that RF current 575 is indicated in paths between electrodes 540A and 540B as shown by lines 575. RF generator 530A and controller 530B for use with the devices described herein can include any number of power settings to control the size of targeted coagulation or ablation area. For example, the RF generator and controller can have Low or power level 1 (5 watts), medium or power level 2 (10 Watts) and High or power level 3 (25 watts) power settings. The controller 530B can have a control algorithm that monitors the temperature of the electrodes and changes the power input in order to maintain a constant temperature. At least one temperature sensing element (e.g., a thermocouple) can be provided on various portions of the device. For example, and as shown in FIG. 35, a temperature sensing element 577 can be provided at the distal tip of sleeve 550 tip while a second temperature sensing element 578 can be provided proximal from the distal tip to provide temperature feedback to the operator to indicate the region of ablated tissue during the application of RF energy. In one example, the second temperature sensing element was located approximately 15 to 20 mm from the distal tip.

Figure 37:
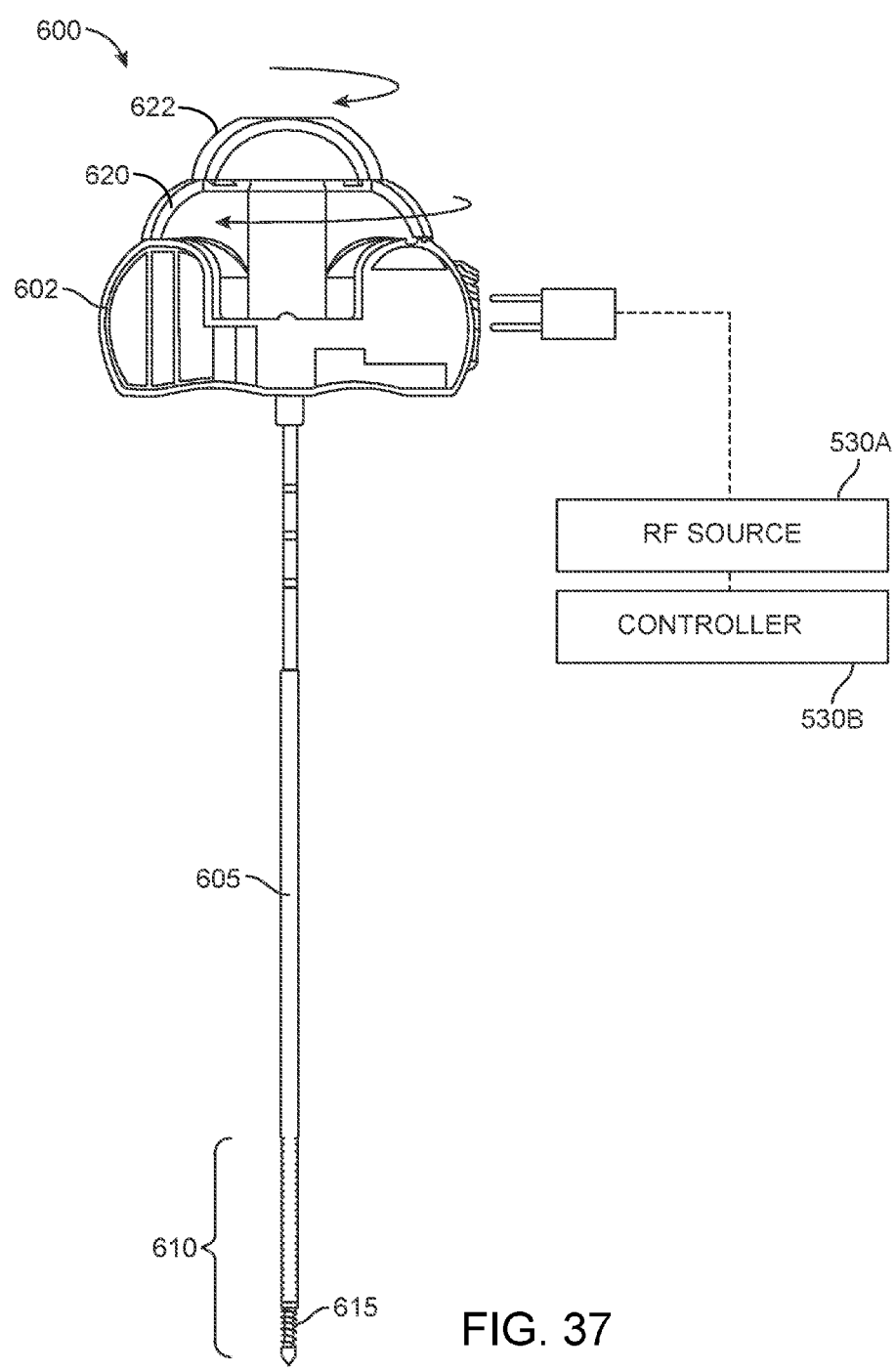
FIG. 37 illustrates a variation of a device as described herein further including an extendable helical electrode carried by the working end of the device.

FIG. 37 illustrates another variation of articulating osteotome 600 with RF ablation features. Variations of the illustrated osteotome 600 can be similar to the osteotome of FIGS. 33-35B. In this variation, the osteotome 600 of has a handle 602 coupled to shaft assembly 610 as described above. The working end 610 again has an extendable assembly indicated at 615 in FIG. 37 that can be extended by rotation of handle portion 622 relative to handle 602. The osteotome can be articulated as described previously by rotating handle portion 620 relative to handle 602.

Figure 38A:
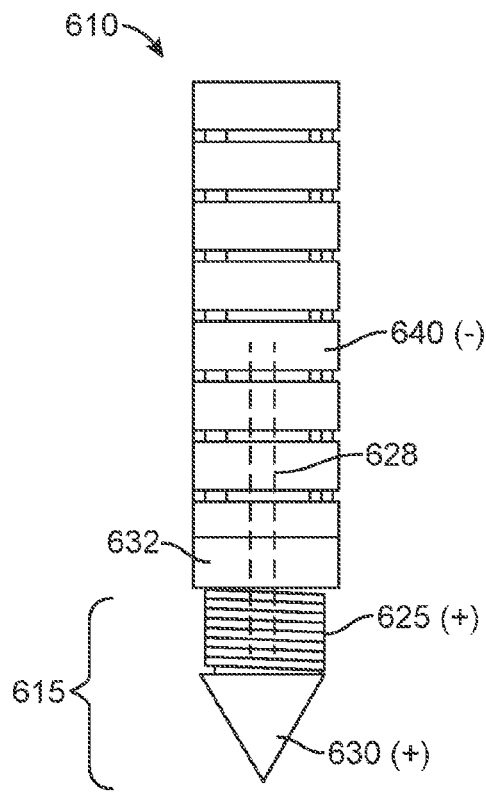
FIGS. 38A and 38B illustrate the device of FIG. 35 with the helical electrode in a non-extended position and an extended position.
Figure 38B:
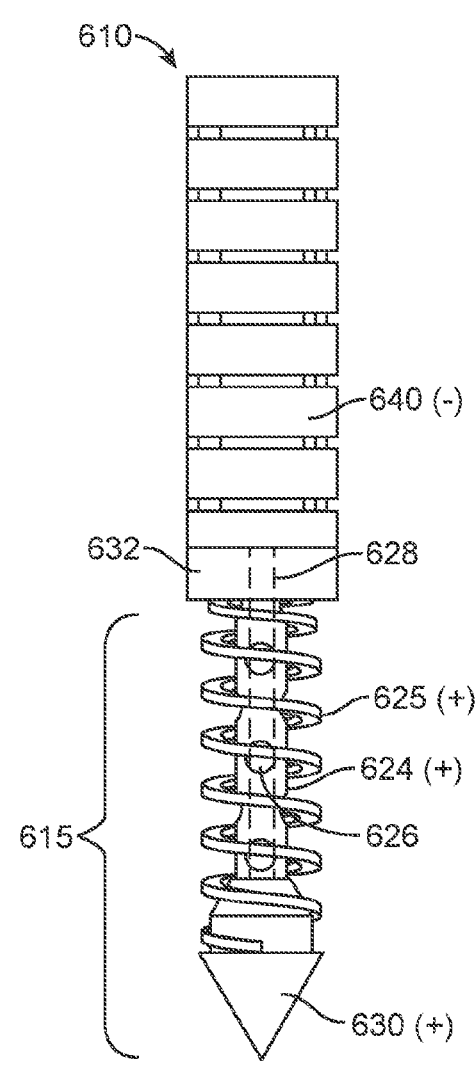

FIGS. 38A-38B are views of the working end 610 of FIG. 38 in a first non-extended configuration (FIG. 38A) and a second extended configuration (FIG. 39B). As can be seen in FIGS. 38A-38B, the extension portion 615 comprises an axial shaft 624 together with a helical spring element 625 that is axially collapsible and extendible. In one embodiment, the shaft can be a tube member with ports 626 fluidly coupled a lumen 628 therein. In some variations, the ports can carry a fluid to the working end or can aspirate fluid from the working end.

In FIGS. 38A-38B, it can be seen that axial shaft 624, helical spring element 625 together with sharp tip 630 comprise a first polarity electrode (+) coupled to electrical source 530A and controller 530B as described previously. An insulator 632 separates the helical spring 625 electrode from the more proximal portion of the sleeve which comprises opposing polarity electrode 640 (−). The RF electrodes can function as described above (see FIG. 37) to ablate tissue or otherwise deliver energy to tissue.

In one variation, the extension portion 615 can extend from a collapsed spring length of 2 mm, 3 mm, 4 mm or 5 mm to an extended spring length of 6 mm, 7 mm, 8 mm, 9 mm 10 mm or more. In the working end embodiment 615 in FIG. 38B, the spring can comprise a flat rectangular wire that assists in centering the spring. 625 about shaft 624 and still can collapse to short overall length, with the flat surfaces of rectangular wire oriented for stacking. However, other variations are within the scope of the variations described herein.

Of particular importance, it has been found that ability of the osteotome 600 to ablate tissue is greatly enhanced over the embodiment 500 of FIG. 37 by utilizing the helical spring. The use of the spring 625 as an electrode provides significant improvements in delivering energy. This spring provides (i) greatly increased electrode surface area and (ii) a very greatly increased length of relatively sharp edges provided by the rectangular wire—which provides for edges from which RF current can jump. Because the edges provide low surface area the concentration or density of RF current is greater at the edges and allows for the RF current to jump or arc. Both these aspects of the invention increased electrode surface area and increased electrode edge length allow for much more rapid tissue ablation.

In one aspect of the invention, the surface area of the spring electrode 625 can be at least 40 mm2, at least 50 mm2, or at least 60 mm2 over the spring electrode lengths described above.

In another aspect of the invention, the total length of the 4 edges of rectangular wire spring can be greater than 50 mm, greater than 100 mm or greater than 150 mm over the spring electrode lengths described above.

In one example used in testing, an osteotome 600 as in FIG. 37-38B was configured with a helical spring that had a collapsed length of 1.8 mm and an extended length of 7.5 mm. In this embodiment, the surface area of the spring electrode 625 when extended was 64.24 mm$^2$ and the total length of the electrodes edges was 171.52 mm (four edges at 42.88 mm per edge).

Figure 38C:
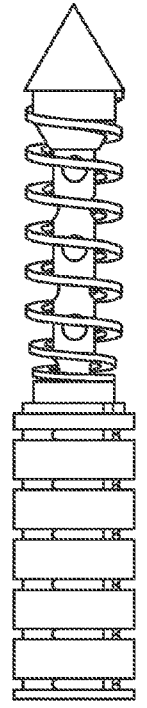
FIGS. 38C and 38D illustrate charts of variations of electrodes having ablated volumes given a particular duration of an ablation cycle.

In a comparison test, a first osteotome without a helical electrode was compared against a second osteotome 600 with a helical electrode as in FIG. 38B. These devices were evaluated at different power levels and different energy delivery intervals to determine volume of ablation. The working ends of the devices had similar dimensions excepting for the helical spring electrode. Referring to FIG. 38C, RF energy was delivered at a low power setting of 5 Watts. It can be seen in FIG. 39C that at a treatment interval of 120 seconds and 5 W, the volume of ablation was about 3 times faster with the helical electrode compared to the working end without the helical electrode (1.29 cc vs. 0.44 cc).

Figure 38D:
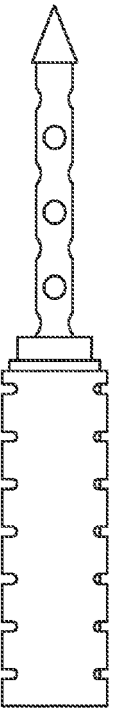

Another comparison test of the same first osteotome 500 (FIG. 35B) and second osteotome 600 with a helical electrode (FIG. 38B) were evaluated at higher 15 Watt power level. As can be seen in FIG. 38D, RF energy at a treatment interval of 25 seconds and 15 W, the volume of ablation was again was about 3 times faster with the helical electrode compared to the working end without the helical electrode (1.00 cc vs. 0.37 cc). Referring to FIG. 38D, the device without the helical electrode impeded out before 60 seconds passed, so that data was not provided. The testing shows that the helical electrode is well suited for any type of tissue or tumor ablation, with a 60 second ablation resulting in 1.63 cc of ablated tissue.

Figure 39:
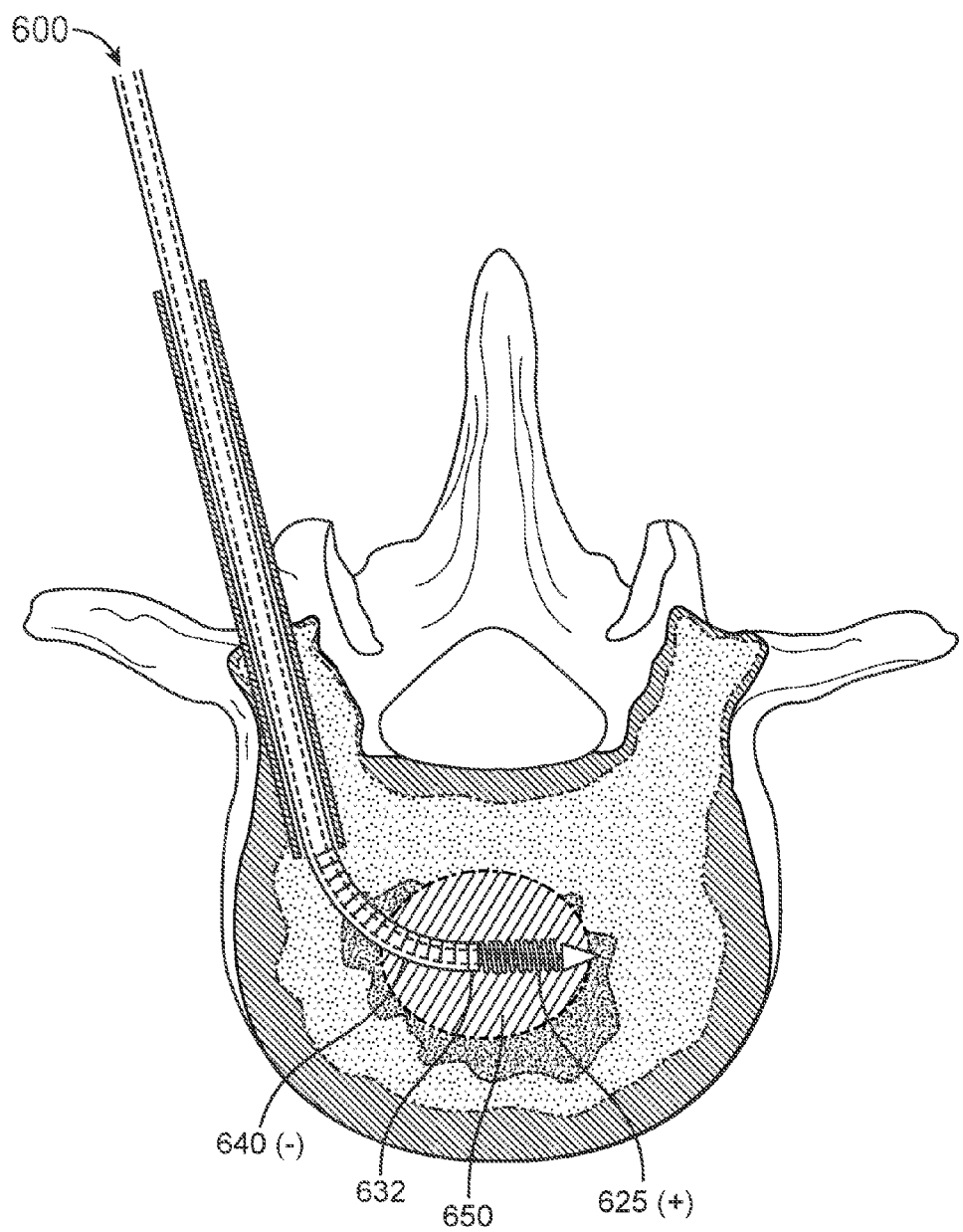
FIG. 39 illustrates the working end of the device of FIG. 36 in a vertebral body with the helical electrode delivering Rf energy to ablate tissue.

FIG. 39 schematically illustrates the osteotome 600 in use in a vertebral body, wherein the RF current between the electrodes 625 and 640 ablate a tissue volume indicated at 640.

Figure 40:
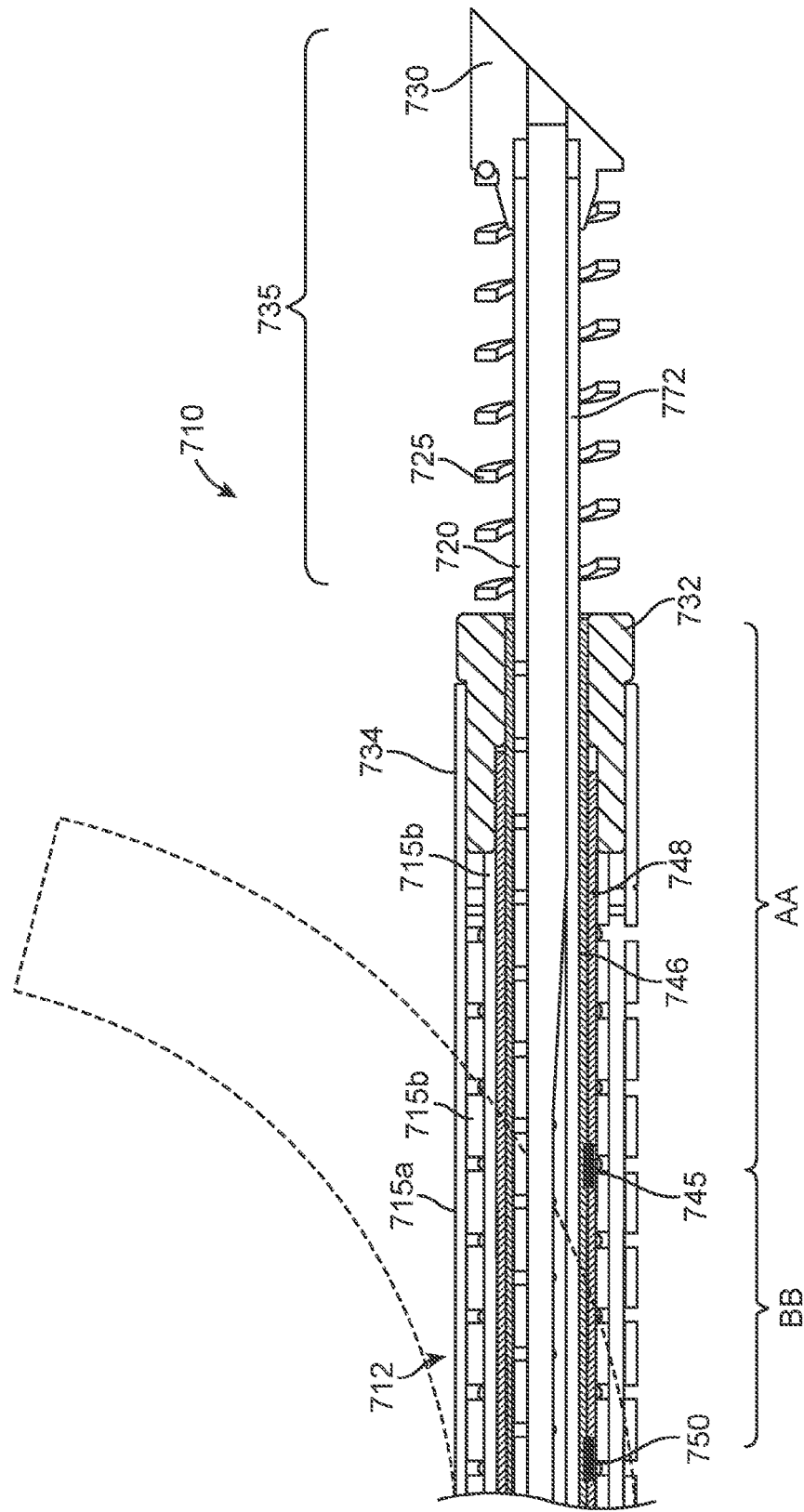
FIG. 40 illustrates the working end of an osteotome similar to that of FIGS. 38A-38B showing temperature sensors disposed within the working end.

FIG. 40 is an enlarged sectional view of a working end 710 of ablation osteotome similar to that of FIGS. 37-38B.

In this embodiment, shaft or introducer sleeve assembly 712 has an outside diameter of 4.5 mm or less, or 4.0 mm or less. In one embodiment, the diameter of introducer 712 is 3.5 mm and comprises outer sleeve 715a, intermediate sleeve 715b and inner sleeve 715c all of which are slotted to permit articulation of a portion of the working end as can be seen in phantom view in FIG. 41.

In FIG. 40, the extendable element or sleeve 720 is shown in an extended configuration which extends helical spring element 725 as described above. In this embodiment, the sleeve 720 and helical spring element 725 together with sharp tip 730 comprises a first polarity electrode coupled to an RF source 530A and controller 530B as described previously. An insulator 732 separates the helical spring 725 electrode from the distal portion 734 of the sleeve which comprises opposing polarity electrode 740. It can be seen that extendable sleeve 720 has a distal portion that is slotted to permit bending as the working end is articulated. The RF electrodes can function as described above (see FIG. 37) to ablate tissue.

In one aspect of the invention, the electrode surface portion of the extendable assembly 735 (sleeve 720 and helical element 725) is moveable from a non-extended position to an extended position during which the electrode surface area varies less than 10% between said non-extended and extended positions. In another embodiment, the electrode surface area varies less than 5% between said non-extended and extended positions. This aspect of the invention allows for similar ablation volumes per unit time no matter the dimension of the extendable assembly 735 since the surface are of the helical element 725 accounts for nearly all of the electrode surface area. The extendable element can have an electrode surface area of at least 40 mm2, at least 50 mm2, or at least 60 mm2.

FIG. 4041 further illustrates another aspect of the invention which includes at least one temperature sensor, also referred to as a temperature detecting element, in the working end for controlling or terminating RF energy delivery when tissue adjacent the temperature reaches a predetermined level.

In one variation, as shown in FIG. 40, a temperature detecting element 745 can be disposed between first and second dielectric sleeves 746 and 748 that insulate the introducer sleeve assembly 712 from the extendable sleeve 720. In an embodiment, the RF energy can be activated to ablate tissue until the boundary of ablated tissue adjacent the temperature detecting element 745 reached a predetermined temperature and the temperature detecting element signal can then be coupled to the controller to terminate RF energy delivery. In on embodiment, the temperature detecting element 745 can be disposed between first and second layers of a thin wall dielectric material, 746 and 748, such as PEEK that is used to insulate the opposing polarity electrodes from each other. In FIG. 40, the temperature detecting element 745 can be positioned dimension AA from the distal end of the introducer sleeve assembly 712 which can range from 5 mm to 15 mm. FIG. 40 depicts a second temperature detecting element 750 that can be positioned dimension BB from the first temperature detecting element 745 which can be a distance ranging from 5 mm to 15 mm.

As shown FIG. 40, a temperature detecting element 745 can be disposed on an outer radius of an articulated distal portion of the working end. In another embodiment, the temperature detecting element(s) can be disposed on an inner radius of the articulated distal portion of the working end.

Figure 41:
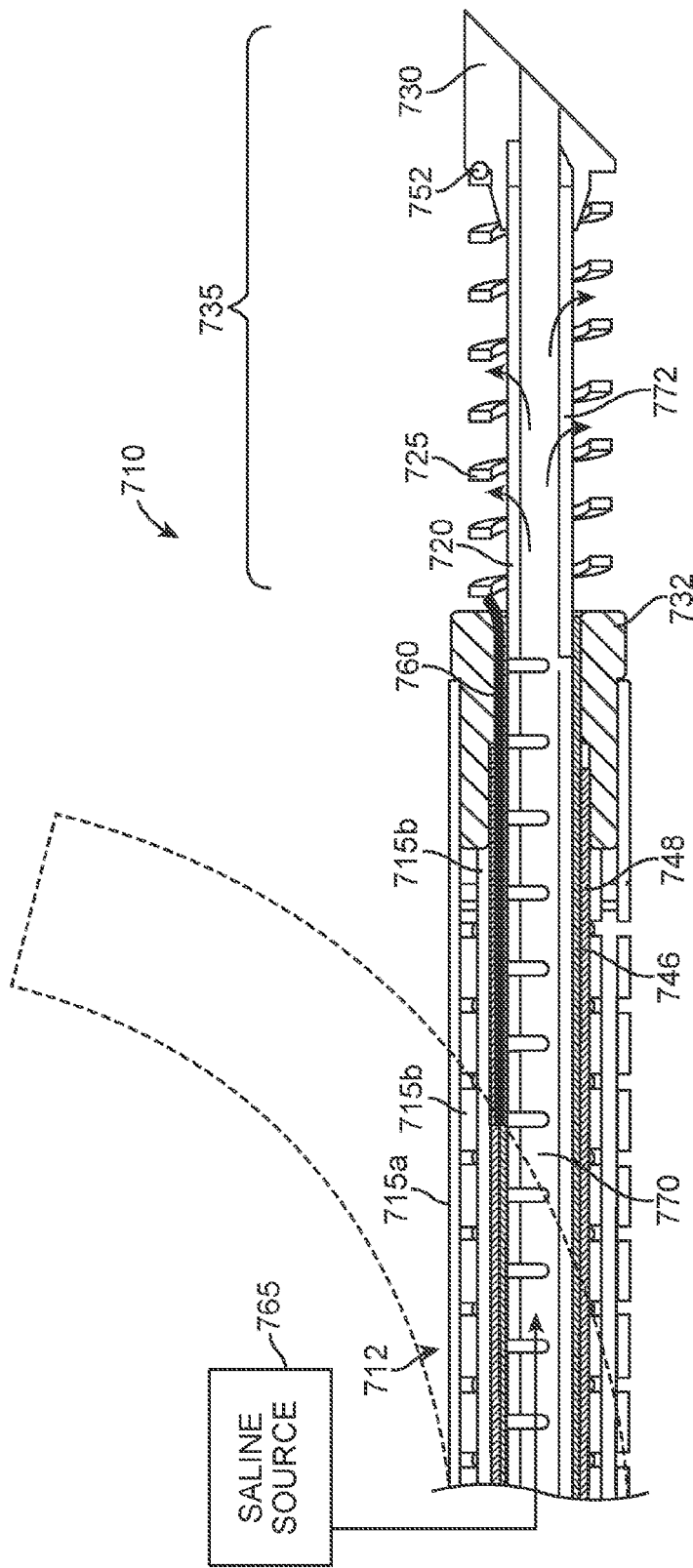
FIG. 41 illustrates another osteotome working end similar to that of FIGS. 38A-38B.

In FIG. 41, it can be seen that the helical element 725 has a distal end coupled, for example by weld 752, to the distal tip element 730 of the extendable assembly 735. FIG. 42 further shows that helical element 725 has a proximal end coupled to a safety wire 760 that extends proximally and is bonded to the introducer assembly, for example being secured with adhesives or other means between the first and second layers of dielectric material, 746 and 748.

In one embodiment shown in FIG. 41, a conductive fluid source 765 communicates with a lumen 770 extending through the extendable sleeve 720 to provide saline infusion through ports 772 into the region of tissue targeted for treatment.

In general, a method corresponding to the invention comprises introducing an elongated introducer sleeve comprising return electrode into targeted tissue, articulating a distal region of the introducer sleeve and extending an extendable member from the introducer sleeve, wherein the extendable member comprises an active or first polarity electrode having an electrode surface area that varies less than 10% between non-extended and extended positions, and activating an RF source, such that when activated, current flows between the extendable member and the introducer sleeve to apply energy to the targeted tissue. The method includes terminating activation of the RF source when a temperature sensor spaced apart from the first polarity electrode reaches a predetermined temperature. The temperature sensor can be spaced apart from the first polarity electrode by at least 5 mm, 10 mm or 15 mm. The method can target tissue in or near a bone such as a vertebra or long bone. The targeted tissue can be a tumor.

Another method of the invention comprises treating a tumor in or near bone which includes providing an elongated shaft with an articulating working end carrying first and second polarity electrodes, utilizing articulation of the working end to navigate the working end to a position in or near a bone tumor, activating an RF source, such that when activated, current flows between the first and second polarity electrodes to ablate the tumor; and terminating activation of the RF source when a temperature sensor spaced apart from the second polarity electrode reaches a predetermined temperature. In this method, the temperature sensor spacing from an active electrode is configured to provide a predetermined tissue ablation volume. As shown in FIG. 40, the working end can carry a plurality of axially spaced apart temperature sensors, and each sensor can be used to indicate a particular dimension of ablated tissue as each sensor reaches a predetermined temperature based on the expanding volume of ablated tissue.

In another embodiment, the medial and proximal regions of the outer sleeve can be covered with a thin-wall insulative material to provide a distal electrode surface having a predetermined surface area that matches the surface area of the helical element 725. The sleeve 720 at the interior of the helical element also can be covered with a thin-wall dielectric material. In use, the device then would operate in a truly bi-polar manner since the opposing polarity electrodes would have an equal surface area no matter the length of extension of the extendable assembly 735. In general, a device corresponding to the invention would comprise an elongate introducer having a distal end, wherein a surface portion of the introducer comprises an electrode, an extendable member including a helical element comprising an second electrode moveable from a non-extended position to an extended position from the introducer wherein the electrode surface area of the first electrode and the second electrode match no matter the non-extended or extended position of the second electrode.

In another variation of the invention under the present disclosure, the devices, systems and methods described herein can include the use of one or more temperature sensors (also called temperature detecting elements) to monitor, control, and/or otherwise provide a physician with the information needed to ensure a desired treatment.

The temperature sensor/temperature detecting element can comprise any element that can measure temperature of the adjacent tissue or measure temperature of the device immediately adjacent to tissue provide this information to a controller or other portion of the system as described herein. In most variations of the device, the temperature detecting element is used to assess temperature of the tissue before, during, or after application of energy. Examples of temperature detecting elements include thermocouples, resistance temperature detectors (RTDs), optical temperature measurement sensors, pyrometers. In addition, the present disclosure can include any type of temperature measurement device capable of determining a temperature of tissue or even parts of the device that would otherwise indicate a relative temperature of the tissue.

Figure 42A:
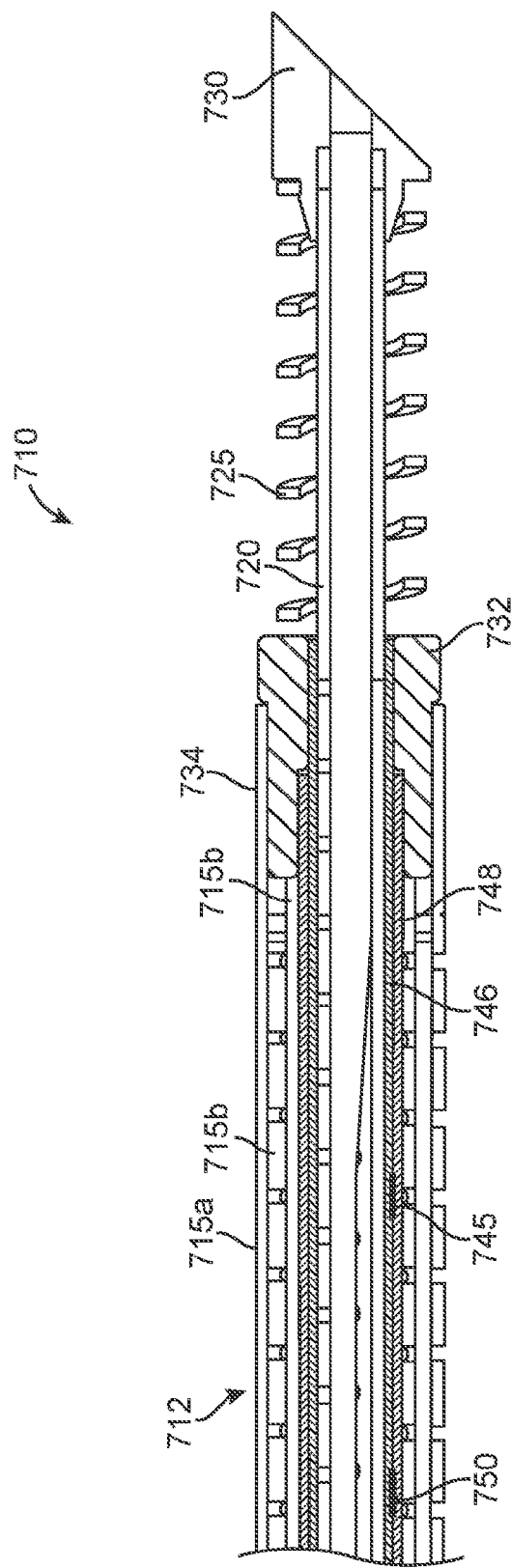
FIGS. 42A to 42E depict variations of devices having multiple temperature sensing elements adjacent to energy transfer portions.

FIG. 42A illustrates a device similar to that shown in FIG. 40 where a temperature detecting element 745 is disposed between first and second dielectric sleeves 746 and 748 that insulate the introducer sleeve assembly 712 from the extendable sleeve 720. As shown the temperature detecting element 745 can be disposed on an outer radius of an articulated distal portion of the working end. In addition, FIG. 42A shows a second temperature detecting element 750 positioned proximally from the first temperature detecting element 745 where spacing of such temperature detecting elements allows for control and/or monitoring a region of heated tissue as described below. However, variations of the devices allow for any number of temperature detecting elements to be used in any number of positions.

Figure 42B:
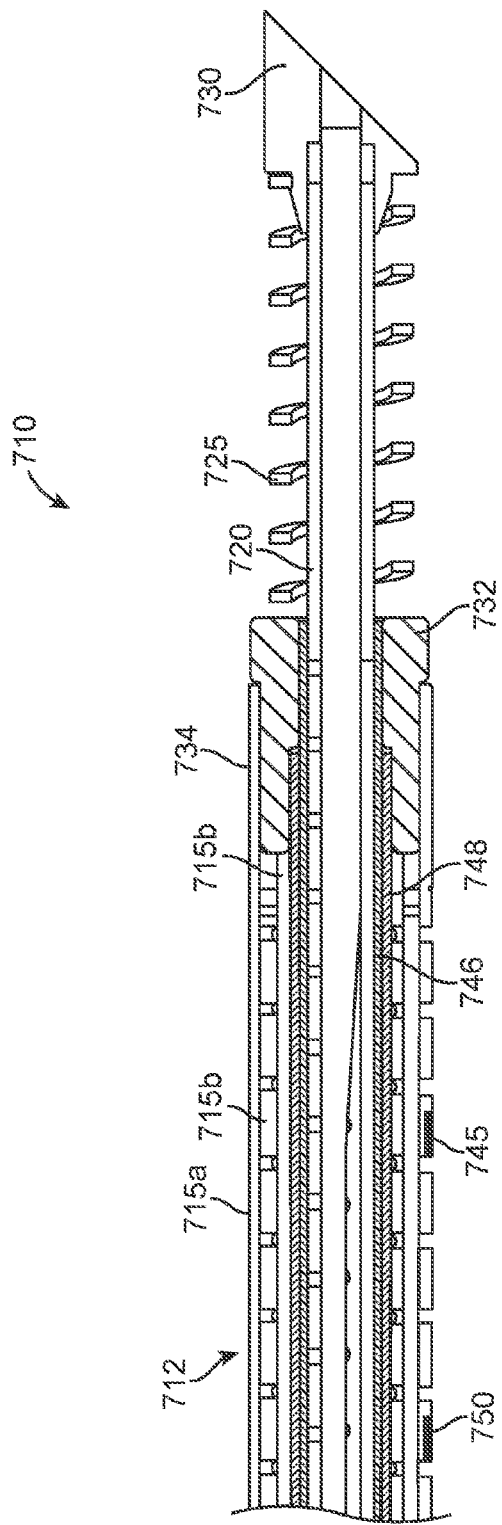

For example, FIG. 42B illustrates two temperature detecting element 245, 250 positioned on an exterior sleeve 715A of the device. In an additional variation, the temperature detecting elements can be positioned in between the slots of the exterior sleeve 715A.

Figure 42C:
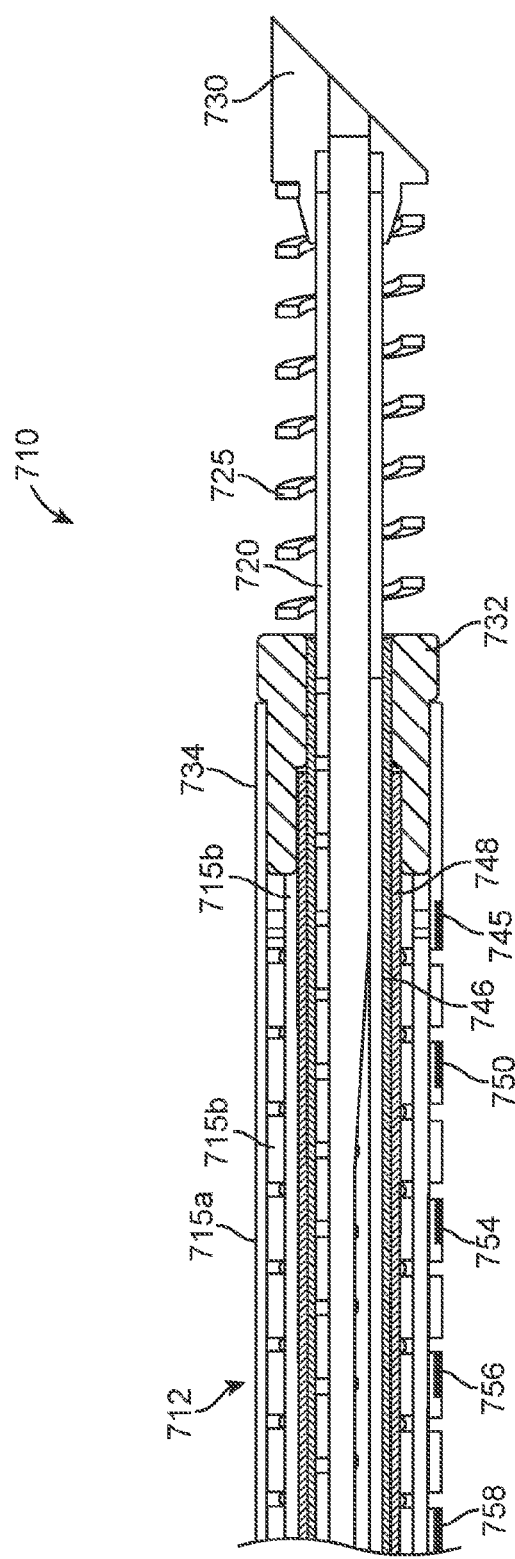
Figure 42D:
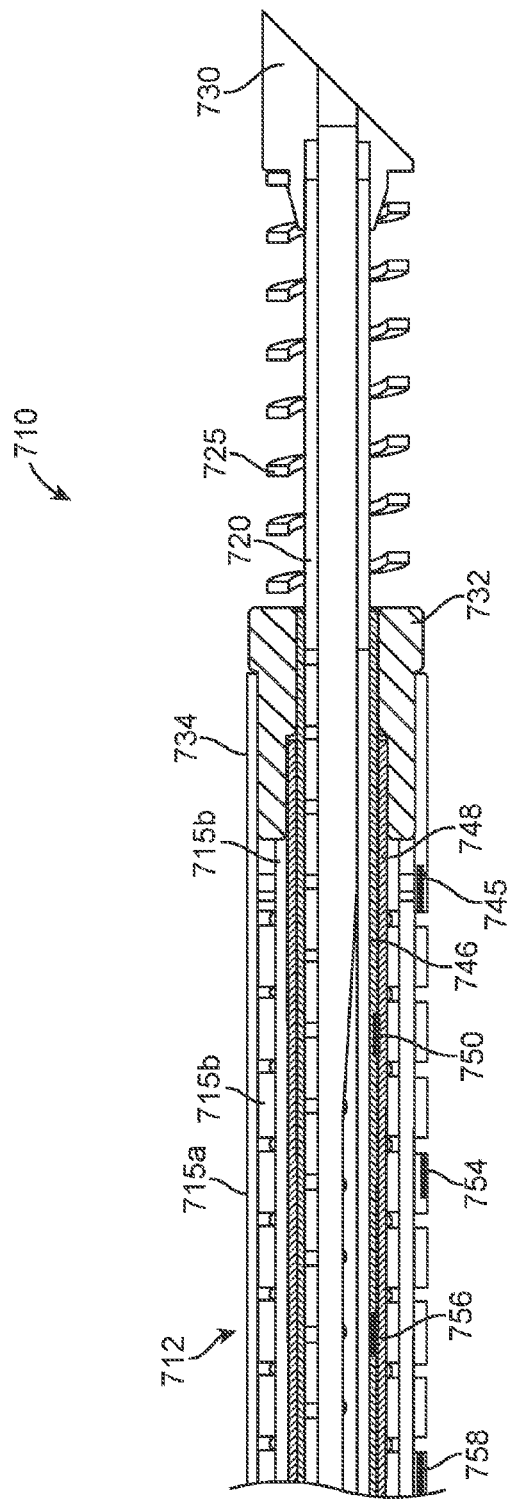
Figure 42E:
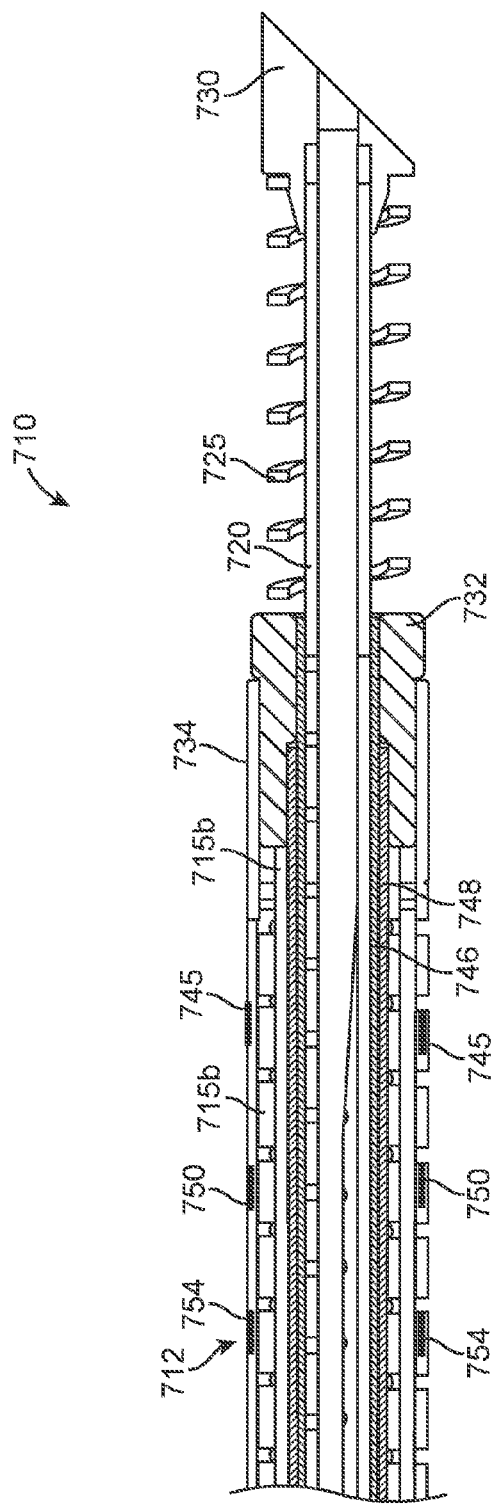

FIG. 42C shows another variation of a device having a plurality of temperature detecting elements 745, 750, 754, 756, 758 spaced along the shaft. Clearly, the temperature detecting elements could be located on an interior of the device, similar to that shown in FIG. 24A. Alternatively, as shown in FIG. 42D, temperature detecting elements can be included both on an interior and exterior of the device. FIG. 42E illustrates temperature detecting elements 745, 750, 754 located on both sides of the device. Alternatively, the temperature detecting element can comprise a ring type element that measures temperature adjacent to a full or partial circumference of the device. As noted herein, the temperature detecting elements can be evenly spaced along the shaft. Alternatively, the spacing of the elements can vary depending upon the intended application of the device. In addition, in most variations of the devices described herein, the temperature detecting elements are located proximally to the heating element of the device. However, additional variations include temperature detecting elements positioned distal to or adjacent to the heating element. The components of the various temperature detecting elements, such as wires, fibers, etc. are not illustrated for purposes of clarity. Furthermore, one or more temperature detecting elements can be positioned on sleeves that move axially relative to the energy transfer portion.

Figure 43A:
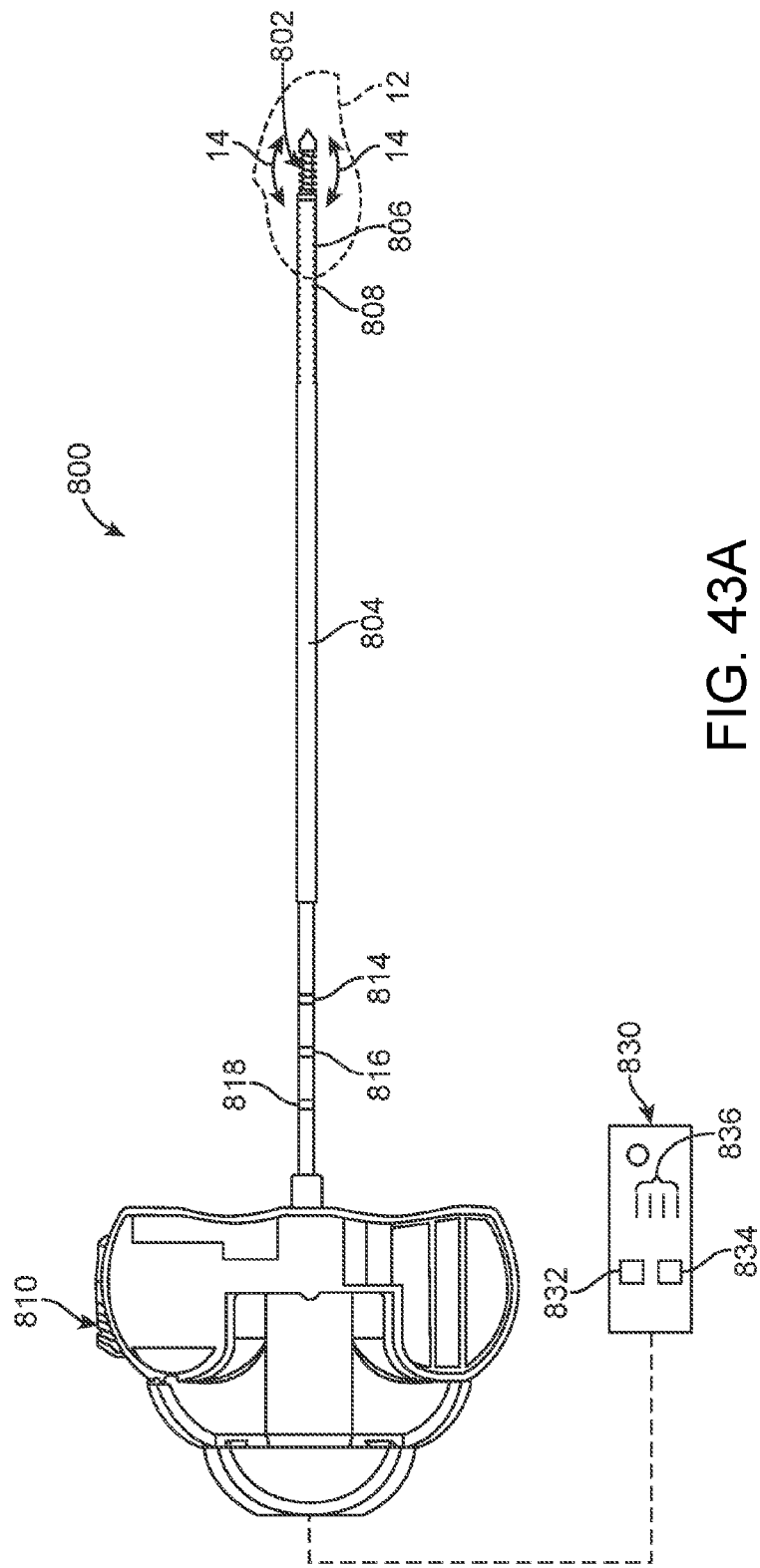
FIGS. 43A to 43C illustrates the use of one or more temperature sensing elements to monitor and/or control the growth of a region of treated tissue.
Figure 43B:
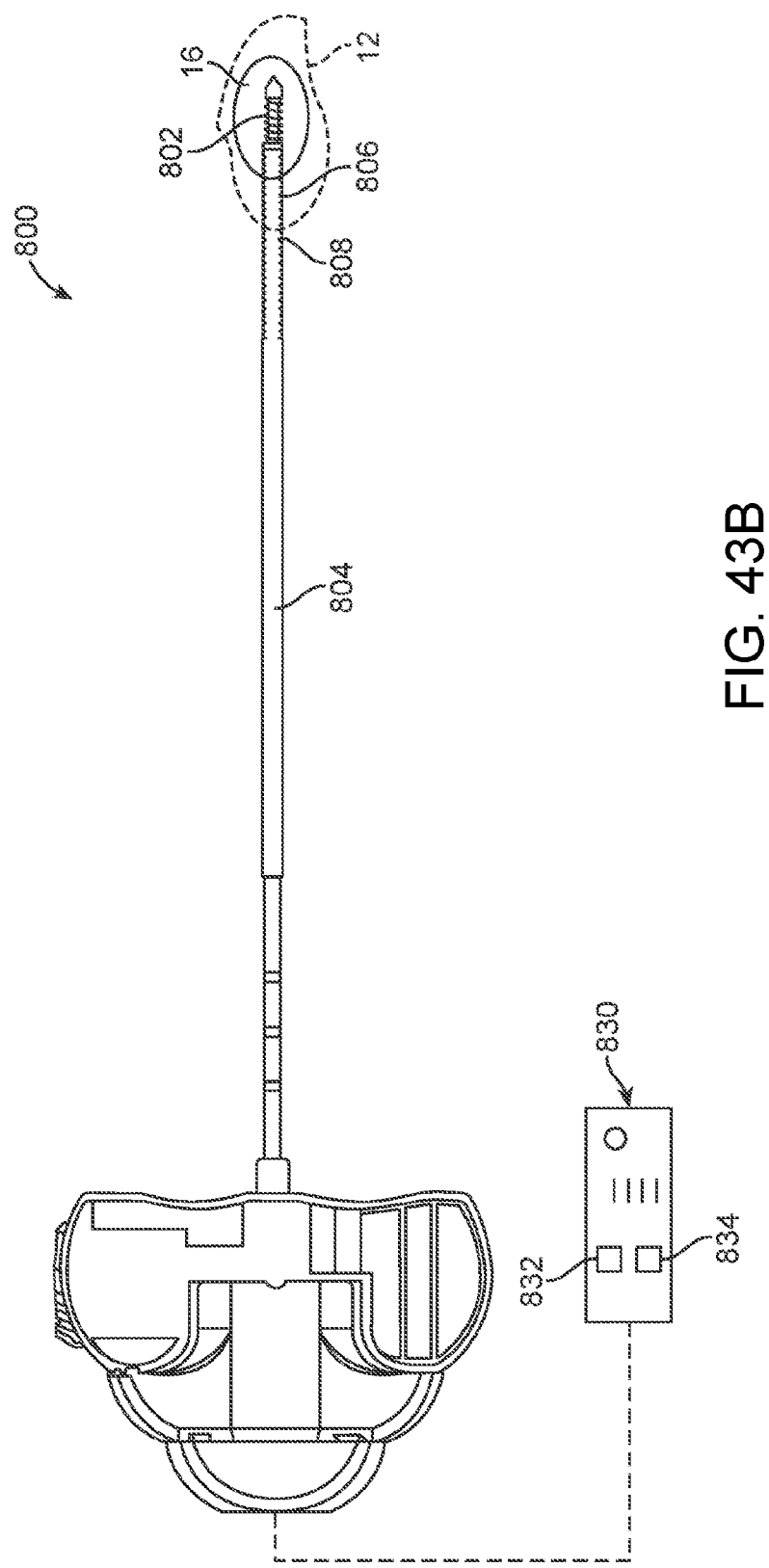
Figure 43C:
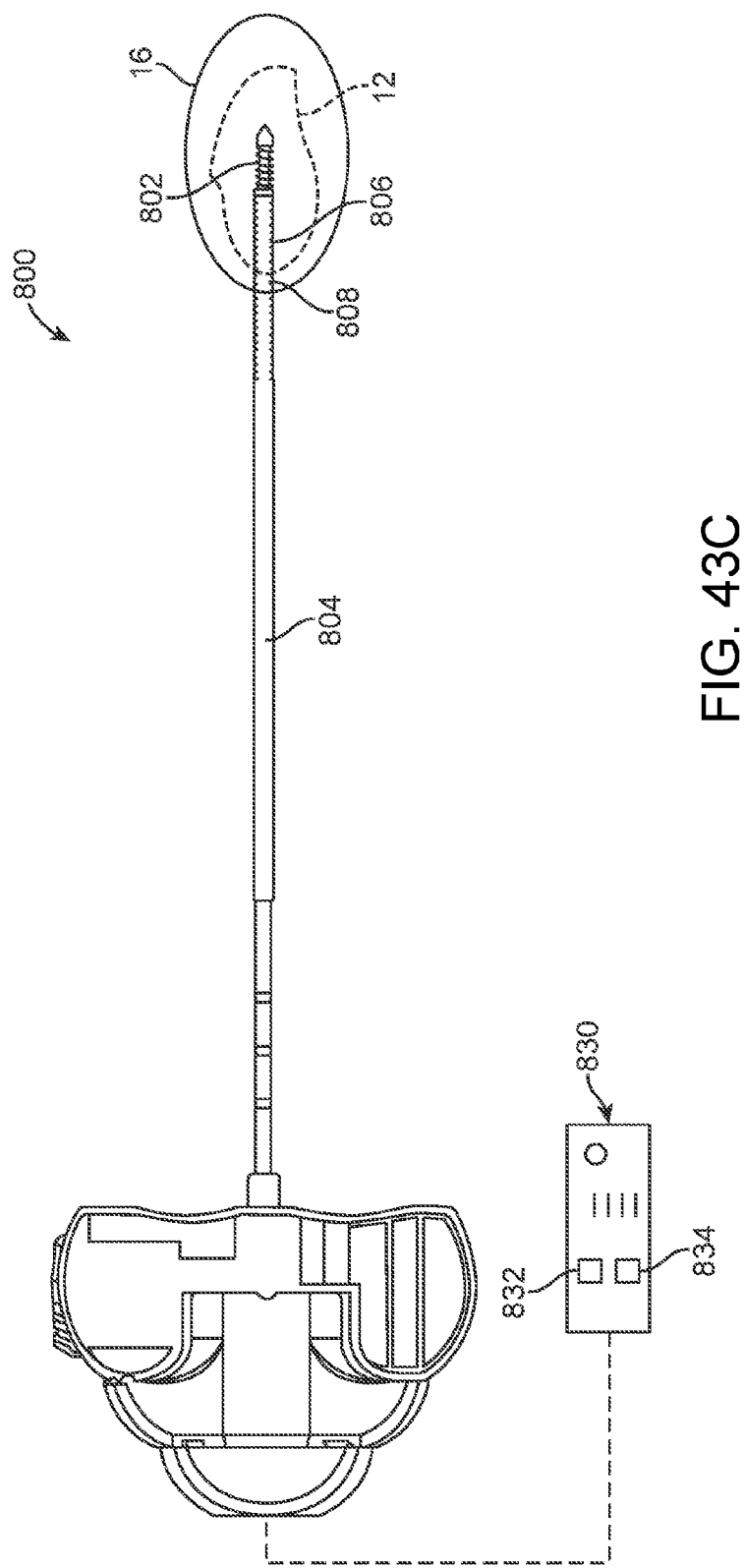

FIGS. 43A to 43C illustrate a concept of using temperature sensing element to guide a treatment where the temperature sensing elements are placed away from the energy transfer unit. FIG. 43A shows an example of a treatment device 800 having energy transfer portion 802 at a distal portion of a shaft 804. As discussed above, one effective variation of a device includes the use of RF energy configuration, either monopolar or bi-polar, that serves as the energy transfer portion. However, any number of energy transfer modes can be employed in the methods, systems and devices described herein where such modalities produced heated tissue. Such modalities can include, but are not limited to, resistive heating, radiant heating, coherent light, microwave, and chemical. In yet another variation, the devices can use radioactive energy modalities as well. Alternatively, variations of devices employing temperature based detection can employ cryosurgical energy configurations that rely upon the application of extreme cold treat tissue. Clearly, in such cases the methods, devices, and systems would monitor regions of cooled tissue rather than heated tissue.

Turning back to FIG. 43A, the treatment device 800 includes at least a first temperature detecting element 806 located axially relative to an energy transfer element 802. In some variations, the energy transfer element 806 is located proximally along an axis of the shaft from thee energy transfer unit 802. However, as described above, variations of the devices include placement of the temperature detecting elements as needed. FIG. 44A also shows a second temperature detecting element 808 located proximally to the first temperature detecting element 806. Again, the methods and procedures described herein can employ any number of temperature detecting elements.

The devices and methods also optionally include conveying temperature information on a controller 830. Variations of the controller 830 allow for display or conveyance of temperature information specific to each temperature detecting element. For example, in the variation shown in FIG. 43A, the first temperature detecting element can be coupled to display 832 while the second temperature detecting element 808 can be coupled to display 834. The controller can also optionally allow a physician to set temperature limits based on readings from each temperature sensing element. In such a case, if a measured temperature at a respective temperature sensing element exceeds the temperature limit, the system can end delivery of the energy or provide any other auditory or visual alert. The control unit 830 can be separate from a power supply or can be integrated into the power supply. Additional variations also include a control unit that can be integrated into a handle or other portion of the device 800.

In a first variation, a physician can position the distal end of the shaft 804 containing the energy transfer element 802 within a tumor 12. Clearly, the methods and procedures are not limited to treatment of a tumor. Instead, the device can be positioned in any target region that a physician seeks to treat. Once the device 800 and energy transfer element 802 are properly positioned, the physician can begin to apply energy to the energy transfer portion to cause an effect (as shown by arrows 14) in tissue that produces a region of affected tissue, e.g., a temperature of the tissue increases or decreases (as described above based on the energy modality used). For convenience, the method shall be discussed with respect to an area of heated tissue. Clearly, alternate variations of the device involve regions of cooled tissue.

FIG. 43B illustrates continued application of energy, which results in expansion of the region of heated tissue 16. The continued application of energy can occur intermittently or continuously. As the physician operates the device 800, the temperature detecting elements 806, 808 can monitor temperature of adjacent tissue. FIG. 44B depicts the region of heated tissue 16 as not having yet reached the first or second temperature sensing element 806, 808. The temperature measurements can occur intermittently, continuously, during application of energy, or in between intermittent applications of energy. Likewise, the temperature information 832, 834 can optionally be relayed to the controller 830.

FIG. 43C shows the heated region of tissue 16 expanded sufficiently such that it encompasses the desired region of tissue 12 or tumor. FIG. 27 also depicts the heated region of tissue 16 as being easily visually identified. However, during an actual treatment, the physician simply cannot observe the actual perimeter of the zone of heated tissue 16. Instead, the temperature detecting elements 806, 808 will be able to detect the heated region of tissue 16 as the temperature of the tissue adjacent to the temperature detecting elements 806, 808 rises.

The temperature measured by the temperature detecting elements 806, 808 can also provide the physician with the ability to monitor the progression of the region of heated tissue 16. For instance, the volume, length, area, or other characteristic of the region of heated tissue can be approximated by obtaining a temperature that is associated with the perimeter of the region. Analytic correlation of this associated temperature to the physical characteristic of the heated tissue can be determined from bench testing, animal testing, cadaver testing, and/or computer analysis. Such analytic correlation allows the volume of an area of heated tissue to be approximated based on the temperature of the outer perimeter of that region. In the illustrated example of FIG. 43C, there exists a pre-determined temperature associated with an area of heated tissue having known dimension. Once the measured temperature at temperature detecting element 808 reaches this associated temperature, the physician can stop the treatment. Alternatively, or in addition, the system or controller 830 can include safety algorithms to automatically warn the physician to cease treatment or even to perform a safety shutoff of the system if a given temperature is reached or if the temperature remains constant while power is applied to the electrode.

In additional variations, the monitoring of the size or profile of the region of heated tissue can be used to control the application of applied energy. For example, as the measured temperature approaches the associated temperature, the controller can reduce power to prevent any lags in measurement from overshooting the target treatment zone.

The variation described above in FIGS. 43A to 43C can also be used to position the device 800 relative to a desired target region 12. For example, the temperature detecting elements 806, 808, can be radiopaque (or can have radiopaque markers) so that a physician can place the appropriate temperature detecting element in a target area or at a perimeter of the target area. In the example shown in FIG. 43A, a physician could position the second temperature detecting element 808 just outside of a tumor or as otherwise desired. Once the measured temperature reaches the associated temperature the physician can stop application of energy and reposition the device as needed or stop treatment. E.g. A physician may choose to use 50 C or 55 C as a target temperature for a specific temperature detecting element based on pre-planning. Once that temperature reaches the desired level; e.g. 50 C or 55 C then the physician may stop delivering any further energy to the tissue by turning off energy delivery. In another embodiment, controller will have an algorithm where a physician inputs the desired temperature for a specific temperature detecting element and controller will apply energy. Energy delivery will stop once the desired temperature is achieved. Further enhancement to the controller may also allow physician with an ability to set desired amount of time associated with each target temperature where controller will maintain energy level sufficient to control the temperature for desired amount of time and then turn off the energy delivery.

FIG. 43A also depicts a variation of the device as having visible markers 814, 816, and 818 located on a shaft. The markers can be used to assist the physician in positioning of the energy transfer elements and/or temperature detecting elements. For example, in the illustrated variation, the device can be used with an introducer cannula of a known size so that marker 814 informs the physician that the distal tip or energy transfer element is positioned at the opening of the cannula. Likewise, markers 816 and 818 can inform the physician that energy transfer elements 806 and 808 are respectively located at the opening of the cannula.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

The invention claimed is:

1. A medical device comprising:
   a handle including an actuator member; and
   a shaft extending from the handle and having a deflectable section that is moveable between a linear configuration and an articulated configuration upon application of an axial compression to the shaft upon movement of the actuator member;
   wherein the shaft comprises at least a first sleeve having a first plurality of keyed slots, wherein the keyed slots of the first plurality of keyed slots each comprise a first edge that forms a keyed portion, a second edge that forms a key receiving portion, and a third edge and a fourth edge that form a laterally extending portion;
   wherein a depth of the extending portion is different from the depth of an adjacent extending portion;

wherein, when the deflectable section is in the linear configuration, each keyed slot of the first plurality of keyed slots forms a gap that separates lateral sides of the keyed portion from lateral sides of the key receiving portion;

wherein, when the deflectable section is in the articulated configuration, the keyed portion engages the key receiving portion to nest together and increase a resistance to twisting deformation of the shaft; and wherein the keyed portion and the key receiving portion are each tapered such that the lateral sides of the keyed portion and the receiving portion form a first taper angle that allows the keyed portion to nest together with the key receiving portion to form a contiguous surface.

2. The medical device of claim 1, wherein the first plurality of keyed slots comprises a plurality of proximal keyed slots, each having a depth that differs from an adjacent proximal keyed slot.

3. The medical device of claim 1, where the shaft further comprises a second tube having a plurality of second slots and a plurality of second tabs slidably received in each of the second slots and located on a second side of the second tube opposite to the first side of the first tube;

wherein movement of the actuation member causes compression of the first and the second tubes such that the first slots engage the first tabs and the second slots engage the second tabs to cause the deflectable section to assume the articulated configuration and to increase torsional resistance of the deflectable section.

4. The medical device of claim 3, where the plurality of second slots and the plurality of second tabs each includes a second taper angle allowing the second keyed portion to nest together with the second key receiving portion forming a second contiguous surface.

5. The medical device of claim 1, further comprising a sharp tip located at a distal tip of the working end, the sharp tip adapted to penetrate hard tissue and a point of the sharp tip is offset to engage hard tissue when advanced therein to assist in deflecting the working end.

6. The medical device of claim 1, where the articulated configuration is limited to a single plane.

7. The medical device of claim 1, where the first plurality of keyed slots are laser cut into a continuous structure.

8. The medical device of claim 1, where the first taper angle varies between at least two of the plurality of first keyed slots and first keyed receiving portion.

9. The medical device of claim 1, further comprising a torque limiter having a torque threshold and rotatably coupling the first sleeve to the handle, where application of a torque exceeding the torque threshold causes rotation of the torque limiter relative to the handle to rotate the first sleeve.

10. The medical device of claim 9, where the torque limiter comprises a plurality of resistance surfaces that are deflected upon application of a rotational force to the shaft.

11. The medical device of claim 1, further comprising a first conductive portion on the shaft electrically coupleable to a first pole of a power supply and a second conductive element coupled to the shaft being coupled to a second pole of the power supply.

12. The medical device of claim 11, where the second conductive element comprises an extendable element extendible from the shaft, where the extendable element.

13. A medical device for treating a region of tissue by mechanically displacing the tissue, the medical device comprising:

a handle including an actuator member;

a shaft extending from the handle and having a deflectable section that is moveable between a linear configuration and an articulated configuration that can compress tissue as the shaft is moved in a linear direction, the shaft comprising a plurality of layers including at least a first layer and a second layer, the second layer being slidable relative to the first layer;

the first layer located adjacent to a first side of the shaft and having a plurality of first recesses, each with a first tab located therein, wherein lateral sides of the first tab form a first taper causing a base of the first tab to be wider than an end of the first tab;

the first layer having a plurality of circumferentially extending first slots, wherein a radial depth of the extending first slot is different than the radial depth of an adjacent first slot;

the second layer located adjacent to a second side of the shaft, the second side of the shaft being radially opposite to the first side of the shaft, the second layer having a plurality of second recesses, each with a second tab located therein, wherein lateral sides of the second tab form a first taper causing a base of the second tab to be wider than an end of the second tab;

the second layer having a plurality of laterally extending second slots, wherein a depth of the extending second slot is different than the depth of an adjacent second slot;

wherein, when the deflectable section is in the linear configuration, the lateral sides of the first recess and first tab have a first clearance gap, and the lateral sides of the second recess and second tab have a second clearance gap;

wherein movement of the actuation member causes compression of the shaft such that the first recess engages the first tab and the second recess engages the second tab to reduce the first clearance gap and second clearance gap, thereby causing movement of the deflectable section towards the articulated configuration; and wherein reducing of the first clearance gap and second clearance gap increases torsional resistance of the deflectable section.

\* \* \* \* \*